(12) United States Patent
Lin et al.

(10) Patent No.: US 11,098,028 B2
(45) Date of Patent: *Aug. 24, 2021

(54) PROCESS FOR THE MANUFACTURING OF MEDICAMENTS

(71) Applicant: Genentech, Inc., South San Francisco, CA (US)

(72) Inventors: Jinguang Lin, Shanghai (CN); Alexandra Chestakova, Sunnyvale, CA (US); Wei Gu, Shanghai (CN); Hans Iding, Rheinfelden (CH); Jing Li, Shanghai (CN); Xin Linghu, Burlingame, CA (US); Patrik Meier, Basel (CH); Chunbo Sha, Shanghai (CN); Jeffrey Stults, Half Moon Bay, CA (US); Youchu Wang, Shanghai (CN); Haiming Zhang, San Mateo, CA (US); Jianqian Zhang, Shanghai (CN); Tao Zhang, Shanghai (CN)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/535,752

(22) Filed: Aug. 8, 2019

(65) Prior Publication Data

US 2019/0367484 A1    Dec. 5, 2019

Related U.S. Application Data

(60) Division of application No. 15/866,899, filed on Jan. 10, 2018, now Pat. No. 10,611,753, which is a continuation of application No. 15/285,781, filed on Oct. 5, 2016, now abandoned, which is a continuation of application No. PCT/CN2015/076083, filed on Apr. 8, 2015.

(30) Foreign Application Priority Data

Apr. 9, 2014 (WO) ................ PCT/CN2014/075011

(51) Int. Cl.
| | | |
|---|---|---|
| *C07D 401/14* | (2006.01) | |
| *C07D 401/04* | (2006.01) | |
| *C12P 17/16* | (2006.01) | |
| *A61P 35/00* | (2006.01) | |
| *A61P 25/00* | (2006.01) | |
| *A61P 29/00* | (2006.01) | |

(52) U.S. Cl.
CPC ............ *C07D 401/14* (2013.01); *A61P 25/00* (2018.01); *A61P 29/00* (2018.01); *A61P 35/00* (2018.01); *C07D 401/04* (2013.01); *C12P 17/165* (2013.01)

(58) Field of Classification Search
CPC ... C07D 401/14; C07D 401/04; C12P 17/165; A61P 29/00; A61P 25/00
See application file for complete search history.

(56) References Cited

U.S. PATENT DOCUMENTS 10,611,753 B2 *   4/2020   Lin ................... C07D 401/14

* cited by examiner

*Primary Examiner* — Tracy Vivlemore
*Assistant Examiner* — Ebenezer O Sackey

(57) ABSTRACT

The present invention provides a process for the manufacture of a compound of formula VIIIa and salts forms of VIIIa where $R^c$ is an aryl sulfonic acid

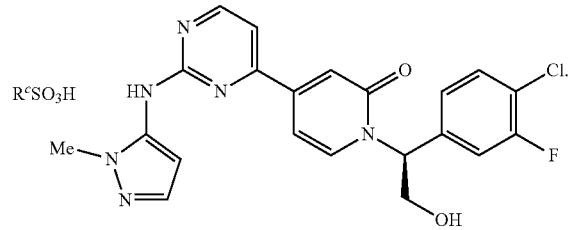

(VIIIa)

2 Claims, 22 Drawing Sheets

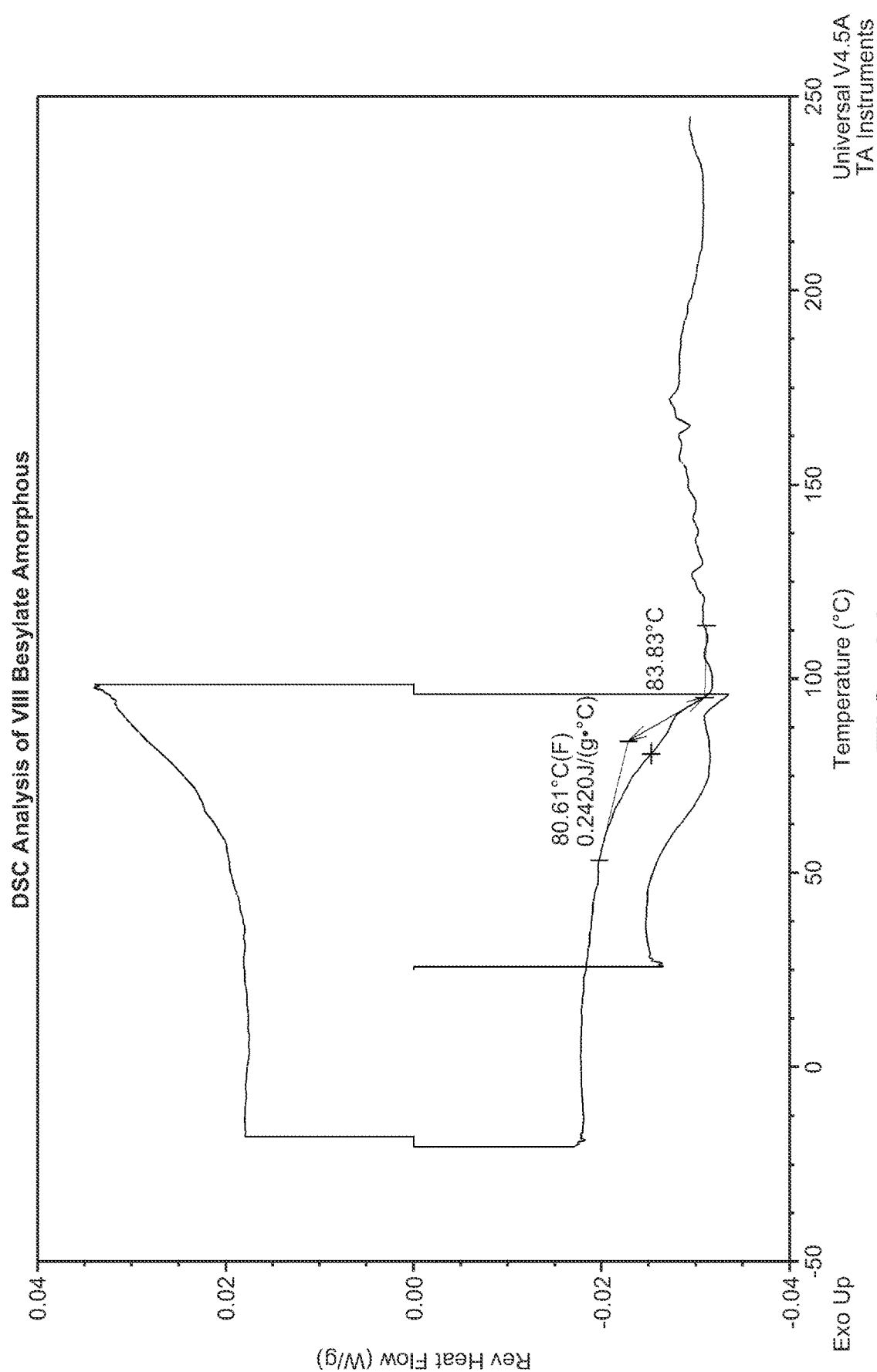

PROCESS FOR THE MANUFACTURING OF MEDICAMENTS

CROSS REFERENCE TO RELATED APPLICATIONS

This application is a divisional of U.S. application Ser. No. 15/866,899, filed Jan. 10, 2018 which claims priority to continuation of U.S. application Ser. No. 15/285,781, filed Apr. 8, 2015 and claims priority to PCT international application no. PCT/CN2015/076083, filed Apr. 8, 2015, which claims priority under 35 U.S.C. § 119 to PCT international application no. PCT/CN2014/075011, filed Apr. 9, 2014, which applications are hereby incorporated by reference in their entirety.

BACKGROUND OF THE INVENTION

The processes involved in tumor growth progression and metastasis are mediated by signaling pathways that are activated in cancer cells. The ERK pathway plays a central role in regulating mammalian cell growth by relaying extra-cellular signals from ligand-bound cell surface receptor tyrosine kinase ("RTK's"), such as ErbB family, PDGF, FGF, and VEGF receptor tyrosine kinases. Activation of an RTK induces a cascade of phosphorylation events that begins with activation of Ras. Activation of Ras leads to the recruitment and activation of Raf, a serine-threonine kinase. Activated Raf then phosphorylates and activates MEK1/2, which then phosphorylates and activates ERK1/2. When activated, ERK1/2 phosphorylates several downstream targets involved in a multitude of cellular events, including cytoskeletal changes and transcriptional activation. The ERK/MAPK pathway is one of the most important for cell proliferation, and it is believed that the ERK/MAPK pathway is frequently activated in many tumors. Ras genes, which are upstream of ERK1/2, are mutated in several cancers, including colorectal, melanoma, breast and pancreatic tumors. The high Ras activity is accompanied by elevated ERK activity in many human tumors. In addition, mutations of BRAF, a serine-threonine kinase of the Raf family, are associated with increased kinase activity. Mutations in BRAF have been identified in melanomas (60%), thyroid cancers (greater than 40%) and colorectal cancers. These observations indicate that the ERK1/2 signaling pathway is an attractive pathway for anti-cancer therapies in a broad spectrum of human tumors (M. Hohno and J. Pouyssegur, *Prog. in Cell Cycle Res.* 2003 5:219).

The ERK pathway has also been cited as a promising therapeutic target for the treatment of pain and inflammation (Ma, Weiya and Remi, Quirion. "The ERK/MAPK Pathway, as a Target For The Treatment Of Neuropathic Pain" *Expert Opin. Ther. Targets.* 2005 9(4):699-713, and Sommer, Claudia and Frank Birklein "Resolvins and Inflammatory Pain" *F1000 Medicine Reports* 2011 3:19).

Therefore, small-molecular inhibitors of ERK activity (i.e., ERK1 and/or ERK2 activity) would be useful for treating a broad spectrum of cancers, such as, for example, melanoma, pancreatic cancer, thyroid cancer, colorectal cancer, lung cancer, breast cancer, and ovarian cancer, as well as a treatment for pain and inflammation, such as arthritis, low back pain, inflammatory bowel disease, and rheumatism. The present invention provides a process and intermediates for making (S)-1-(1-(4-chloro-3-fluorophenyl)-2-hydroxyethyl)-4-(2-((1-methyl-1H-pyrazol-5-yl)amino) pyrimidin-4-yl)pyridin-2(1H)-one, pharmaceutically acceptable salts thereof, and crystalline forms of the salts.

The present invention also provides pharmaceutical compositions comprising the salts or crystalline forms of the salts, and methods of using the salts and crystalline forms of the salts. A synthesis of (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one is set forth in WO 2013/130976.

SUMMARY OF THE INVENTION

The present invention provides processes for the manufacture of I which is a useful intermediate that can be used in the manufacture VIII. (WO2013/130976) Compound VIII is an ERK inhibitor and a useful medicament for treating hyperproliferative disorders. The process provides an efficient route to VIII and to the useful intermediates VI and VII. Alkylation of VII with VI affords I, which ultimately is condensed with 1-methyl-1H-pyrazol-5-amine (XIV). (SCHEME A)

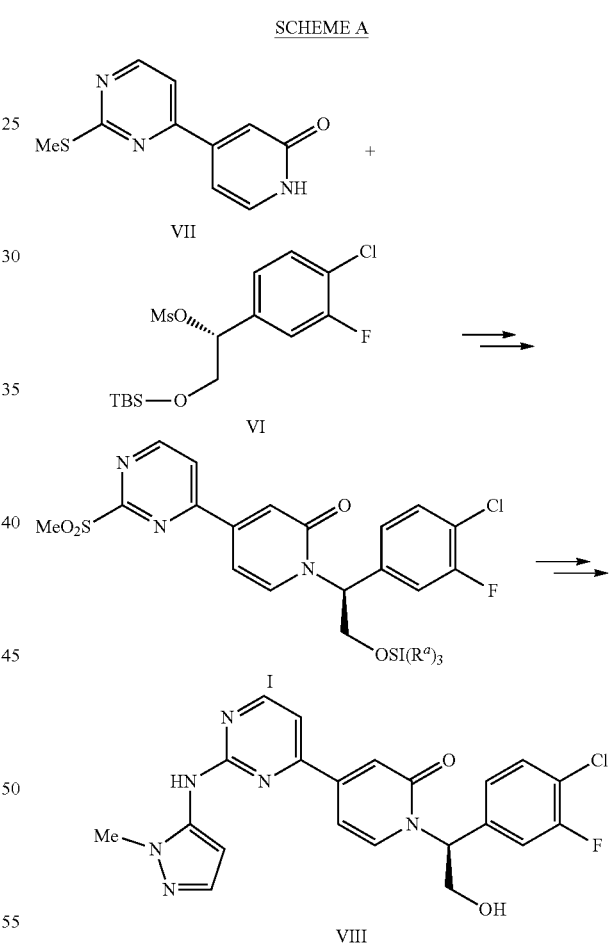

The present invention further provides an asymmetric enzymatic reduction which permits the stereospecific reduction of 1-(4-chloro-3-fluorophenyl)-2-hydroxyethanone to afford (R)-1-(4-chloro-3-fluorophenyl)ethan-1,2-diol (IV).

The present invention also provides an improved process to prepare 4-(2-(methylthio)pyrimidin-4-yl)pyridin-2(1H)-one (VII).

The present invention provides a crystalline besylate salt (VIIIb) with desirable physical properties that permit ready formulation and good bioavailability.

In embodiment 1, the present invention provides processes for the preparation of a compound of formula VIII, the processes comprising the steps of:

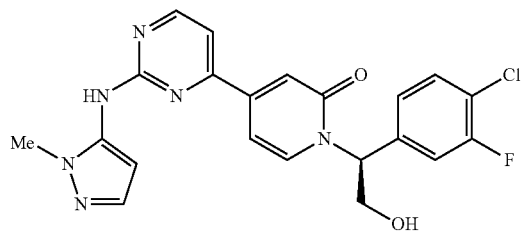

VIII (a) contacting 4-bromo-1-chloro-2-fluorobenzene with a metallating agent in an aprotic organic solvent to afford an organomagnesium compound, which is reacted with 2-chloro-N-methoxy-N-methylacetamide to afford 2-chloro-1-(4-chloro-3-fluorophenyl)ethanone (II);

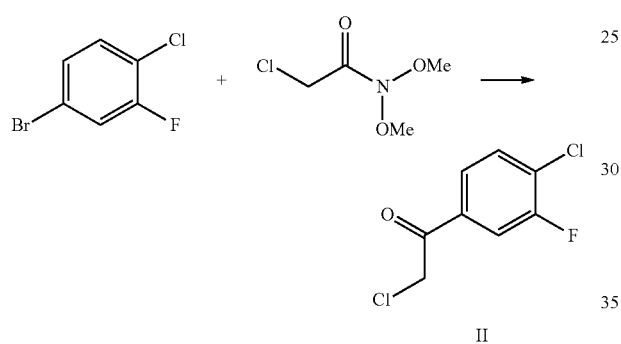

II (b) contacting II with sodium formate and formic acid in aqueous ethanol to afford 1-(4-chloro-3-fluorophenyl)-2-hydroxyethanone (III)

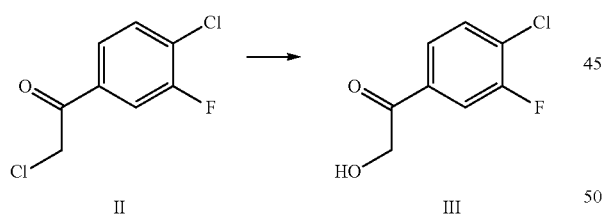

(c) contacting III with a ketoreductase to afford (R)-1-(4-chloro-3-fluorophenyl)ethane-1,2-diol (IV);

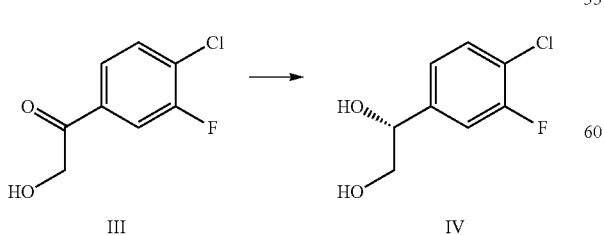

(d) contacting IV with a silyl chloride $(R^a)_3SiCl$ and at least one base in a non-polar aprotic solvent to afford (V), and subsequently adding sulfonylchloride $R^bS(O)_2Cl$ to afford VI, wherein $R^a$ is independently in each occurrence $C_{1-6}$ alkyl or phenyl and $R^b$ is selected from $C_{1-4}$ alkyl or phenyl, optionally substituted with 1 to 3 groups independently selected from $C_{1-3}$ alkyl, halogen, nitro, cyano, or $C_{1-3}$ alkoxy;

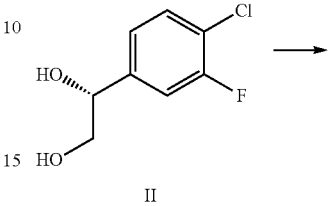

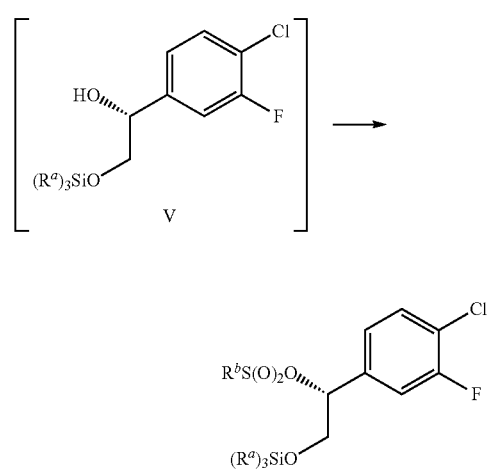

(e) contacting 4-(2-(methylsulfonyl)pyrimidin-4-yl)pyridin-2(1H)-one (VII) with a strong base in an organic solvent and subsequently adding VI to afford XI;

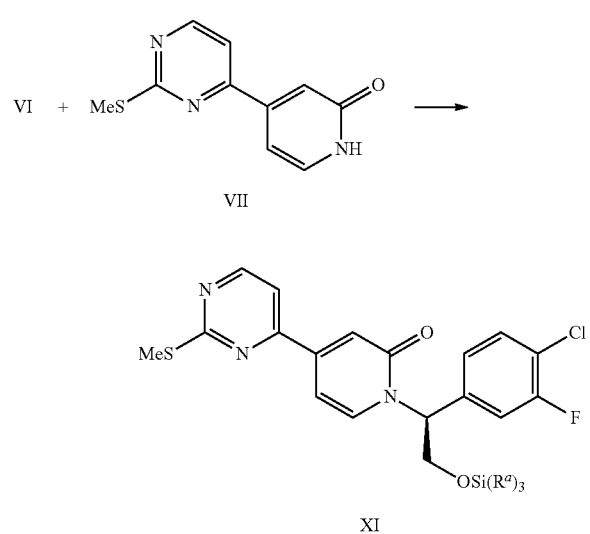

(f) treating XI with an oxidizing agent to afford I;

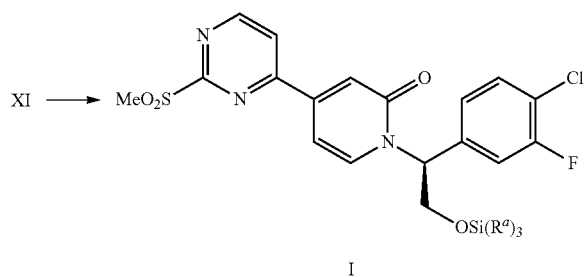

(g) treating 1-methyl-1H-pyrazol-5-amine with a strong base in an aprotic solvent at reduced temperature and adding the compound of formula I to afford IX; and,

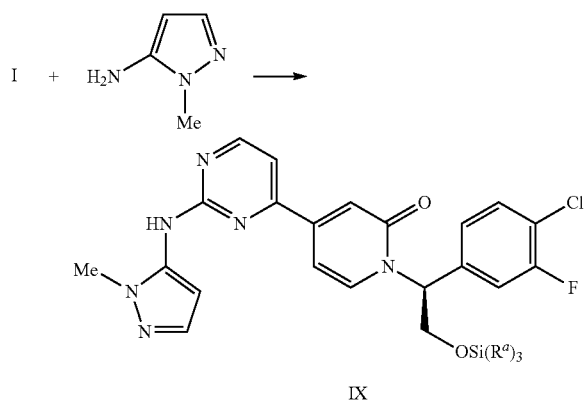

(h) contacting IX with a de-silylating agent to afford VIII.

In embodiment 2, the present invention provides processes according to embodiment 1 wherein the ketoreductase in step (c) affords an enantiomeric excess at least about 98%.

In embodiment 3, the present invention provides processes of embodiment 2 wherein the ketoreductase in step (c) is KRED-NADH-112.

In embodiment 4, the present invention provides processes of embodiment 2 wherein step (c) further comprises NADH or NADPH as a cofactor.

In embodiment 5, the present invention provides processes of embodiment 4 wherein the cofactor is regenerated with a cosubstrate selected from a secondary alcohol or from an additional enzyme selected from alcohol dehydrogenase, glucose dehydrogenase, formatted dehydrogenase, glucose-6-phosphate dehydrogenase, phosphite dehydrogenase or hydrogenase.

In embodiment 6, the present invention provides processes of any of embodiment 2 to 5 wherein the ketoreductase step is performed in an aqueous medium in the presence of organic cosolvent at a temperature between 1 and 50° C.

In embodiment 7, the present invention provides processes of embodiment 6 wherein the ketoreductase step produces a homogeneous suspension.

In embodiment 8, the present invention provides processes of embodiment 1 wherein the silyl chloride is tert-butyldimethylsilyl chloride, the sulfonyl chloride is methanesulfonyl chloride, the bases in step (d) are DMAP and TEA and the non-polar aprotic solvent is DCM and in step (e) the organic solvent is dioxane.

In embodiment 9, the present invention provides processes of embodiment 1 wherein $(R^a)_3Si$ is tert-butyldimethylsilyl, $R^b$ is methyl, and in step (e) the strong base is potassium hexamethyldisilazane and the organic solvent is diglyme.

In embodiment 10, the present invention provides processes of embodiment 1 wherein in step (a) the metallating agent is i-PrMgCl and LiCl and the solvent is THF, in step (c) the ketoreductase is KRED-NADH-112 and step (c) further comprises the cofactor NAD and the cofactor recycling agent glucose dehydrogenase, in step (d) $(R^a)_3Si$ is tert-butyldimethylsilyl, $R^b$ is methyl, the bases are DMAP and TEA and the non-polar aprotic solvent is DCM, and in step (e) the strong base is potassium hexamethyldisilazane and the organic solvent is diglyme.

In embodiment 11, the present invention provides processes of embodiment 1 wherein in step (a) the metallating agent is i-PrMgCl and LiCl and the solvent is THF, in step (c) the ketoreductase is KRED-NADH-112 and step (c) further comprises the cofactor NAD and the cofactor recycling agent is glucose dehydrogenase, in step (d) $(R^a)_3Si$ is tert-butyldimethylsilyl, $R^b$ is methyl, the bases are DMAP and TEA and the non-polar aprotic solvent is DCM, in step (e) the strong base is potassium hexamethyldisilazane and the organic solvent is diglyme, and in step (g) the strong base is potassium hexamethyldisilazane and the aprotic solvent is THF.

In embodiment 12, the present invention provides processes of embodiment 1 wherein in step (a) the metallating agent is i-PrMgCl and LiCl and the solvent is THF, in step (c) the ketoreductase is KRED-NADH-112 and step (c) further comprises the cofactor NAD and cofactor recycling agent is glucose dehydrogenase, in step (d) $(R^a)_3Si$ is tert-butyldimethylsilyl, $R^b$ is methyl, the bases are DMAP and TEA and the non-polar aprotic solvent is DCM, in step (e) the strong base is potassium hexamethyldisilazane and the organic solvent is diglyme, in step (g) the strong base is potassium hexamethyldisilazane and the aprotic solvent is THF, and in step (h) the desilylating agent is methanolic HCl.

In embodiment 13, the present invention provides processes according to embodiment 1 wherein the compound VIII from step h is contacted with a sulfonic acid in an organic solvent and water to afford a salt of VIIIa where $R^c$ is an aryl sulfonic acid

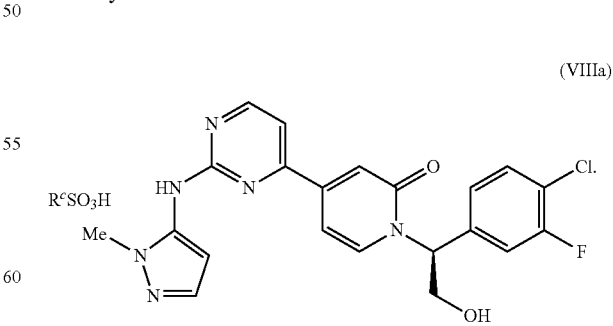

(VIIIa)

In embodiment 14, the present invention provides processes according to embodiment 13 wherein $R^cSO_3H$ is benzenesulfonic acid and the solvent is methyl ethyl ketone and water to afford the besylate salt VIIIb.

In embodiment 15, the present invention provides processes for the preparation of 4-(2-(methylsulfonyl)pyrimidin-4-yl)pyridin-2(1H)-one (VII) comprising the steps of:

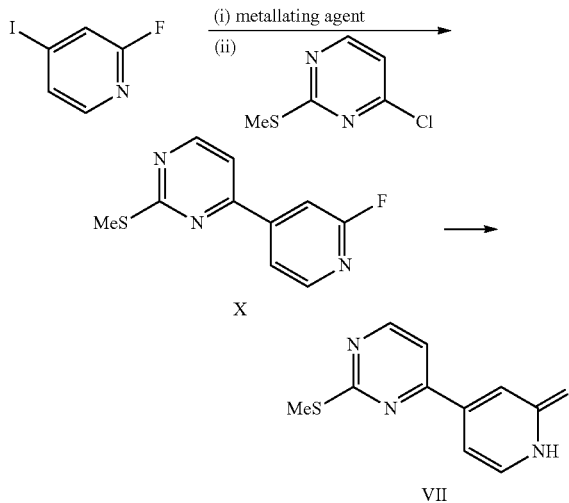

(a) contacting 2-fluoro-4-iodopyridine with a metallating agent in an aprotic organic solvent to afford an organomagnesium compound, which is reacted with 4-chloro-2(methylthio)pyrimidine in the presence of a palladium catalyst to afford 4-(2-fluoropyridin-4-yl)-2-(methylthio)pyrimidine (X);

(b) treating X with potassium tert-butoxide in THF and subsequently with an aqueous acid to afford 4-(2-(methylsulfonyl)pyrimidin-4-yl)pyridin-2(1H)-one (VII).

In embodiment 16, the present invention provides processes according to embodiment 15 wherein the palladium catalyst is (1,3-diisopropylimidazol-2-ylidene)(3-chloropyridyl)palladium(II) dichloride, the metallating agent is i-PrMgCl and LiCl, and the aprotic solvent is THF.

In embodiment 17, the present invention provides the compound (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one benzenesulfonate.

In embodiment 18, the present invention provides pharmaceutical compositions comprising (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one benzenesulfonate and a pharmaceutically acceptable excipient.

In embodiment 19, the present invention provides crystalline (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one benzenesulfonate.

In embodiment 20, the present invention provides crystalline (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one benzenesulfonate having an X-ray powder diffraction pattern comprising peaks at 6.16±0.2, 7.46±0.2, 16.36±0.2, 25.76±0.2 and 25.98±0.2 2θ

In embodiment 21, the present invention provides crystalline (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one benzenesulfonate having an X-ray powder diffraction pattern substantially as shown in FIG. 1.

In embodiment 22, the present invention provides crystalline (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one benzenesulfonate having an $^{13}$C NMR pattern substantially as shown in FIG. 19.

In embodiment 23, the present invention provides crystalline (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one benzenesulfonate having an $^{19}$F NMR pattern substantially as shown in FIG. 20.

In embodiment 24, the present invention provides crystalline (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one benzenesulfonate having an $^{13}$C NMR pattern substantially as shown in FIG. 19 and a $^{19}$F NMR pattern substantially as shown in FIG. 20.

In embodiment 25, the present invention provides crystalline (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one benzenesulfonate having an $^{19}$F NMR pattern comprising peaks at −111.1±0.4 ppm and −115.4±0.4 ppm relative to $CFCl_3$ (at 293 K).

In embodiment 26, the present invention provides crystalline (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one benzenesulfonate having an $^{13}$C NMR pattern comprising peaks at 157.7±0.2 ppm, 129.6±0.2 ppm, 125.8±0.2 ppm, and 117.0±0.2 ppm relative to tetramethylsilane (at 293 K).

In embodiment 27, the present invention provides crystalline (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one benzenesulfonate having a DSC pattern substantially as shown in FIG. 2.

In embodiment 28, the present invention provides pharmaceutical compositions comprising crystalline (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one benzenesulfonate in accordance with any one of embodiments 19 to 27 and a pharmaceutically acceptable excipient.

In embodiment 29, the present invention provides the compound (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one p-toluenesulfonic acid.

In embodiment 30, the present invention provides pharmaceutical compositions comprising (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one p-toluenesulfonic acid and a pharmaceutically acceptable excipient.

In embodiment 31, the present invention provides crystalline (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one p-toluenesulfonic acid.

In embodiment 32, the present invention provides crystalline (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one p-toluenesulfonic acid Form A.

In embodiment 33, the present invention provides crystalline (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one p-toluenesulfonic acid Form A having an X-ray powder diffraction pattern comprising peaks at. 5.76±0.2, 13.44±0.2, 15.64±0.2, 19.40±0.2 2θ.

In embodiment 34, the present invention provides crystalline (S)-1-(1-(4-chloro-3-fluorophenyl)-2-hydroxyethyl)-4-(2-((1-methyl-1H-pyrazol-5-yl)amino)pyrimidin-4-yl)

pyridin-2(1H)-one p-toluenesulfonic acid Form A having an X-ray powder diffraction pattern substantially as shown in FIG. 12.

In embodiment 35, the present invention provides crystalline (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one p-toluenesulfonic acid Form A having a DSC pattern substantially as shown in FIG. 13.

In embodiment 36, the present invention provides pharmaceutical compositions comprising crystalline (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one p-toluenesulfonic acid Form A having an X-ray powder pattern diffraction substantially in FIG. 12.

In embodiment 37, the present invention provides crystalline (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one p-toluenesulfonic acid Form B.

In embodiment 38, the present invention provides crystalline (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one p-toluenesulfonic acid Form B. having an X-ray powder diffraction pattern comprising peaks at 7.02±0.2, 16.30±0.2, 17.30±0.2, 21.86±0.2 2θ.

In embodiment 39, the present invention provides crystalline (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one p-toluenesulfonic acid Form B having an X-ray powder diffraction pattern substantially as shown in FIG. 15.

In embodiment 40, the present invention provides crystalline (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one p-toluenesulfonic acid Form B having a DSC pattern substantially as shown in FIG. 16.

In embodiment 41, the present invention provides pharmaceutical compositions comprising crystalline (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one p-toluenesulfonic acid Form B in accordance with any one of embodiments 37 to 40 and a pharmaceutically acceptable excipient.

In embodiment 42, the present invention provides the compound (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one naphthalenedisulfonic acid.

In embodiment 43, the present invention provides pharmaceutical compositions comprising (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one naphthalenedisulfonic acid and a pharmaceutically acceptable excipient.

In embodiment 44, the present invention provides crystalline (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one naphthalenedisulfonic acid.

In embodiment 45, the present invention provides crystalline (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one naphthalenedisulfonic acid Form I.

In embodiment 46, the present invention provides crystalline (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one naphthalenedisulfonic acid Form I having an X-ray powder diffraction pattern comprising peaks at 12.50±0.2, 13.86±0.2 2θ.

In embodiment 47, the present invention provides crystalline (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one naphthalenedisulfonic acid Form I having an X-ray powder diffraction pattern substantially as shown in FIG. 6.

In embodiment 48, the present invention provides crystalline (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one naphthalenedisulfonic acid Form I having a DSC pattern substantially as shown in FIG. 7.

In embodiment 49, the present invention provide pharmaceutical compositions comprising crystalline (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one naphthalenedisulfonic acid Form I in accordance with any one of embodiments 44 to 48 and a pharmaceutically acceptable excipient.

In embodiment 50, the present invention provides crystalline (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one naphthalenedisulfonic acid Form II.

In embodiment 51, the present invention provides crystalline (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one naphthalenedisulfonic acid Form II having an X-ray powder diffraction pattern comprising peaks at 12.80±0.2, 22.42±0.2, 24.92±0.2 2θ.

In embodiment 52, the present invention provides crystalline (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one naphthalenedisulfonic acid Form II having an X-ray powder diffraction pattern substantially as shown in FIG. 8.

In embodiment 53, the present invention provides crystalline (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one naphthalenedisulfonic acid Form II having a DSC pattern substantially as shown in FIG. 9.

In embodiment 54, the present invention provides pharmaceutical compositions comprising crystalline (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one naphthalenedisulfonic acid Form II having an X-ray powder pattern diffraction substantially as shown in FIG. 9.

In embodiment 55, the present invention provides amorphous (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one benzenesulfonate.

In embodiment 56, the present invention provides amorphous (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one benzenesulfonate having an X-ray powder diffraction pattern substantially as shown in FIG. 21.

In embodiment 57, the present invention provides amorphous (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one benzenesulfonate having a DSC pattern substantially as shown in FIG. 22.

In embodiment 58, the present invention provides pharmaceutical compositions comprising amorphous (S)-1-(1-(4-chloro-3-fluorophenyl)-2-hydroxyethyl)-4-(2-((1-1H-pyrazol-5-yl)amino)pyrimidin-4-yl)pyridin-2(1H)-one benzenesulfonate in accordance with any one of embodiments 55 to 57 and a pharmaceutically acceptable excipient.

BRIEF DESCRIPTION OF THE FIGURES

FIG. 22 shows the DSC analysis of VIII besylate amorphous.

DETAILED DESCRIPTION OF THE INVENTION

Figure 1:
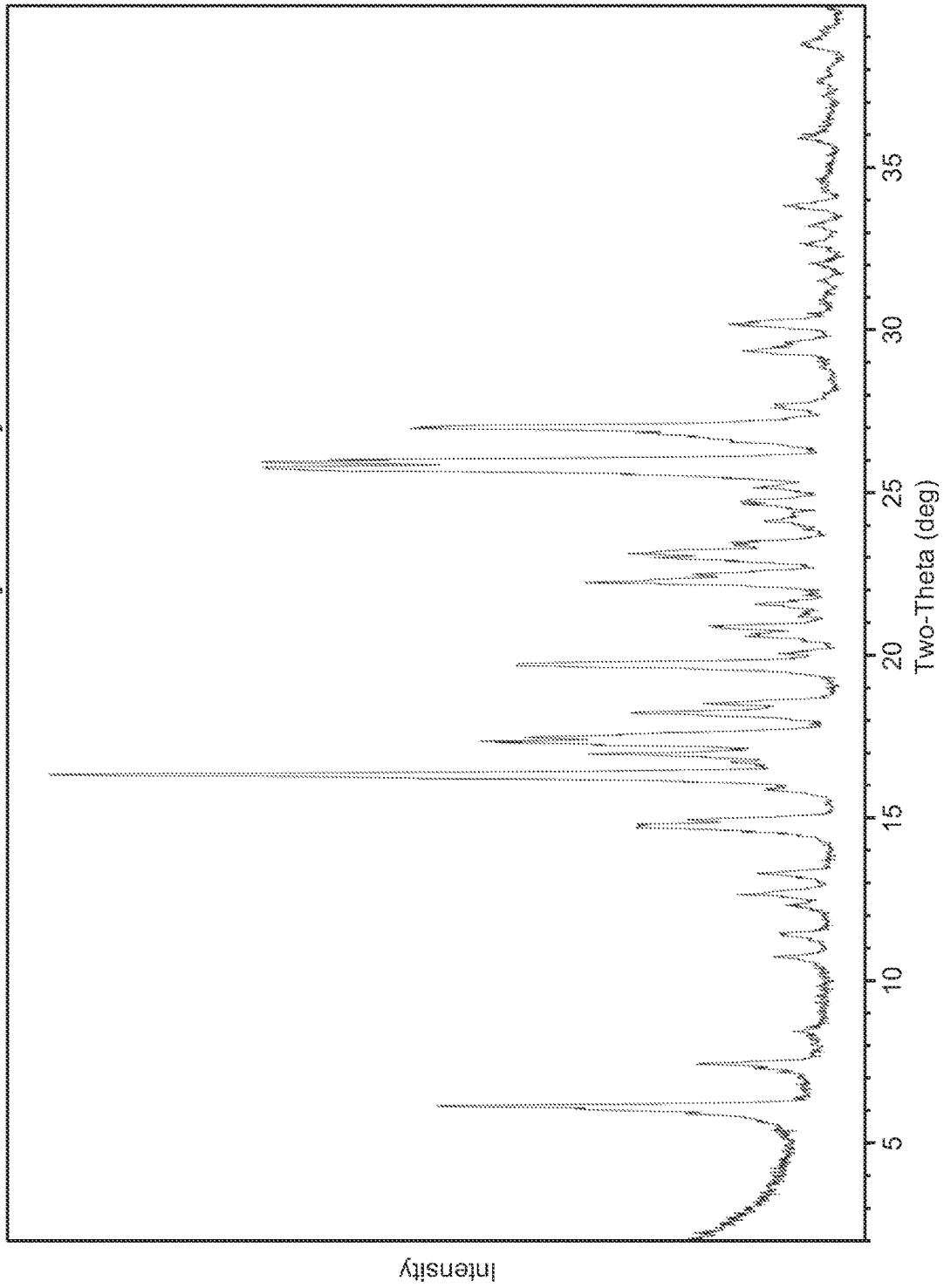
FIG. 1 shows the XRPD pattern of VIII crystalline besylate form A.
Figure 2:
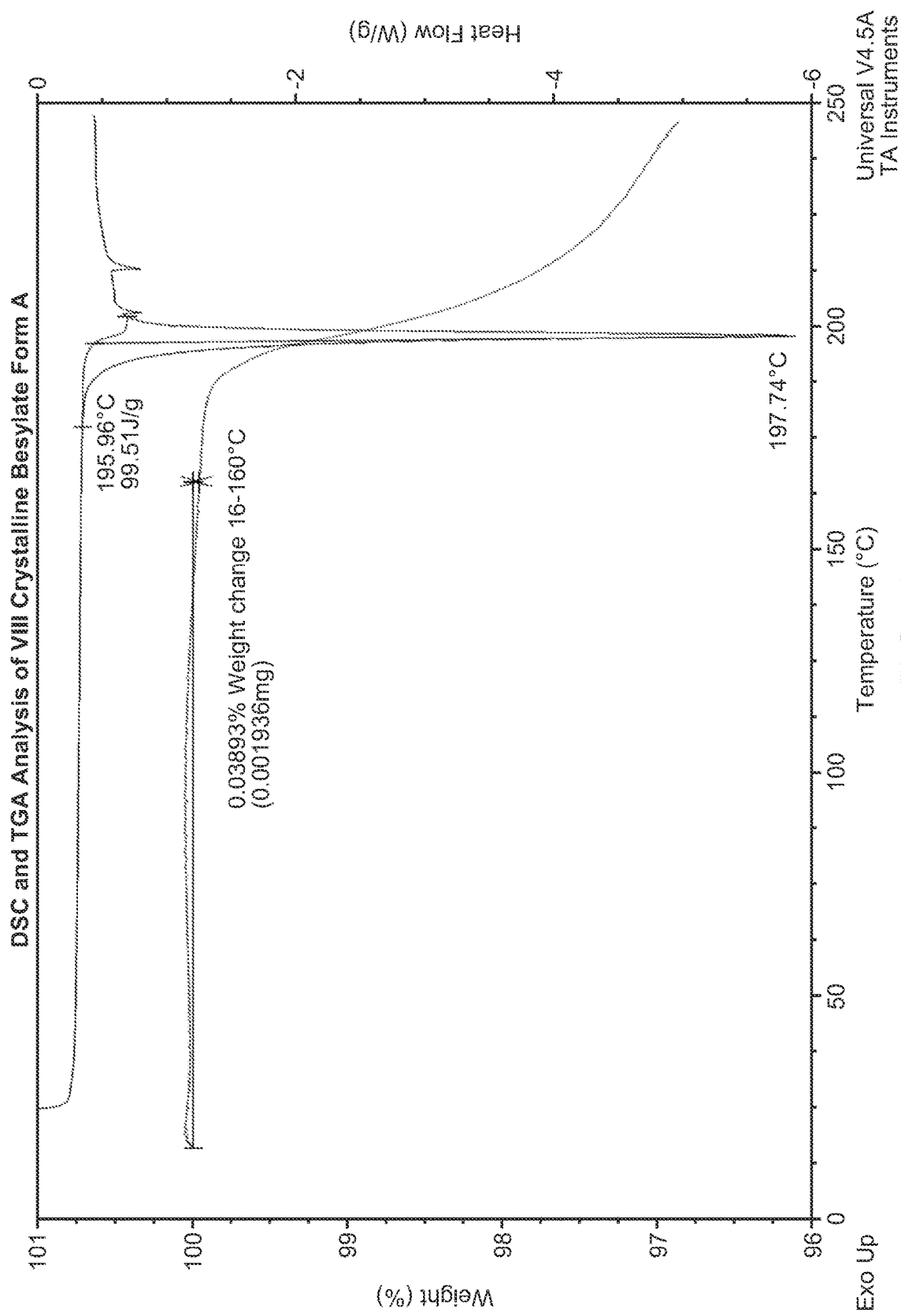
FIG. 2 shows the DSC and TGA analysis of VIII crystalline besylate form A.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. The invention is intended to cover all alternatives, modifications, and equivalents that may be included within the scope of the present invention. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components. Additionally, the words "include," "including," and "includes" when used in this specification and in the following claims are intended to specify the presence of stated features, integers, components, or steps, but they do not preclude the presence or addition of one or more other features, integers, components, steps, or groups thereof.

The term "about" when used in conjunction with hours, denotes ±5 hours. The term "about" when used in conjunction with temperatures denotes ±5 Celsius degrees. The term "about" when used in conjunction with percentages or other values, denotes ±10%.

The term "chiral" refers to molecules which have the property of non-superimposability of the mirror image partner, while the term "achiral" refers to molecules which are superimposable on their mirror image partner.

The term "isomer" refers to compounds with the same formula, but a different arrangement of atoms in the molecule and different properties.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may be separated under high resolution analytical procedures such as electrophoresis and chromatography.

The term "enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds described herein may contain asymmetric or chiral centers, and therefore exist in different stereoisomeric forms. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The present process as described herein also can be used to prepare isotopically-labeled compounds of the present invention which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention and their uses. Exemplary isotopes that can be incorporated into compounds of the invention include isotopes of hydrogen, carbon, nitrogen, oxygen, phosphorus, sulfur, fluorine, chlorine and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ or $^{125}I$. Certain isotopically-labeled compounds of the present invention (e.g., those labeled with $^{3}H$ and $^{14}C$) are useful in compound and/or substrate tissue distribution assays. Tritiated ($^{3}H$) and carbon-14 ($^{14}C$) isotopes are useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy. Isotopically labeled compounds of the present invention can generally be prepared by following procedures analogous to those disclosed in the Examples herein below, by substituting an isotopically labeled reagent for a non-isotopically labeled reagent.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "aprotic (or nonpolar) solvent means organic solvents such as diethyl ether, ligroin, pentane, hexane, cyclohexane, heptane, chloroform, benzene, toluene, dioxane, tetrahydrofuran, dichloromethane or ethyl acetate.

The term "polar aprotic solvent" refers to organic solvents such as formamide, N,N-dimethylformamide, dimethylsulfoxide, N-methylpyrrolidone or hexamthylphosphoramide.

The term "polar protic solvent" refers to organic solvents such as lower alkanols, formic acid or acetic acid.

The term "ethereal solvent" refers to solvents such as tetrahydofuran, dimethoxyethane, dioxane, or dialkyl ethers such as diethyl ether and methyl tertbutyl ether.

The term "derivative" of a compound as used herein means a compound obtainable from the original compound by a simple chemical process.

The term "protecting group" as used herein refers to a chemical group that (a) preserves a reactive group from participating in an undesirable chemical reaction; and (b) can be easily removed after protection of the reactive group is no longer required. For example, the benzyl group is a protecting group for a primary hydroxyl function.

The term "hydroxyl protecting group" or "alcohol protecting group" means a protecting group that preserves a hydroxy group that otherwise would be modified by certain chemical reactions. A hydroxyl protecting group can be an ether, an ester, or silane that can be removed easily after completion of all other reaction steps, such as a lower acyl group (e.g., the acetyl or propionyl group or a dimethyl-t-butylsilyl group), or an aralkyl group (e.g., the benzyl group, optionally substituted at the phenyl ring). The term "silyl chloride" as used herein refers to $(R^{a})_{3}SiCl$ wherein $R^{a}$ is independently in each occurrence $C_{1-6}$ alkyl or phenyl.

The term "deprotecting reagent" as used herein refers to reagents contacted with a protected chemical moiety to remove the protecting groups. Reagents and protocols for deprotection are well known and can be found in Greene and Wuts or in Harrison and Harrison (infra). One skilled in the chemical arts will appreciate that on occasion protocols must be optimized for a particular molecule and such optimization is well with the ability of one skilled in these arts.

The term "optional" or "optionally" as used herein means that the subsequently described event or circumstance may but need not occur, and that the description includes instances where the event or circumstance occurs and instances in which it does not. For example, "aryl group optionally mono- or di-substituted with an alkyl group" means that the alkyl may but need not be present, and the description includes situations where the aryl group is mono- or disubstituted with an alkyl group and situations where the aryl group is not substituted with the alkyl group.

As used herein, the term "treating," "contacting" or "reacting" when referring to a chemical reaction means to add or mix two or more reagents under appropriate conditions to produce the indicated and/or the desired product. It should be appreciated that the reaction which produces the indicated and/or the desired product may not necessarily result directly from the combination of two reagents that were initially added, i.e., there may be one or more intermediates which are produced in the mixture which ultimately leads to the formation of the indicated and/or the desired product.

The term "leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like. The term "sulfonyl chloride" refers to a compound $R^{b}S(O)_{2}Cl$ wherein $R^{b}$ is selected from $C_{1-4}$ alkyl or phenyl, optionally substituted with 1 to 3 groups independently selected from $C_{1-3}$ alkyl, halogen, nitro, cyano, $C_{1-3}$ alkoxy.

A Wittig reagent can be used to form an alkene from an aldehyde. The Wittig reagent is usually prepared from a phosphonium salt, which is in turn made by the reaction of triphenylphosphine with an alkyl halide. To form the Wittig reagent (ylide), the phosphonium salt is suspended in a solvent such as diethyl ether or THF and treated with a strong base such as phenyllithium or n-butyllithium.

The Sharpless dihydroxylation or bishydroxylation is used in the enantioselective preparation of 1,2-diols from prochiral olefins. This procedure is performed with an osmium catalyst and a stoichiometric oxidant [e.g. $K_{3}Fe(CN)_{6}$ or N-methylmorpholine oxide (NMO)]; it is carried out in a buffered solution to ensure a stable pH, since the reaction proceeds more rapidly under slightly basic conditions. Enantioselectivity is achieved through the addition of enantiomerically-enriched chiral ligands [$(DHQD)_{2}PHAL$, $(DHQ)_{2}PHAL$ or their derivatives]. These reagents are also available as stable, prepackaged mixtures (AD-mix α and AD-mix β, AD=asymmetric dihydroxylation) for either enantiopreference.

The present procedures can use the Karl Fischer method for determining trace amounts of water in a sample. This method can be abbreviated "KF."

In the methods of preparing compounds described herein, it may be advantageous to separate reaction products from one another and/or from starting materials. The desired products of each step or series of steps is separated and/or purified (hereinafter separated) to the desired degree of homogeneity by techniques common in the art. Typically, such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point and molecular weight in distillation and sublimation, presence or absence of polar functional groups in chromatography, stability of materials in acidic and basic media in multiphase extraction, and the like. One skilled in the art will apply techniques most likely to achieve the desired separation.

The present invention provides a process for the preparation of (S)-1-(1-(4-chloro-3-fluorophenyl)-2-hydroxyethyl)-4-(2-(1-methyl-1H-pyrazol-5-ylamino)pyrimidin-4-yl)pyridin-2(1H)-one (VIII) which has the structure

VIII

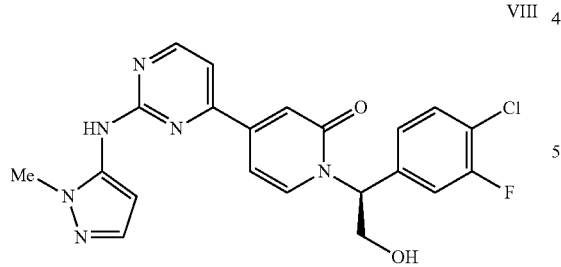

and is a potent inhibitor of ERK kinase and useful as a medicament for the treatment of cancer or other hyperproliferative disorders. Condensation of I and 1-methyl-1H-pyrazol-5-amine (XIV) in the presence of strong base affords the IX, which is readily converted to VIII by contacting the silyl ether with aqueous acid. The amorphous free base obtained can be converted to a crystalline arylsulfonic acid salt. The term "arylsulfonic acid" as used herein refers to a benzene sulfonic acid or a naphthalene mono- or disulfonic acid in which the aryl ring is optionally substituted with methyl or halogen.

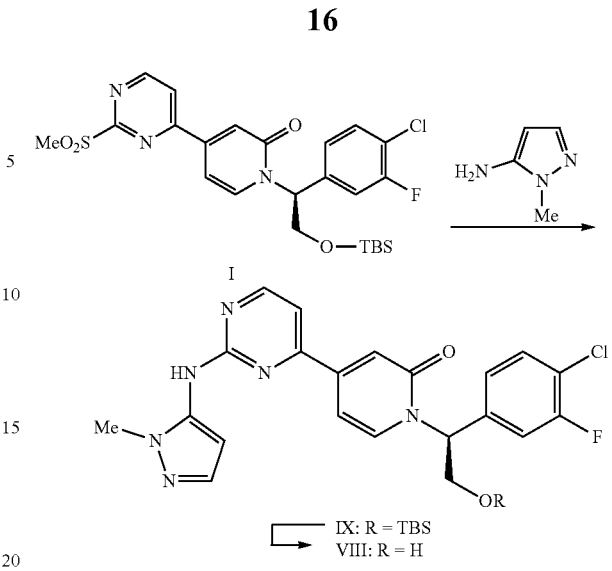

IX: R = TBS
VIII: R = H

The present invention further provides a process for the manufacture of intermediate I by first treating 4-(2-(methylthio)pyrimidin-4-yl)pyridin-2(1H)-one (VII) with strong base and alkylating the resulting compound with (R)-2-((tert-butyldimethylsilyl)oxy)-1-(4-chloro-3-fluorophenyl)ethyl methanesulfonate (VI).

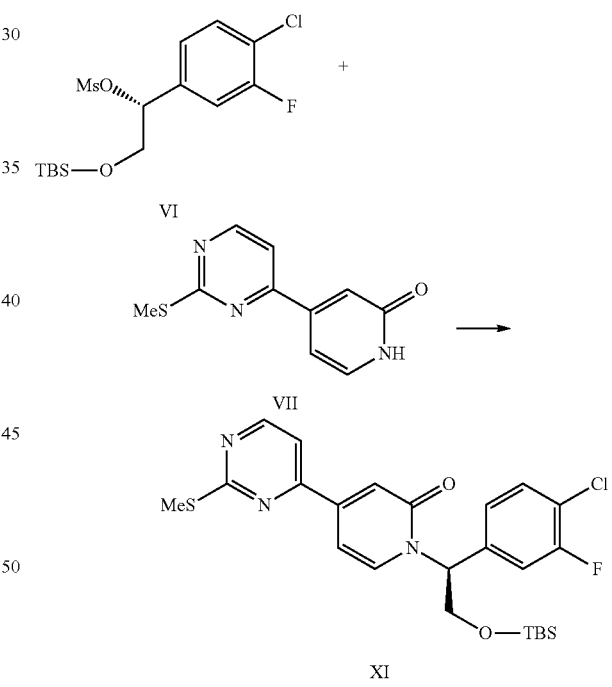

N-Alkylation of amides can be carried out under a variety of basic conditions well known to someone skilled in the art. The reaction is typically carried out in aprotic solvents such as THF, DMF, DMSO, NMP or mixtures thereof at temperatures between −78° C. and 100° C. Typically used bases are Grignard reagents, sodium hydride, potassium hydride, sodium methoxide, potassium tert-butoxide, lithium hexamethyldisilazide, sodium hexamethyldisilazide, or potassium hexamethyldisilazide. Treating VII with potassium hexamethyldisilazide in diglyme at RT allow formation of the lithium salt of VII after which the mesylate VI was introduced and the reaction heated at 90° C. for 4 h.

Oxidation of a thioether to a sulfoxide or sulfone is typically facile and numerous reagents are known that are capable of carrying out this transformation. Sulfur oxidations are commonly carried out with aqueous solution of hydrogen peroxide, $NaIO_4$, tert-butylhypochlorite, acyl nitrites, sodium perborate potassium hydrogen persulfate or peracids such as peracetic acid and meta-chloroperbenzoic acid. Typically with about one equivalent of oxidant the sulfoxide can be isolated. Exposure to two or more equivalents results in oxidation to the sulfone. Oxidation of XI with MCPBA in MTBE at ambient temperature affords I.

SCHEME B

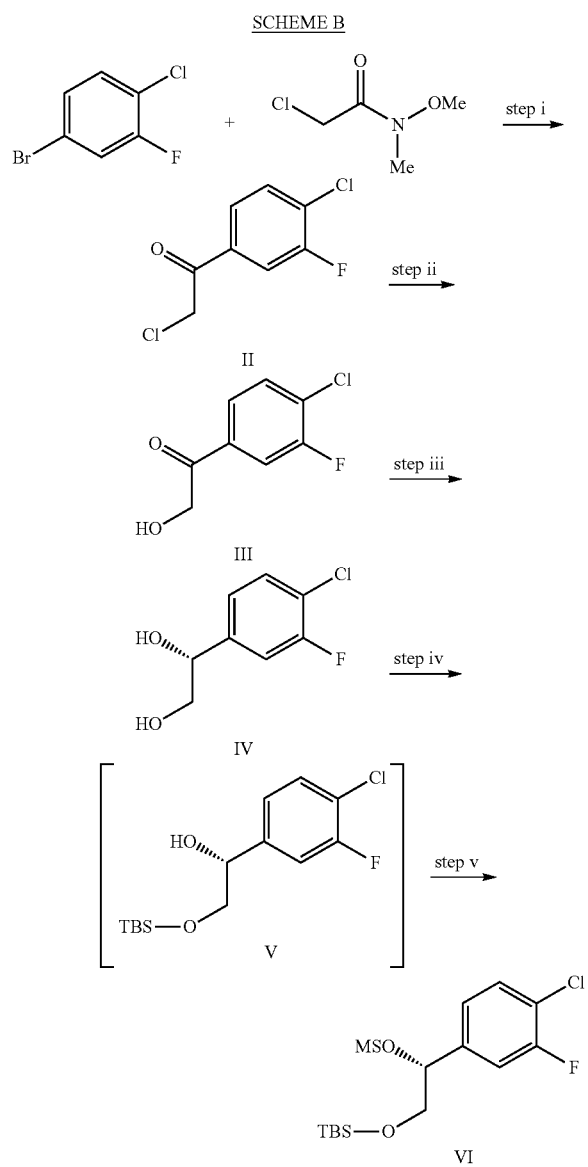

(i) i-PrMgCl, LiCl, THF; (ii) $HCO_2Na$, $HCO_2H$, $H_2O$, EtOH; (iii) GDH-105, morpholineethanesulfonic acid, $MgCl_2$, PEG6000, heptane, 1 wt% KRED-NAD-112, NAD, glucose (iv) TBSCl, DMAP, TEA, DCM, 20-25° C., 15 h; (v) MsCl, DCM, 20-25° C., 3h The mesylate VI was prepared in five steps starting from 1-bromo-4-chloro-3-fluorobenzene, which was converted to the Grignard reagent and contacted with 2-chloro-N-methoxy-N-methylacetamide to afford the ketone II. Condensation of organolithium and organomagnesium compounds with N,O-dimethylhydroxyamides affords the corresponding ketones. (S. Nahm and D. M. Weinreb, S. M. Tetrahedron Lett. 1981, 22, 3815) The Grignard reagent was formed by treating 1-bromo-4-chloro-3-fluorobenzene with isopropyl magnesium chloride in the presence of LiCl. The addition of salts is thought to increase reactivity of the Grignard reagents by promoting the breakup of polymeric aggregates known to exist in classical solutions of Grignard reagents. (A. Krasovskiy and P. Knochel, Angew. Chem. Int. Ed. 200443:3333). After the Grignard reaction was quenched with 1N HCl, the organic phase washed with water and concentrated. Sodium formate, formic acid ethanol and water were added and the mixture heated at 80-90° C. to afford the α-hydroxy ketone III.

Enzyme-catalyzed reduction of ketones frequently proceeds with high stereoselectivity, usually in the presence of NADH or NADPH as cofactor which is regenerated in situ. (J. C. Moore et al., Acc. Chem. Res, 2007 40(12):1412-19) Preferred microbial oxidoreductase enzymes found in yeasts, bacteria or from mammalian cells and the oxidoreductase can be applied in the form of the isolated enzyme(s) or whole cells, optionally in immobilized form by one of the numerous conventional methods described in literature.

The oxidized cofactor is as a rule continuously regenerated with a secondary alcohol as cosubstrate. Typical cosubstrates can be selected from 2-propanol, 2-butanol, pentan-1,4-diol, 2-pentanol, 4-methyl-2-pentanol, 2-heptanol, hexan-1,5-diol, 2-heptanol or 2-octanol, preferably 2-propanol. Preferably, the cofactor is regenerated by means of the cosubstrate at the same enzyme also catalyzing the target reaction. The acetone formed when 2-propanol is used as cosubstrate is in a further preferred embodiment continuously removed from the reaction mixture.

The cofactor can be regenerated by incorporating an additional enzyme oxidizing its natural substrate and providing the reduced cofactor. For example, secondary alcohol dehydrogenase/alcohol, glucose dehydrogenase/glucose, formate dehydrogenase/formic acid, glucose-6-phosphate dehydrogenase/glucose-6-phosphate, phosphite dehydrogenase/phosphite or hydrogenase/molecular hydrogen and the like. In addition electrochemical regeneration methods are known as well as chemical cofactor regeneration methods comprising a metal catalyst and a reducing agent are suitable. The preferred catalyst/cofactor/cosubstrate systems may vary with different ketones.

The enzymatic reduction is performed in an aqueous medium in the presence of an organic cosolvent which can be selected, for example, from glycerol, 2-propanol, diethylether, tert-butylmethylether, diisopropylether, dibutylether, ethylacetate, butylacetate, heptane, hexane or cyclohexene or mixtures thereof. The presence of an organic cosolvent is particularly advantageous as a homogenous suspension can be formed which allows simple separation of the desired alcohol of formula IV. The reaction temperature for enzymatic reductions is usually kept in a range between 1° C. and 50° C., preferably between 20° C. and 40° C.

The reaction concentration (i.e., the concentration of ketone and corresponding alcohol) is typically maintained at 1% to 25%, preferable between 10 and 20%.

In a particular embodiment of the present process the asymmetric reduction of III was catalysed by KRED-NADH-112 (Codexis Inc., Redwood City, Calif., USA) in the presence of the oxidized cofactor NAD, the recycling enzyme GDH-105 (Codexis Inc., Redwood City, Calif., USA) and the final reductant glucose affording (R)-1-(4- chloro-3-fluorophenyl)ethane-1,2-diol in 99.5% enantiomeric excess in a quantitative chemical conversion.

The final steps include the selective protection of the primary alcohol with tert-butyldimethylsilyl chloride, 4-dimethylaminopyridine (DMAP) and triethylamine (TEA) in DCM and subsequent formation of the methansulfonate ester with methansulfonyl chloride DMAP and TEA in DCM, which may be carried out sequentially in a single reaction vessel to afford (R)-2-((tert-butyldimethylsilyl)oxy)-1-(4-chloro-3-fluorophenyl)ethyl methanesulfonate (VI).

One skilled in the art will appreciate that the process can be advantageously applied other substituted bromobenzene derivatives.

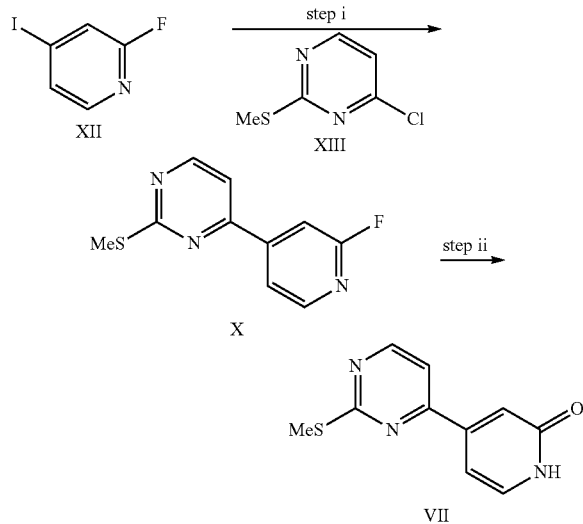

(i) 1.0% PEPPSI (i-Pr), i-PrMgCl, LiCl, THF; step (ii) (a) tert-BuOK, THF (b) 1N H₂SO₄, THF, RT 4-(2-(Methylthio)pyrimidin-4-yl)pyridin-2(1H)-one (VII) was prepared by palladium-catalyzed coupling of 4-chloro-2-thiomethylpyrimidine (XIII) and 2-fluoro-4-iodopyridine (XII). The Grignard reagent was prepared by transmetallation with i-PrMgCl in the presence of LiCl (Krasovskiy, supra) and treating the resulting heteroaryl Grignard with XIII in the presence of PEPPSI (i-Pr) ([1,3-bis(2,6-diisopropylphenyl)imidazol-2-ylidene](3-chloropyridyl)palladium(II) dichloride, CASRN 905459-27-0). Reaction of X with potassium tert-butoxide afforded 4-(2-(tert-butoxy)pyridin-4-yl)-2-(methylthio)pyrimidine, which was treated with H₂SO₄ to remove the tert-butyl group and afford VII.

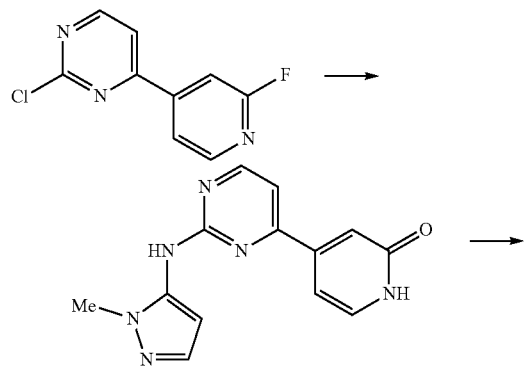

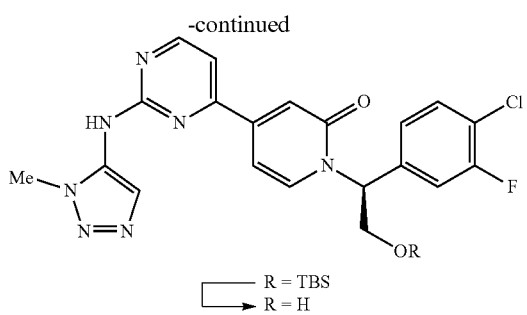

The sequence of steps can be modified without departing from the invention as disclosed herein. In a variation, a 2,4-disubstituted pyrimidine derivative, such as 2,4-dichloro-pyrimidine or 4-chloro-2-methylthiopyrimidine, is coupled with 2-fluoropyridin-4-ylboronic acid (Pd(dppf)Cl₂, K₃PO4, dioxane) to afford 2-chloro-4-(2-fluoropyridin-4-yl) pyrimidine, which is condensed with 1-methyl-1H-pyrazol-5-amine (LiHMDS, THF) and hydrolyzed to afford 4-(2-(1-methyl-1H-pyrazol-5-ylamino)pyrimidin-4-yl)pyridin-2(1H)-one which can be alkylated as described previously using two equivalents of base.

Commonly used abbreviations which may appear include: acetyl (Ac), aqueous (aq.), atmospheres (Atm), tert-butoxycarbonyl (Boc), di-tert-butyl pyrocarbonate or boc anhydride (BOC₂O), benzyl (Bn), benzotriazol-1-yloxy-tris-(dimethylamino)phosphoniumhexafluorophosphate (BOP), butyl (Bu), benzoyl (Bz), Chemical Abstracts Registration Number (CASRN), benzyloxycarbonyl (CBZ or Z), carbonyl diimidazole (CDI), dibenzylideneacetone (DBA), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), ethyl (Et), diethyl ether (Et₂O), ethyl acetate (EtOAc), ethanol (EtOH), 2-ethoxy-2H-quinoline-1-carboxylic acid ethyl ester (EEDQ), diethyl ether (Et₂O), O-(7-azabenzotriazole-1-yl)-N, N,N'N'-tetramethyluronium hexafluorophosphate acetic acid (HATU), O-(benzotriazol-1-yl)-N,N,N',N'-tetramethyluronium hexafluorophosp (HBTU), acetic acid (HOAc), 1-N-hydroxybenzotriazole (HOBt), high pressure liquid chromatography (HPLC), isopropanol (IPA), lithium hexamethyldisilazide (LiHMDS), lithium diisopropylamide (LDA), methanol (MeOH), melting point (mp), MeSO₂-(mesyl or Ms), methyl (Me), acetonitrile (MeCN), m-chloroperbenzoic acid (MCPBA), mass spectrum (ms), methyl tert-butyl ether (MTBE), N-methylmorpholine (NMM), N-methylpyrrolidone (NMP), pyridinium chlorochromate (PCC), petroleum ether (pet ether, i.e. hydrocarbons),)phenyl (Ph), propyl (Pr), iso-propyl (i-Pr), pounds per square inch (psi), bromo-tris-pyrrolidinophosphonium hexafluorophosphate (PyBrOP), pyridine (pyr), room temperature (rt or RT), satd. (saturated), tert-butymethyl ether (TBME), tert-butyldimethylsilyl or t-BuMe₂Si (TBDMS or TBS), triethylamine (TEA or Et₃N), triflate or CF₃SO₂-(Tf), trifluoroacetic acid (TFA), O-benzotriazol-1-yl-N,N,N,N-tetramethyluronium tetrafluoroborate (TBTU), thin layer chromatography (TLC), tetrahydrofuran (THF), tetramethylethylenediamine (TMEDA), trimethylsilyl or Me₃Si (TMS), 2-(trimethylsilyl)ethoxymethyl (SEM), p-toluenesulfonic acid monohydrate (TsOH or pTsOH), 4-Me—C₆H₄SO₂— or tosyl (Ts), N-urethane-N-carboxyanhydride (UNCA), 4,5-Bis(diphenylphosphino)-9,9-dimethylxanthene(Xantphos), extracellular signal-regulated kinase (ERK), tetrahydrofuran (THF), hour(s) (h), metachloroperoxybenzoic acid (MCPBA or mCPBA), nicotinamide adenine dinucleotide (NAD), nicotinamide adenine dinucleotide phosphate (NADP), 4-dimethylaminopyridine (DMAP), phenyl (Ph), methyl (Me), ethyl (Et), tert-butyl (t-Bu), tert-butyldimethylsilyl chloride (TBSCl), mesyl (Ms), ethyl acetate (EtOAc), gas chromatography (GC), methylethyl ketone (MEK), high pressure liquid chromatography (HPLC), X-ray powder diffraction (XRPD), nuclear magnetic resonance (NMR), glass transition temperature (TG), thermogravimetric analysis (TGA), differential scanning calorimetry (DSC), polytetrafluoroethylene (PTFE). Conventional nomenclature including the prefixes normal (n), iso (i-), secondary (sec-), tertiary (tert- or -t) and neo- have their customary meaning when used with an alkyl moiety. (J. Rigaudy and D. P. Klesney, Nomenclature in Organic Chemistry, IUPAC 1979 Pergamon Press, Oxford.).

In order to illustrate the invention, the following examples are included. However, it is to be understood that these examples do not limit the invention and are only meant to suggest a method of practicing the invention. Persons skilled in the art will recognize that the chemical procedures described herein may be adapted to suit available equipment and circumstances. Additionally, reagents such as the selection of leaving groups, activating groups, protecting groups and reagents, such as strong bases and palladium catalysts may be altered without deviating from the disclosed invention.

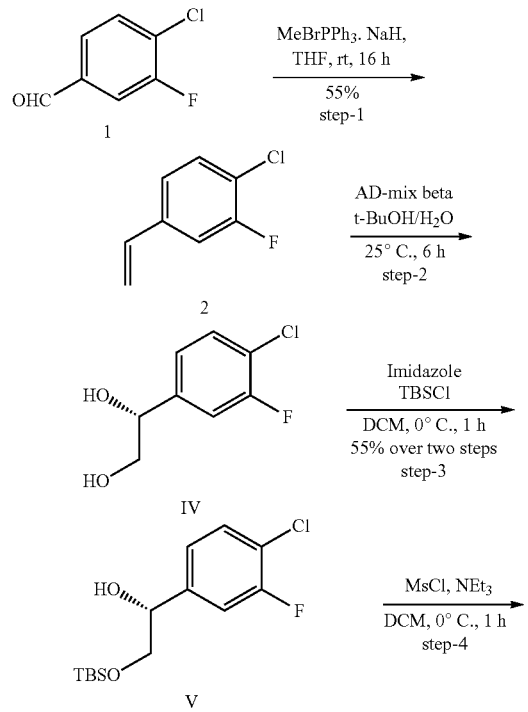

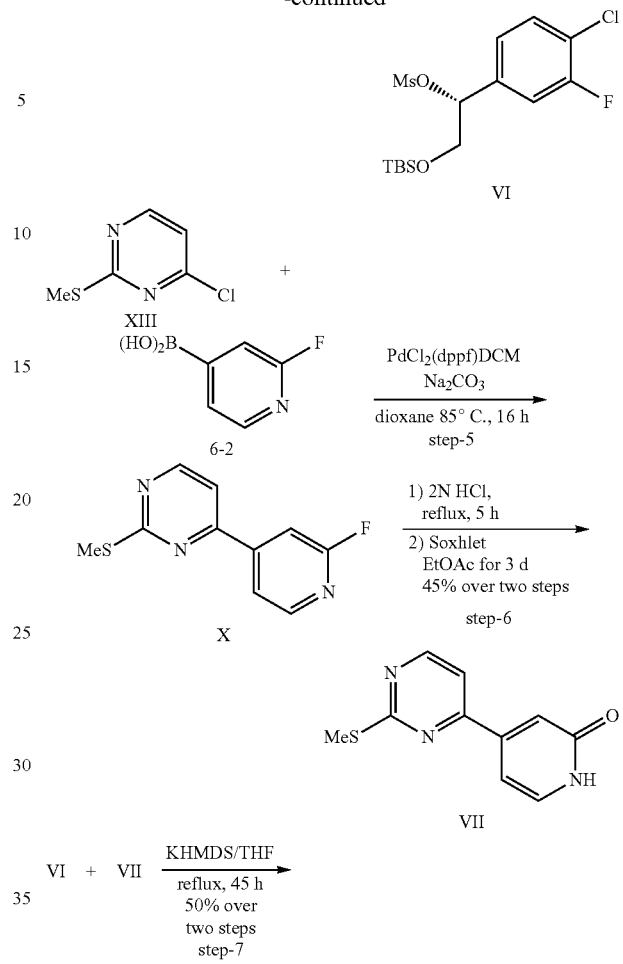

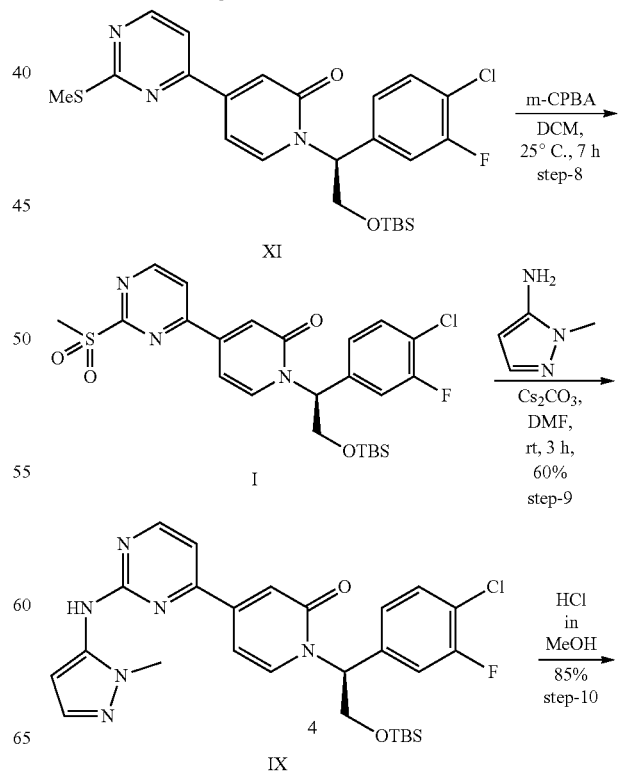

-continued

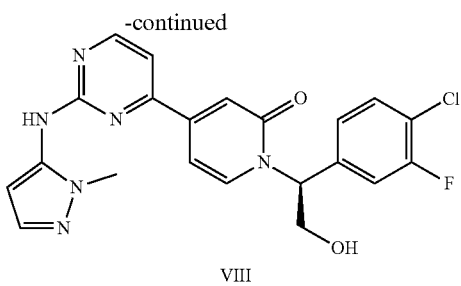

VIII

The original synthetic process involves an eight step linear synthesis (10 steps overall) from three commercially available materials, 4-chloro-3-fluorobenzaldehyde 1, 4-chloro-2-(methylthio)pyrimidine XIII and (2-fluoropyridin-4-yl)boronic acid 6-2 (Scheme 1). Wittig reaction of 1 produced olefin intermediate 2 in 55% yield. Asymmetric Sharpless dihydroxylation of styrene followed by a selective mono-protection of diol IV with TBSCl afforded intermediate V in 55% yield over two steps. One of the intermediates VI was obtained through a mesylation of secondary alcohol. On the other hand, pyridone intermediate VII was synthesized through a Suzuki cross coupling between XIII and 6-2, followed by a hydrolysis with aqueous HCl solution. A purification of VII by a Soxhlet extraction with EtOAc over 3 days was required to ensure a good purity of 6 and a reasonable conversion in the subsequent reaction. Sn2 displacement of VI and VII was able to afford intermediate XI in 50% yield over 2 steps from intermediate V. An oxidation with m-CPBA afforded sulfone intermediate I that underwent a SnAr displacement with commercially available aminopyrazole, 2-methylpyrazole-3-amine, to generate intermediate IX in 60% yield. Finally an acid promoted TBS deprotection afforded free base VIII in 85% yield. The chemistry of this route suffered from low yields in several individual steps. A lot of tedious purifications such as distillation, flash chromatography and Soxhlet extraction were needed due to fairly complicate reaction profiles. Use of less desirable solvents and reagents such as dichloromethane, sodium hydride and osmium oxide also deterred the chemistry from being scaled up.

Scheme 2. Improved Process To I

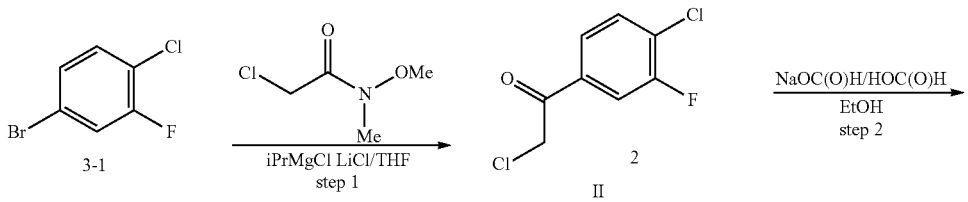

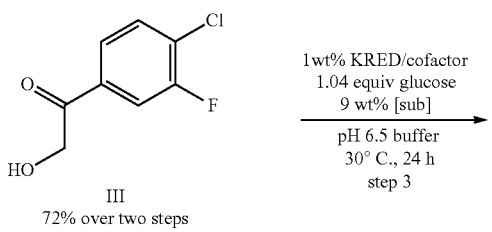

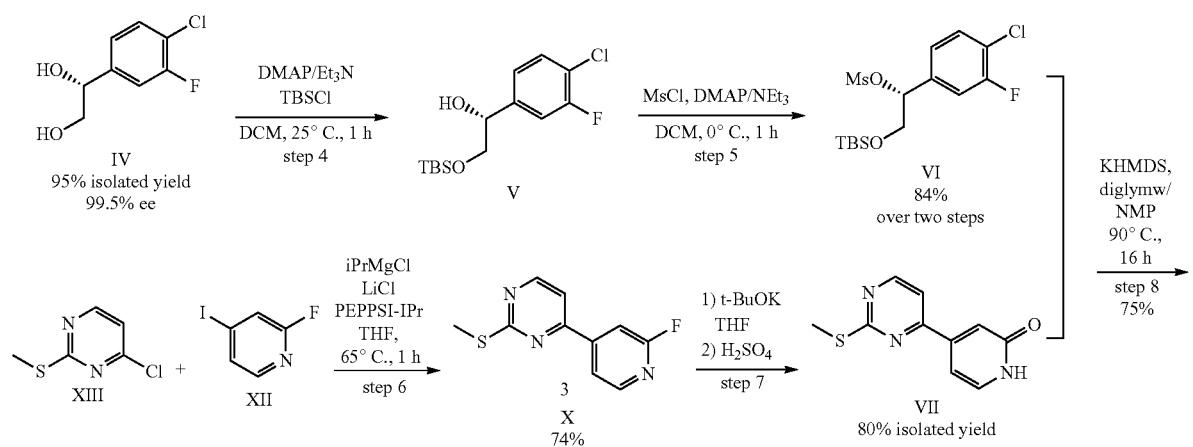

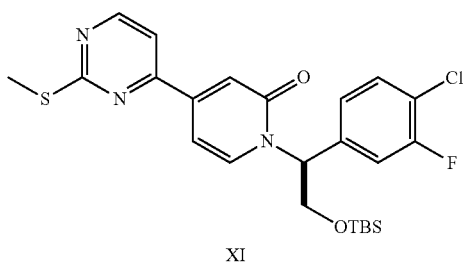

XI

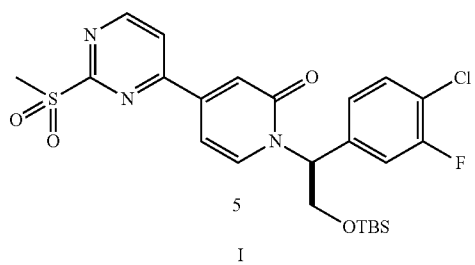

I

An improved route to synthesize I was identified. Hydroxyl ketone intermediate III was obtained in 72% yield over two steps. Grignard exchange of commercially available arene 3-1 and subsequent nucleophilic addition to Weinreb amide generated intermediate II that was then hydrolyzed to give III. An enzymatic asymmetric ketone reduction afforded the same diol intermediate IV with high yield and high enantioselectivity. The same processes of selective TBS protection and mesylation were used to produce intermediate VI. The synthesis of pyridone VII was improved. Kumada coupling catalyzed by PEPPSI-IPr was used to generate intermediate X in a higher yield and better purity profile. A two-step sequence of hydrolysis was applied to avoid formation of corrosive HF during the original process. A displacement of fluoride with t-BuOK in THF followed removal of tert-butyl group under acidic condition afforded pyridone intermediate VII in 80% yield. Sn2 displacement was improved by using different base and solvent compared to the original route. Intermediate XI was oxidized under the same conditions to give I.

Example 1

2-((tert-Butyldimethylsilyl)oxy)-1-(4-chloro-3-fluorophenyl)ethyl methanesulfonate

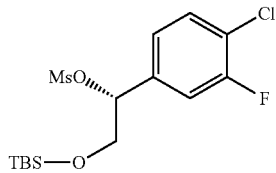

VI

Step 1: 4-bromo-1-chloro-2-fluorobenzene (64 kg) and dry toluene (170 kg) were charged to the 2000 L steel reaction vessel under nitrogen. The reactor was evacuated and backfilled with $N_2$ for three times, and cooled to between −10 and 5° C. under nitrogen atmosphere. To the solution was added dropwise i-PrMgCl—LiCl (280 kg, 1.3 M in THF) at between −10 and 10° C. The reaction was stirred for a further 15 to 30 min at between −10 and 10° C. and then warmed to about 20 to 25° C. over 1 h. The reaction mixture was stirred for another 6 h stir to complete the exchange. The resulting solution was cooled to between −50 and −40° C. A solution of 2-chloro-N-methoxy-N-methyl-acetamide (44.5 kg) in dry toluene (289 kg) was added dropwise to the above solution at while maintaining the temperature between −50 and −30° C. The reaction mixture was warmed to between 20 and 25° C. over 1 h and then stirred for 3 h to complete the reaction. The reaction was quenched by addition of 1N aq. HCl (8081 g) at a temperature between −5 and 15° C. The aqueous layer was separated and organic layer was filtered through a pad of diatomaceous earth. The organic layer was washed with 10% aq. NaCl solution (320 kg) twice, then concentrated to about 300 L to obtain 1-(4-chloro-3-fluorophenyl)-2-chloroethanone(51.8 kg, 81.9% yield) as product in toluene.

Step 2: The solution of II (51.7 kg) in toluene was concentrated and solvent exchanged to EtOH to afford a suspension of II in EtOH (326 kg). A solution of $HCOONa \cdot 2H_2O$ (54.8 kg) and HCOOH (44.5 kg) in water (414 kg) was added at a temperature between 15 and 35° C. under a nitrogen atmosphere. The resulting mixture was heated to reflux and stirred for 4 to 5 h. The solution was cooled to between 20 and 30° C. after over 95% conversion occurred. Water (450 kg) was added dropwise at between 10 and 30° C. for over 2 h. The resulting suspension was cooled to between −10 and −3° C. and the cooled solution stirred for 1 to 2 h. The solid was filtered and the filter cake washed with water (400 kg) to remove the residual HCOONa and HCOOH. The 1-(4-chloro-3-fluorophenyl)-2-hydroxyethanone obtained was suspended in EtOAc (41 kg) and n-heptane (64 kg), then warmed to between 45 and 50° C., stirred for 2 h, then cooled to between −2 and 5° C. for over 2 h and stirred at this temperature for 2 h. The solids were filtered and dried in vacuo at between 40 and 50° C. for 12 h to afford the product as white solid (40.0 kg, 99.3% purity, 84.5% yield).

Step 3: A 500 L reactor under nitrogen was charged with purified water (150 kg), 4-morpholineethanesulfonic acid (0.90 kg), anhydrous $MgCl_2$ (0.030 kg), n-heptane (37 kg), 1-(4-chloro-3-fluorophenyl)-2-hydroxyethanone (30 kg), D-(+)-glucose monohydrate (34.8 kg) and PEG 6000 (30.0 kg). The pH of the solution was adjusted to between 6.5 and 7.0 with 1N aq. NaOH at between 28 and 32° C. The cofactor recycling enzyme, glucose dehydrogenase GDH-105 (0.300 kg) (Codexis Inc., Redwood City, Calif., USA), the cofactor nicotinamide adenine dinucleotide NAD(0.300 kg) (Roche) and the oxidoreductase KRED-NADH-112 (0.300 kg) (Codexis Inc., Redwood City, Calif., USA) were added. The resulting suspension was stirred at between 29 and 31° C. for 10 to 12 h while adjusting the pH to maintain the reaction mixture pH between 6.5 and 7.0 by addition of 1N aq. NaOH (160 kg). The pH of the reaction mixture was adjusted to between 1 and 2 by addition of 49% $H_2SO_4$ (20 kg) to quench the reaction. EtOAc (271 kg) was added and the mixture was stirred at between 20 and 30° C. for 10-15 min then filtered through a pad of diatomaceous earth. The filter cake was washed with EtOAc (122 kg). The combined organic layers were separated and aqueous layer was extracted with EtOAc (150 kg). Water (237 kg) was added to the combined organic layers. The pH of the mixture was adjusted to between 7.0 and 8.0 by addition of solid $NaHCO_3$. The organic layer was separated, concentrated and then diluted with DCM to afford (R)-1-(4-chloro-3-fluorophenyl)ethane-1,2-diol (30.9 kg, yield 100%) as product in DCM.

Step 4: A 1000 L reactor under nitrogen was charged with (R)-1-(4-chloro-3-fluorophenyl)ethane-1,2-diol (29.5 kg) and dry DCM (390 kg). The solution was cooled to between −5 and 0° C. tert-Butylchlorodimethylsilane (25.1 kg) was added in portions while maintaining the temperature between −5 and 2° C. A solution of DMAP (0.95 kg) and TEA (41.0 kg) in dry DCM (122 kg) was added dropwise to above solution at between −5 and 2° C. The reaction solution was stirred for 1 h, then warmed to between 20 and 25° C. and stirred for 16 h. The solution of (R)-2-((tert-butyldimethylsilyl)oxy)-1-(4-chloro-3-fluorophenyl)ethanol was recooled to between −10 and −5° C. A solution of methanesulfonyl chloride (19.55 kg) in dry DCM (122 kg) was added dropwise to the above solution of while maintaining the temperature between −10 and 0° C. The reaction solution was stirred at between −10 and 0° C. for 20 to 30 min, and then warmed to between 0 and 5° C. for over 1 h, and stirred. The reaction solution was washed with water (210 kg), followed by 5% aq. citric acid (210 kg), 2% aq. NaHCO$_3$ (210 kg) and finally water (2×210 kg). The resulting DCM solution was dried (Na$_2$SO$_4$), filtered and concentrated in vacuo below 15° C. (jacket temperature below 35° C.) to afford (R)-2-((tert-butyldimethylsily)oxy)-1-(4-chloro-3-fluorophenyl)ethyl methanesulfonate (49.5 kg, 83.5% yield, KarlFischer=0.01%) as product in DCM.

Example 2

4-(2-(methylthio)pyrimidin-4-yl)pyridin-2(1H)-one

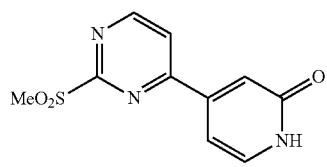

(VII)

Step 1: A 1000 L reactor was charged with 2-fluoro-4-iodopyridine (82.2 kg) and dry THF (205 kg). The reactor was evacuated and backfilled with N$_2$ three times then cooled to between −30 and −20° C. To the solution was added dropwise i-PrMgCl.LiCl (319 kg, 1.3 M in THF). The reaction was warmed to between −20 and −10° C. and stirred for 1.5 h to complete the transmetallation.

A 2000 L reactor was charged with 4-chloro-2-methylthiopyrimidine (45.6 kg), dry THF (205 kg) and [1,3-bis(2,6-diisopropylphenyl) imidazol-2-ylidene] (3-chloropyridyl) palladium(II) dichloride (PEPPSI™-IPr, 1.850 kg). The 2000 L reactor was evacuated and backfilled with N$_2$ three times and heated to between 55 and 57° C. To the reactor was added over 0.5 to 1 h, the solution of (2-fluoropyridin-4-yl)magnesium chloride while maintaining the temperature between 50 and 62° C. The resulting reaction mixture was stirred at between 50 and 62° C. for a further 2 h. The reaction mixture was cooled to between 5 and 25° C. while the reaction was quenched with water (273 kg). The pH of the mixture was adjusted to 8 to 9 by adding solid citric acid monohydrate (7.3 kg). The organic layer was separated, washed with 12.5% aqNaCl (228 kg) and concentrated in vacuo below 50° C. to afford 4-(2-fluoropyridin-4-yl)-2-(methylthio)pyrimidine (38.3 kg, 61% yield) as product in THF.

Step 2: The solution of 4-(2-fluoropyridin-4-yl)-2-(methylthio)pyrimidine (38.2 kg) in THF was concentrated and co-evaporated with THF to remove residual water. The suspension was filtered through a pad of diatomaceous earth to remove inorganic salts. To the resulting solution in THF (510 kg) was added tert-BuOK(39.7 kg) in portions while maintaining the temperature between 15 and 25° C. The mixture was warmed to between 20 and 25° C. and stirred for 5 h. NaHCO$_3$ (14.9 kg) added charged and then a citric acid solution (5 kg) in THF (15 kg) was added to adjust the pH to between 8 and 9. Water (230 kg) was added. The mixture was filtered and the filter cake was washed with THF (100 kg). The combined THF solutions were washed with 12.5% aqueous NaCl (320 kg) and concentrated to about 380 L to afford a solution of 4-(2-(tert-butoxy)pyridin-4-yl)-2-(methylthio)pyrimidine in THF.

To the THF solution cooled to between 15 and 30° C. was added 1N H$_2$SO$_4$ aq. solution (311 kg). The mixture was stirred at this temperature for 4 h. MTBE (280 kg) was charged and the pH of reaction solution was adjusted to 14 with 30% aqueous NaOH (120 kg). The aqueous layer was separated and the organic phase filtered to remove inorganic salts. The obtained aqueous layer was washed with MTBE (2×280 kg). 2-MeTHF (1630 kg) and i-PrOH (180 kg) were added to the aqueous solution. The pH was then adjusted to 8 slowly with conc. HCl (19 kg). An organic layer separated and aqueous layer was extracted with 2-MeTHF (305 kg). The combined 2-MeTHF extracts were washed with water (300 kg) and concentrated to about 100 L. MTBE (230 kg) was added and stirred at 20-30° C. for 0.5 h. The solid was filtered and slurried in a mixture solvent of 2-MeTHF (68 kg) and MTBE (230 kg). The suspension was stirred at 35-50° C. for 3 h, and then cooled to 0 to 10° C. and stirred at a further 2 h. The solid was filtered and dried in vacuo at between 50 and 62° C. for 20 h to afford product 4-(2-(methylthio)pyrimidin-4-yl)pyridin-2(1H)-one as brown solid (33.55 kg, 89.6% assay, 79.4% yield).

Example 3

(S)-1-(2-((tert-Butyldimethylsilyl)oxy)-1-(4-chloro-3-fluorophenyl)ethyl)-4-(2-(methylthio)pyrimidin-4-yl)pyridin-2(1H)-one (XI)

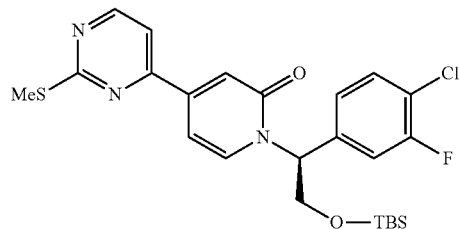

XI

Step 1: The THF was co-evaporated from the THF solution of 4-(2-(methylthio)pyrimidin-4-yl)pyridin-2(1H)-one (25.5 kg) to remove residual water. Dry bis-(2-methoxyethyl)ether (75 kg) was added. A solution of KHMDS (131 kg, 1 M in THF) was added dropwise while maintaining the temperature between 25 and 40° C. The mixture was heated to between 75 and 80° C. and stirred for 30 to 40 min. The resulting mixture was cooled to between 20 and 30° C. under nitrogen atmosphere. A solution of (R)-2-((tert-butyldimethylsilyl)oxy)-1-(4-chloro-3-fluorophenyl)ethyl methanesulfonate (47.6 kg) in THF (50 kg) was added over 30 to 60 min while maintaining the temperature between 20 and 40° C. The reaction solution was warmed to between 80 and 85° C. and stirred for 7 h. The solution was cooled to between 5 and 15° C. and water (155 kg) was added. The pH of the solution was adjusted to 7.5 with 30% aqueous citric acid (30 kg). EtOAc (460 kg) was added and the mixture was stirred for 20 min. The organic layer was separated and washed with 12.5% aqueous NaCl (510 kg). The combined aqueous layers were extracted with EtOAc (115 kg). The ethyl acetate layers were concentrated to about 360 L to afford (S)-1-(2-((tert-butyldimethylsilyl)oxy)-1-(4-chloro-3-fluorophenyl)ethyl)-4-(2-(methylthio)pyrimidin-4-yl)pyridin-2(1H)-one (44.6 kg, 75.7% yield) as product in EtOAc.

Step 2: To a solution of (S)-1-(2-((tert-butyldimethylsilyl)oxy)-1-(4-chloro-3-fluorophenyl)ethyl)-4-(2-(methylthio)pyrimidin-4-yl)pyridin-2(1H)-one (44.6 kg) in EtOAc (401 kg, 10 vol) cooled to between 5 and 10° C. was added in portions MCPBA (58 kg). The reaction mixture was added to a solution of NaHCO$_3$ (48.7 kg) in water (304 kg) at a temperature between 10 and −20° C. A solution of Na$_2$S$_2$O$_3$ (15 kg) in water (150 kg) was added dropwise to consume residual MCBPA. The organic layer was separated and aqueous layer was extracted with EtOAc (130 kg). The combined organic layers were washed with water (301 kg), concentrated and solvent exchanged to DCM to afford (S)-1-(2-((tert-butyldimethylsilyl)oxy)-1-(4-chloro-3-fluorophenyl)ethyl)-4-(2-(methylsulfonyl)pyrimidin-4-yl)pyridin-2(1H)-one (45.0 kg, 94.9% yield) as product in DCM. The DCM solution was concentrated to about 100 L, filtered through a pad of SiO$_2$ (60 kg) and eluted with an EtOAc/DCM gradient (0, 25 and 50% EtOAc). The fractions were combined and concentrated to get the product which was re-slurried with (acetone: n-heptane=1:3 v/v) four times to afford the final product (31.94 kg, 71% yield).

Example 4

(S)-1-(1-(4-Chloro-3-fluorophenyl)-2-hydroxyethyl)-4-(2-((1-methyl-1H-pyrazol-5-yl)amino)pyrimidin-4-yl)pyridin-2(1H)-one, benzenesulfonate salt (VIIIb)

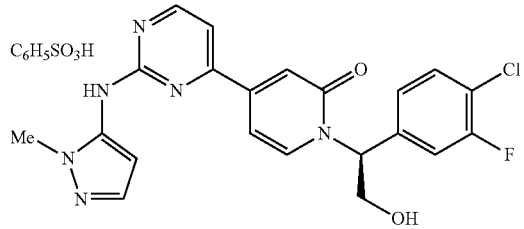

VIIIb

Step 1: A clean 100 L cylindrical reaction vessel was charged with THF (13 kg) then (S)-1-(2-((tert-butyldimethylsilyl)oxy)-1-(4-chloro-3-fluorophenyl)ethyl)-4-(2-(methylsulfonyl)pyrimidin-4-yl)pyridin-2(1H)-one (I, 5 kg) and 1-methyl-1H-pyrazol-5-amine (1.1 kg) were added sequentially with medium agitation followed by THF (18 kg). The mixture was cooled to −35° C. and to the resulting thin slurry was added slowly a THF solution of LiHMDS (17.4 kg, 1.0 M) at a rate that maintained the internal temperature below −25° C. After the addition was completed, the reaction was held between −35 and −25° C. for 20 min and monitored by HPLC. If the HPLC result indicated ≤98.5% conversion, additional LiHMDS (0.34 kg, 1.0 M, 0.05 mol %) was added slowly at −35° C. The reaction was quenched slowly at the same temperature with H$_3$PO$_4$ solution (4.4 kg of 85% H$_3$PO$_4$ and 15 kg of water) and the internal temperature was kept below 30° C. The reaction was diluted with EtOAc (18 kg) and the phases separated, the organic layer was washed with H$_3$PO$_4$ solution (1.1 kg of 85% H$_3$PO$_4$ and 12 kg of water) followed by a second H$_3$PO$_4$ wash (0.55 kg of 85% H$_3$PO$_4$ and 12 kg of water). If 1-methyl-1H-pyrazol-5-remained, the organic layer was washed again with H$_3$PO$_4$ solution (0.55 kg of 85% H$_3$PO$_4$ and 12 kg of water). Finally the organic layer was washed sequentially with water (20 kg) and a NaCl and NaHCO$_3$ solution (2 kg of NaCl, 0.35 kg of NaHCO$_3$ and 10 kg of water). After the phase separation, residue water in organic solution was removed through an azeotropic distillation with EtOAc to ≤0.5% (by KF) and then solution was concentrated to 20-30 L under a vacuum below 50° C. The solvent was then swapped to MeOH using 35 kg of MeOH and then concentrated to between 20 and 30 L for the next step.

Step 2: To the methanolic (S)-1-(2-((tert-butyldimethylsilyl)oxy)-1-(4-chloro-3-fluorophenyl)ethyl)-4-(2-((1-methyl-1H-pyrazol-5-yl)amino)pyrimidin-4-yl)pyridin-2(1H)-one (IX) solution in MeOH was added HCl (10.7 kg, 1.25 M in MeOH) at RT. It was slightly exothermic. After the addition was completed, the reaction was heated to 45° C. If the reaction was incomplete after 14 to 16 h, additional HCl (1 kg, 1.25 M in MeOH) was added and agitation at 45° C. was continued for 2 h. The reaction was equipped with a distillation setup with acid scrubber. The reaction was concentrated to between 20 and 30 L under a vacuum below 50° C. To the resulting solution was added MeOH (35 kg) and the reaction was concentrated to 20 to 30 L again under a vacuum below 50° C. The solvent was then switched to EtOAc using 40 kg of EtOAc. The solvent ratio was monitored by Headspace GC and the solvent swap continued until it was less than ⅕. The solution was concentrated to between 20 and 30 L under a vacuum below 50° C. After the solution was cooled below 30° C., aqueous NaHCO$_3$ (1.2 kg of NaHCO$_3$ and 20 kg of water) was added slowly with a medium agitation and followed by EtOAc (40 kg). The organic layer was washed with water (2×10 kg) then concentrated to 20-30 L under a vacuum below 50° C. The solvent was then switched to MEK using 35 kg of MEK. The residue MeOH was monitored by Headspace GC and the solvent swap continued until the MeOH was <0.3%. The solution containing (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one (VIII) was concentrated to 20 to 30 L under a vacuum below 50° C. for the next step.

Step 3: The solution of VIII in MEK was transferred to a second 100 L cylindrical reaction vessel through a 1 μm line filter. In a separate container was prepared benzenesulfonic acid solution (1.3 kg of benzenesulfonic acid, 1.4 kg of water and 4.4 kg of MEK). The filtered VIII solution was heated to 75° C. and to the resulting solution was added 0.7 kg of the benzenesulfonic acid solution through a 1 μm line filter. The clear solution was seeded with crystalline benzenesulfonic acid salt of VIII (0.425 kg) as a slurry in MEK (0.025 kg of VIIIb crystalline seed and 0.4 kg of MEK) which produced a thin slurry. The remaining benzenesulfonic acid solution was then added through a 1 μm line filter in 2 h. After addition, the slurry was heated at 75° C. for additional 1 h and then cooled to 18° C. in a minimum of 3 h. The resulting thick slurry was agitated at 20° C. for 14 to 16 h. The solid was filtered using an Aurora dryer. The mother liquor was assayed by HPLC (about 0.3% loss). The solid was then washed with 1 μm line filtered 15.8 kg of MEK and water solution (0.8 kg of water and 15 kg of MEK) and followed by 1 μm line filtered 30 kg of MEK. Washes were assayed by HPLC (<1% loss). The wet cake was dried under a vacuum and a nitrogen sweep at a jacket temperature of 45° C. for a minimum 12 h to afford the benzenesulfonic acid salt of VIII, which is labeled VIIIb.

Additional Examples

Step 1:

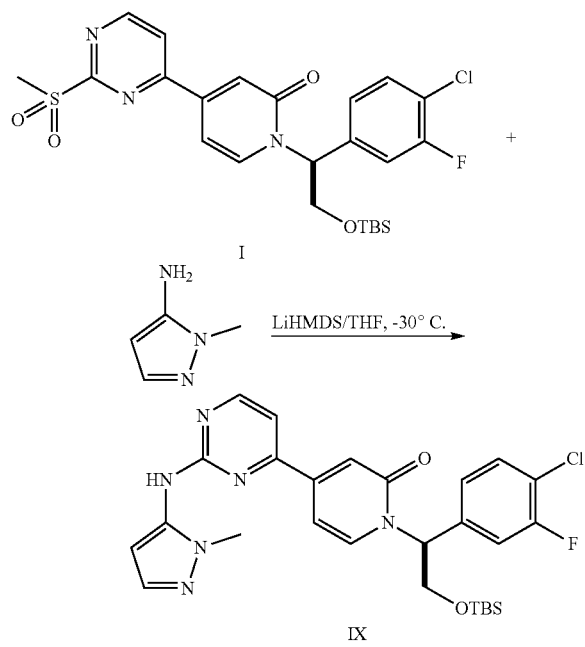

To a clean 100 L cylindrical reaction vessel was charged 13 kg of THF first. With a medium agitation, 5.0 kg of I and 1.1 kg of 1-methyl-1H-pyrazol-5-amine was charged sequentially and followed by the rest of THF (18 kg). At −35° C. to the resulting thin slurry was added 17.4 kg of LiHMDS (1.0 mol/L) in THF slowly and the internal temperature was remained below −25° C. After addition, the reaction was held between −35 and −25° C. for 20 min. The reaction was monitored by HPLC. If the HPLC result indicated ≤98.5% conversion, additional 0.34 kg (0.05 mol %) of LiHMDS (1.0 mol/L) in THF was charged slowly at −35° C. Otherwise, the reaction was quenched at the same temperature with 19.4 kg of $H_3PO_4$ solution (4.4 kg of 85% $H_3PO_4$ and 15 kg of water) slowly and the internal temperature was remained below 30° C. The reaction was diluted with 18 kg of EtOAc. After the phase separation, the organic layer was washed with 13.1 kg of $H_3PO_4$ solution (1.1 kg of 85% $H_3PO_4$ and 12 kg of water) and then with 12.6 kg of $H_3PO_4$ solution (0.55 kg of 85% $H_3PO_4$ and 12 kg of water). The organic layer was assayed for the 1-methyl-1H-pyrazol-5-amine level by HPLC. If the HPLC result indicated ≥20 μg/mL of 1-methyl-1H-pyrazol-5-amine, the organic layer needed an additional wash with 12.6 kg of $H_3PO_4$ solution (0.55 kg of 85% $H_3PO_4$ and 12 kg of water). Otherwise, the organic layer was washed with 20 kg of water. The organic layer was assayed again for the 1-methyl-1H-pyrazol-5-amine level. If the HPLC result indicated ≥2 μg/mL of 1-methyl-1H-pyrazol-5-amine, the organic layer needed an additional wash with 20 kg of water. Otherwise, the organic layer was washed with 12.4 kg of NaCl and $NaHCO_3$ solution (2 kg of NaCl, 0.35 kg of $NaHCO_3$ and 10 kg of water). After the phase separation, residue water in organic solution was removed through an azeotropic distillation with EtOAc to ≤0.5% (by KF) and then the solution was concentrated to 20 to 30 L under a vacuum below 50° C. The solvent was then swapped to MeOH using 35 kg of MeOH and then concentrated to 20 to 30 L for the next step.

Step 2:

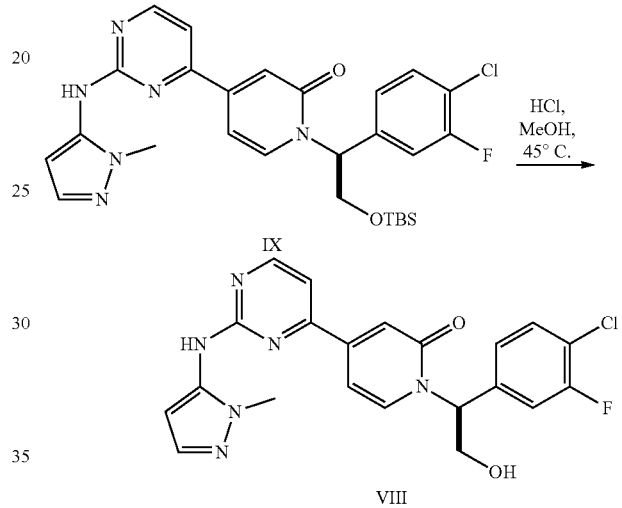

To the IX solution in MeOH from the last step was charged 10.7 kg of HCl (1.25 M in MeOH) at the ambient temperature. It was observed slightly exothermic. After addition, the reaction was heated to 45° C. After 14-16 h, the reaction was monitored by HPLC. If the HPLC result indicated the conversion was ≤98%, an additional 1 kg of HCl (1.25 M in MeOH) was charged and the reaction was agitated at 45° C. for additional 2 h. Otherwise, the reaction was equipped with a distillation setup with acid scrubber. The reaction was concentrated to 20 to 30 L under a vacuum below 50° C. To the resulting solution was charged 35 kg of MeOH and the reaction was concentrated to 20 to 30 L again under a vacuum below 50° C. The solvent was then switched to EtOAc using 40 kg of EtOAc. The solvent ratio was monitored by Headspace GC. If the ratio of MeOH/EtOAc was greater than ⅕, the solvent swap should be continued. Otherwise, the solution was concentrated to 20 to 30 L under a vacuum below 50° C. After the solution was cooled below 30° C., 21.2 kg of $NaHCO_3$ solution (1.2 kg of $NaHCO_3$ and 20 kg of water) was charged slowly with a medium agitation and followed by 40 kg of EtOAc. After the phase separation, the organic layer was washed with 2×10 kg of water. The organic layer was concentrated to 20 to 30 L under a vacuum below 50° C. The solvent was then switched to MEK using 35 kg of MEK. The residue MeOH was monitored by Headspace GC. If the level of MeOH was ≥0.3%, the solvent swap should be continued. Otherwise, the solution was concentrated to 20 to 30 L under a vacuum below 50° C. for the next step.

Step 3:

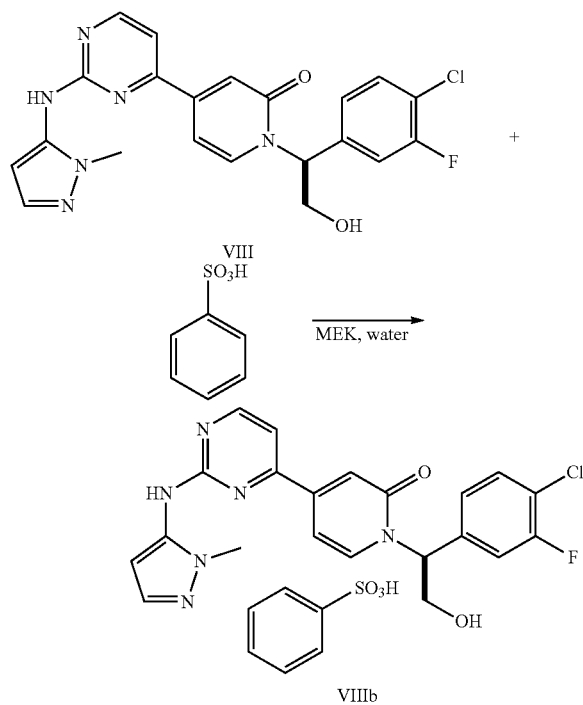

The VIII solution in MEK from the last step was transferred to a second 100 L cylindrical reaction vessel through a 3 μm line filter. In a separated container was prepared 7.1 kg of benzenesulfonic acid solution (1.3 kg of benzenesulfonic acid, 1.4 kg of water and 4.4 kg of MEK). The filtered G02584994 solution was heated to 75° C. and to the resulting solution was charged 0.7 kg of benzenesulfonic acid solution (10%) through a 3 μm line filter. To the clear solution was charged 0.425 kg of VIIIb crystalline seed slurry in MEK (0.025 kg of VIIIb crystalline seed and 0.4 kg of MEK). This resulted in a thin slurry. The rest of benzenesulfonic acid solution was then charged through a 3 μm line filter in 2 h. After addition, the slurry was heated at 75° C. for additional 1 h and then cooled to 20° C. in a minimum of 3 h. The resulting thick slurry was agitated at 20° C. for 14-16 h. Solid was filtered using a filter dryer. Mother liquor was assayed by HPLC (about 3% loss). Solid was then washed with 3 μm line filtered 15.8 kg of MEK and water solution (0.8 kg of water and 15 kg of MEK) and followed by 3 μm line filtered 30 kg of MEK. Washes were assayed by HPLC (<1% loss). The wet cake was dried under a vacuum and the nitrogen sweep at a jacket temperature of 45° C. for a minimum 12 h.

Recrystallization

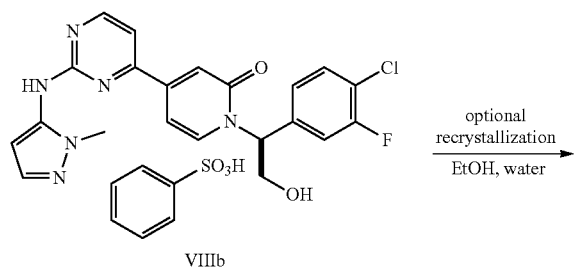

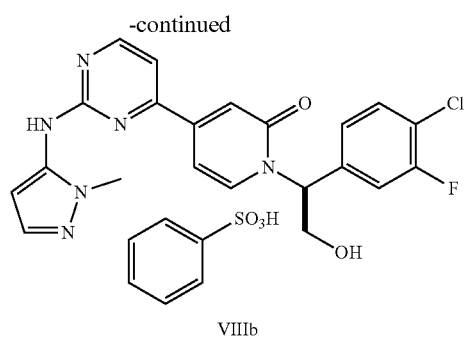

To a clean 100 L cylindrical reaction vessel was charged 16 kg of EtOH first. With a medium agitation, 3.5 kg of VIIIb was charged and then followed by the rest of EtOH (8.5 kg). The thick slurry was heated to 78° C. and water (~1.1 kg) was charge until a clear solution was obtained. The hot solution was filtered through a 3 μm line filter to a second clean 100 L cylindrical reaction vessel. The temperature dropped to 55-60° C. and the solution remained clear. To the resulting solution was charged with 0.298 kg of VIIIb crystalline seed slurry in EtOH (0.018 kg of VIIIb crystalline seed and 0.28 kg of EtOH). The thick slurry was concentrated to 20 to 30 L at 60° C. under a vacuum and then cooled 20° C. in 3 h. The resulting slurry was agitated at 20° C. for 14 to 16 h. Solid was filtered using a filter dryer. The mother liquor was assayed by HPLC (about 10% loss). Solid was then washed with 3 μm line filtered 11.1 kg of EtOH and water solution (0.56 kg of water and 11 kg of EtOH) and followed by 3 μm line filtered 21 kg of MEK. Washes were assayed by HPLC (3% loss). The wet cake was dried under a vacuum and the nitrogen sweep at a jacket temperature of 45° C. for a minimum 12 h.

An additional synthetic process is set forth below.

Step 1:

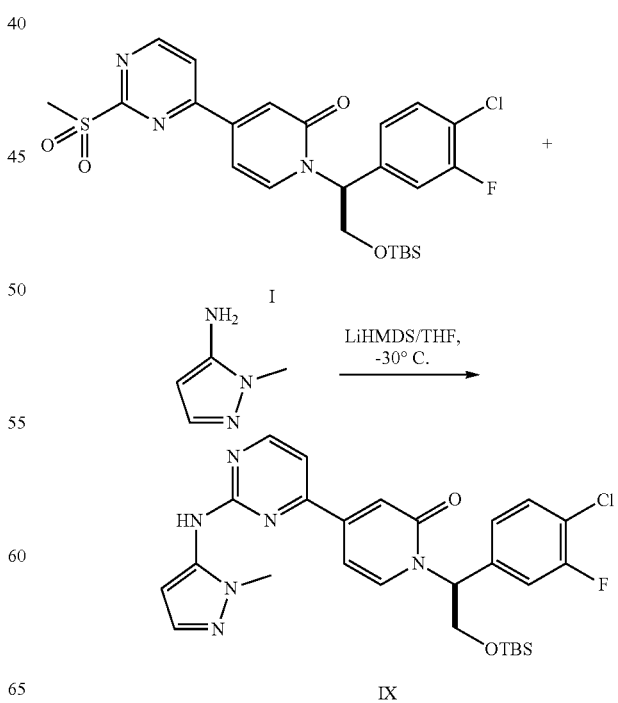

To a clean 100 L cylindrical reaction vessel was charged 18 kg of THF first. With a medium agitation, 4.2 kg of I and 0.91 kg of 1-methyl-1H-pyrazol-5-amine was charged sequentially and followed by the rest of THF (21 kg). At −40° C. to the resulting thin slurry was added 14.9 kg of LiHMDS (1.0 mol/L) in THF slowly and the internal temperature was remained below −30° C. After addition, the reaction was held between −35 and −40° C. for 20 min. The reaction was monitored by HPLC. The HPLC result indicated 99.1% conversion. The reaction was quenched at the same temperature with 16.7 kg of H$_3$PO$_4$ solution (3.7 kg of 85% H$_3$PO$_4$ and 13 kg of water) slowly and the internal temperature was remained below 30° C. The reaction was diluted with 17 kg of EtOAc. After the phase separation, the organic layer was washed with 13.1 kg of H$_3$PO$_4$ solution (1.1 kg of 85% H$_3$PO$_4$ and 12 kg of water) and then with 10.5 kg of H$_3$PO$_4$ solution (0.46 kg of 85% H$_3$PO$_4$ and 10 kg of water). The organic layer was assayed for the 1-methyl-1H-pyrazol-5-amine level by HPLC. The HPLC result indicated 2 µg/mL of 1-methyl-1H-pyrazol-5-amine. The organic layer was washed with 15.8 kg of NaCl solution (0.3 kg of NaCl and 15.5 kg of water). The organic layer was assayed again for the G02586778 level. The HPLC result indicated 0.5 µg/mL of 1-methyl-1H-pyrazol-5-amine. The organic layer was washed with 10.3 kg of NaCl and NaHCO$_3$ solution (1.7 kg of NaCl, 0.6 kg of NaHCO$_3$ and 8 kg of water). After the phase separation, residue water in organic solution was removed through an azeotropic distillation with EtOAc to ≤0.5% (by KF) and then the solution was concentrated to 20 to 30 L under a vacuum below 50° C. The solvent was then swapped to MeOH using 30 kg of MeOH and then concentrated to 20 to 30 L for the next step.

Step 2:

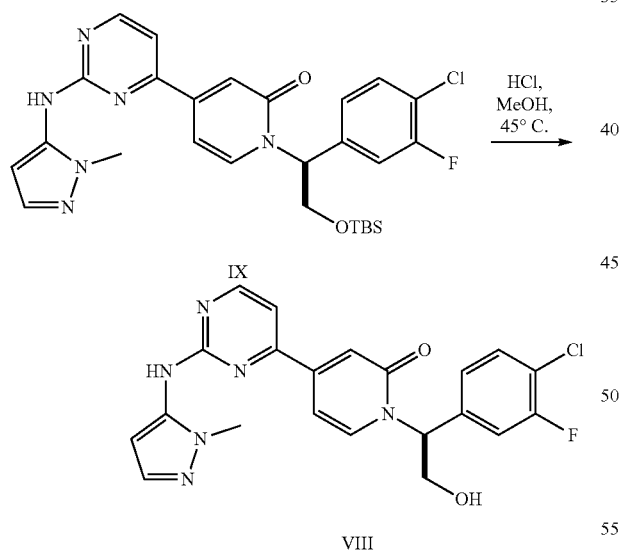

To the IX solution in MeOH from the last step was charged 9.0 kg of HCl (1.25 M in MeOH) at the ambient temperature. It was observed slightly exothermic. After addition, the reaction was heated to 45° C. After 16 h, the reaction was monitored by HPLC. The HPLC result indicated the conversion was 99.4%. The reaction was equipped with a distillation setup. The reaction was concentrated to 20 L under a vacuum below 50° C. To the resulting solution was charged 35 kg of MeOH and the reaction was concentrated to 20 L again under a vacuum below 50° C. The solvent was then switched to EtOAc using 40 kg of EtOAc. The solvent ratio was monitored by Headspace GC. If the ratio of MeOH/EtOAc was greater than ⅕, the solvent swap should be continued. Otherwise, the solution was concentrated to 20 L under a vacuum below 50° C. After the solution was cooled below 30° C., 18 kg of NaHCO$_3$ solution (1 kg of NaHCO$_3$ and 17 kg of water) was charged slowly with a medium agitation and followed by 34 kg of EtOAc. After the phase separation, the organic layer was washed with 2×8 kg of water. The organic layer was concentrated to 20 L under a vacuum below 50° C. The solvent was then switched to MEK using 35 kg of MEK. The residue MeOH was monitored by Headspace GC. If the level of MeOH was ≥0.3%, the solvent swap should be continued. Otherwise, the solution was concentrated to 20 L under a vacuum below 50° C. for the next step.

Step 3:

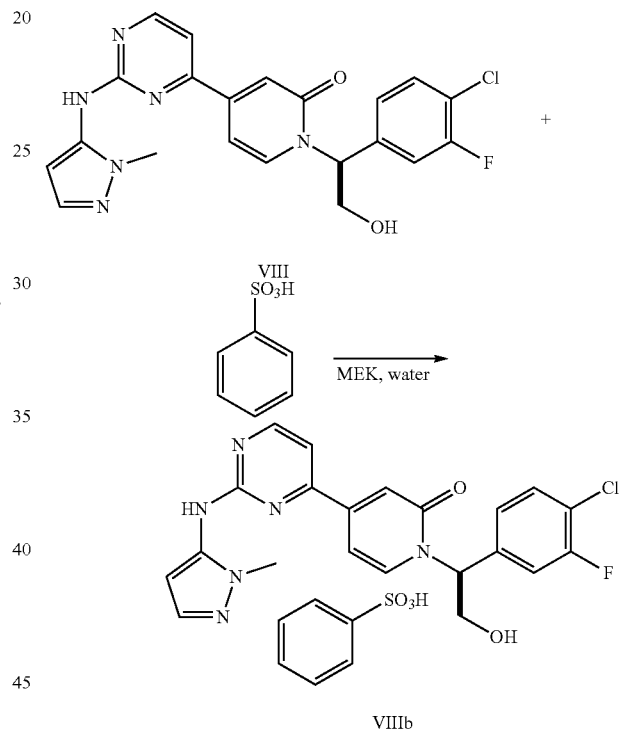

The VIII solution in MEK from the last step was transferred to a second 100 L cylindrical reaction vessel through a 1 µm polish filter. In a separated container was prepared 6.0 kg of benzenesulfonic acid solution (1.1 kg of benzenesulfonic acid, 1.2 kg of water and 3.7 kg of MEK). The filtered solution was heated to 75° C. and to the resulting solution was charged 0.6 kg of benzenesulfonic acid solution (10%) through a 1 µm line filter. To the clear solution was charged 0.36 kg of VIIIb crystalline seed slurry in MEK (0.021 kg of VIIIb crystalline seed and 0.34 kg of MEK). This resulted in a thin slurry. The rest of benzenesulfonic acid solution was then charged through a 1 µm line filter in 2 h. After addition, the slurry was heated at 75° C. for additional 1 h and then cooled to 18° C. in a minimum of 3 h. The resulting thick slurry was agitated at 18° C. for 14-16 h. Solid was filtered using an Aurora dryer. Solid was then washed with 1 µm line filtered 8.15 kg of MEK and water solution (0.35 kg of water and 7.8 kg of MEK) and followed by 1 µm line filtered 12 kg of MEK.

Recrystallization

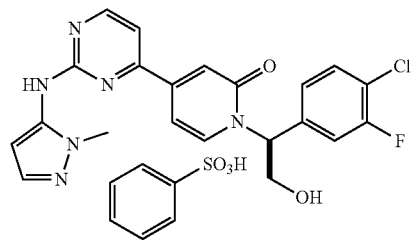

VIIIb

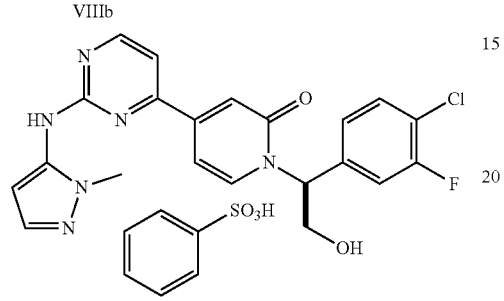

VIIIb

To a clean 100 L cylindrical reaction vessel was charged 21 kg of EtOH first. With a medium agitation, 3.5 kg of VIIIb was charged and then followed by the rest of EtOH (9 kg). The thick slurry was heated to 78° C. and water (1.2 kg) was charge until a clear solution was obtained. The hot solution was filtered through a 1 μm line filter to a second clean 100 L cylindrical reaction vessel. The temperature dropped to 69° C. and the solution remained clear. To the resulting solution was charged with 0.37 kg of VIIIb crystalline seed slurry in EtOH (0.018 kg of VIIIb crystalline seed and 0.35 kg of EtOH). The thin slurry was concentrated to 20 L at 60-70° C. under a vacuum and then cooled 18° C. in 3 h. The resulting slurry was agitated at 18° C. for 14-16 h. Solid was filtered using a filter dryer. Solid was then washed with 1 μm line filtered 8.6 kg of EtOH and water solution (0.4 kg of water and 8.2 kg of EtOH). The solution was introduced in two equal portions. The solid was then washed by 1 μm line filtered 6.7 kg of MEK. The wet cake was dried under a vacuum and the nitrogen sweep at a jacket temperature of 35-40° C. for a minimum 12 h.

Alternative Synthetic Route (Steps 1 to 10 Below)

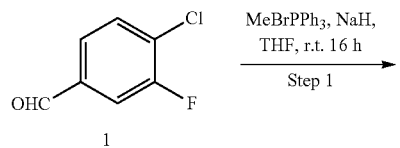

1

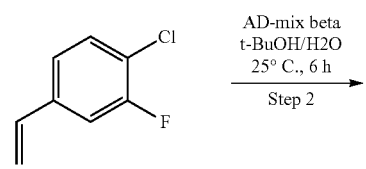

2

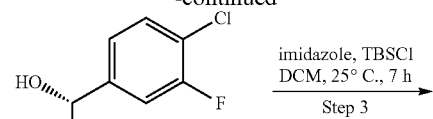

IV

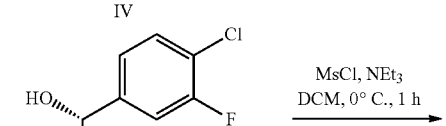

V

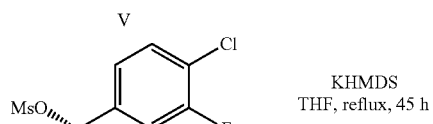

VII

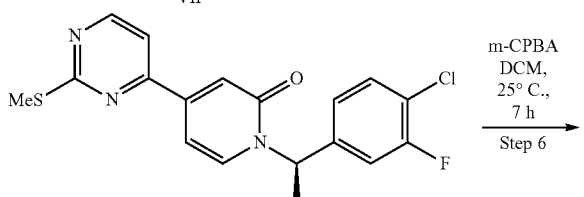

XI

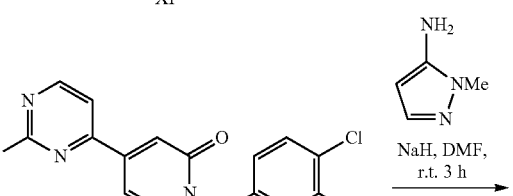

I

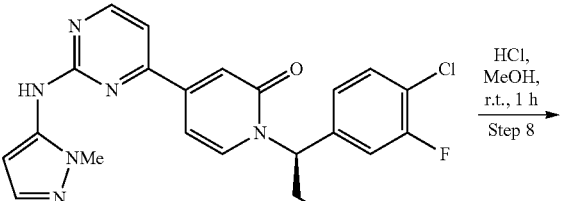

IX

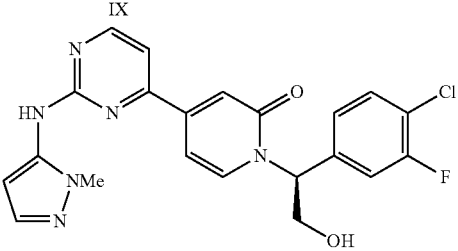

VIII

-continued

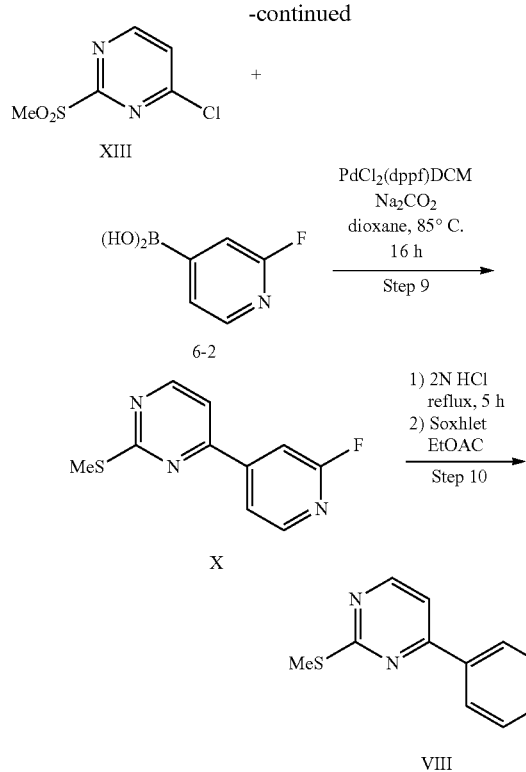

Step 1:

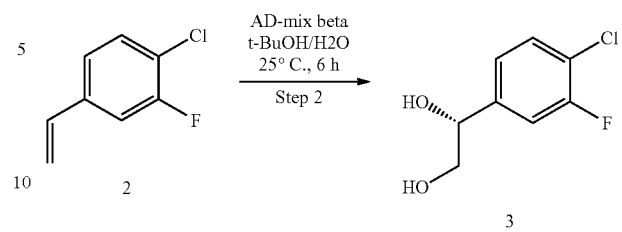

Procedure:
1. Charge compound 1 and MeBrPPh₃ to a four-necked jacketed flask with a paddle stirrer under N₂
2. Charge THF (5.0V., KF<0.02%) to the flask (Note: V is the volume of solution to mass of limited reagent or L/Kg)
3. Stir the suspension at 0° C.
4. Add the NaH (60% suspended in mineral oil) portion-wise to the flask at 0° C.
5. Stir at 0° C. for 30 min
6. Heat to 30° C. and stir for 6 hrs
7. Cool to 0° C.
8. Charge PE (petroleum ether) (5.0V.) to the flask
9. Add the crystal seed of TPPO (triphenylphospine oxide) (1 to about 5% wt of total TPPO) to the flask
10. Stir at −10° C. for 2 hrs
11. Filter, and wash the cake with PE (5.0V.)
12. Concentrate the filtrate to dryness
13. Purification of the product by distillation under reduced pressure affords 2 as colorless oil Step 2:

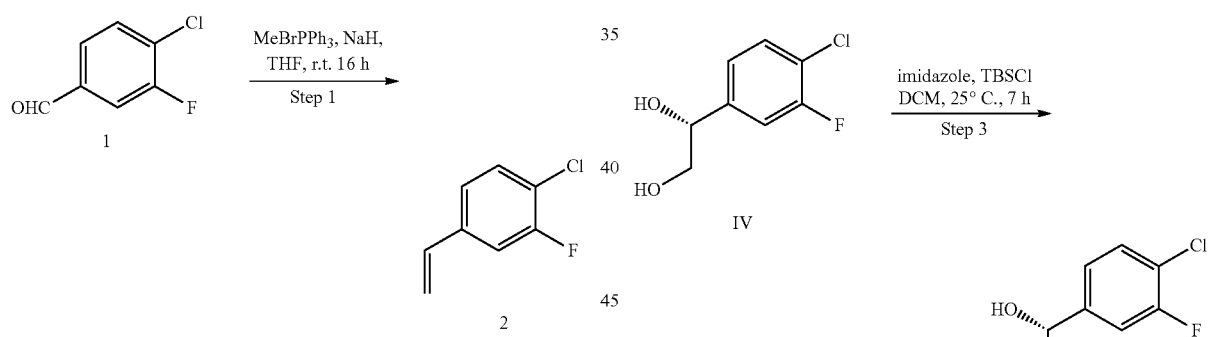

Procedure:
1. Add (DHQD)2PHAL, Na₂CO₃, K₂Fe(CN)₆, K₂OsO₂(OH)₄ into a flask under N₂ (Ad-mix beta, Aldrich, St. Louis, Mo.).
2. Cool to 0° C.
3. Add tBuOH (5V) and H₂O (5V)
4. Add 2
5. Stir the mixture at 0° C. for 6 h
6. Cool to 0° C.
7. Add Na₂SO₃ to quench the reaction
8. Stir at 0° C. for 2 h
9. Filter and wash the cake with EA (ethyl acetate)
10. Separate the organic layer
11. Filter and concentrate to dryness Step 3:

Procedure:
1. Add IV (1 eq.) and DCM (5V) to a flask under N₂
2. Cool to 0° C.
3. Add DMAP (0.1 eq.), then TEA (1.5 eq.)
4. Add TBSCl (1.05 eq.) dropwise at 0° C.
5. Stir the mixture at 0° C. for 1 h
6. Add water to quench the reaction
7. Separate the layers
8. Dry the organic layer over Na₂SO₄
9. Filter
10. Concentrate the filtrate to dryness
11. Use for next step directly Step 4:

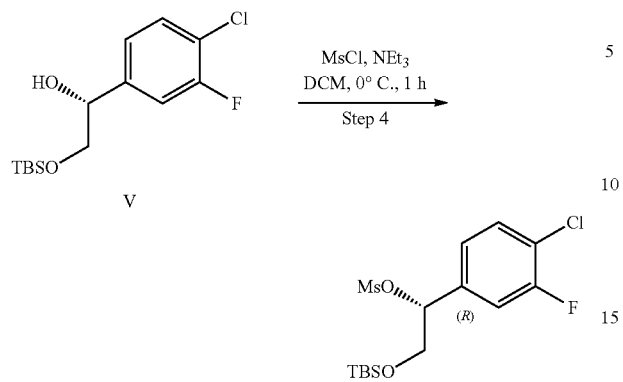

Procedure:
1. Add V (1.0 eq.) and DCM (5V) into a flask under N₂.
2. Cool to 0° C.
3. Add TEA (1.51 eq.)
4. Add MsCl (1.05 eq.) dropwise at 0° C.
5. Stir the mixture at rt for 1 h
6. Add DCM to dilute the mixture for better stirring
7. Add water to quench the reaction
8. Separate the layers
9. Wash the organic layer with NaHCO₃
10. Dry over Na₂SO₄
11. Filter and concentrate the filtrate to dryness
12. Used for next step directly Step 5:

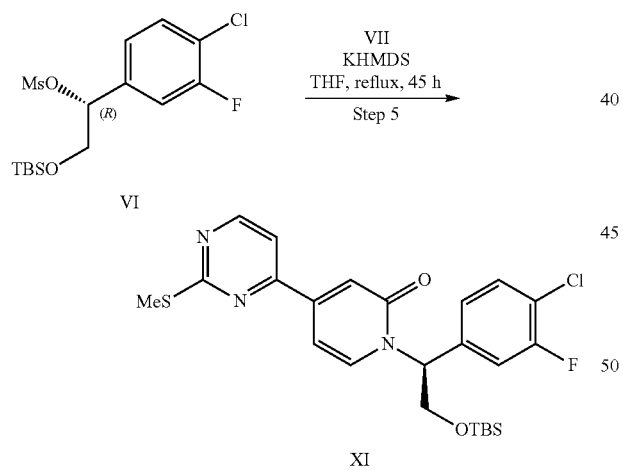

Procedure:
1. Add VII (1 eq.) and DGME (20V) into flask under N₂
2. Cool to 0° C.
3. Add KHMDS (1 M in THF, 1 eq.)
4. Add VI (1.2-1.5 eq.) in DGME solution
5. Stir at 0° C. for 5 min
6. Heat to reflux (jacket 120° C.) and stir for over 4 h
7. Cool down
8. Quench with water and extraction with MTBE
9. Wash with 20% NaCl
10. Dry over Na₂SO₄
11. Concentrate to dryness and use to next step directly Step 6:

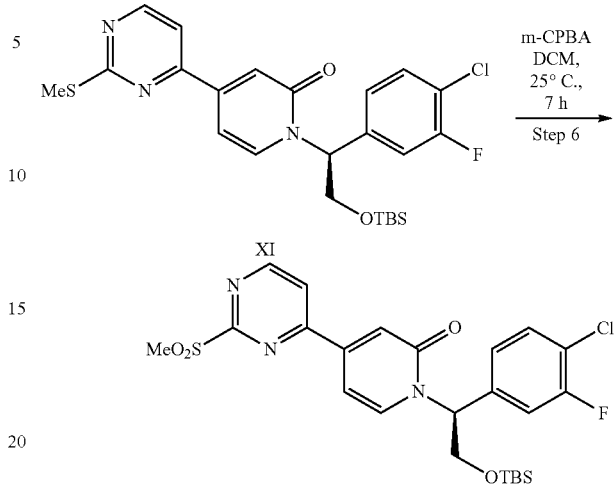

Procedure:
1. Charge XI (1 eq.), DCM (8V) into flask under N₂
2. Add mCPBA by portions
3. Stir at room temperature for 2 h
4. Add 7% NaHCO₃ aq. to wash
5. Quench with Na₂S₂O₄ aq.
6. Wash with 20% NaCl aq.
7. Dry over Na₂SO₄
8. Filter and concentrate to dryness
9. Slurry the result in MTBE (3V) to afford I Step 7:

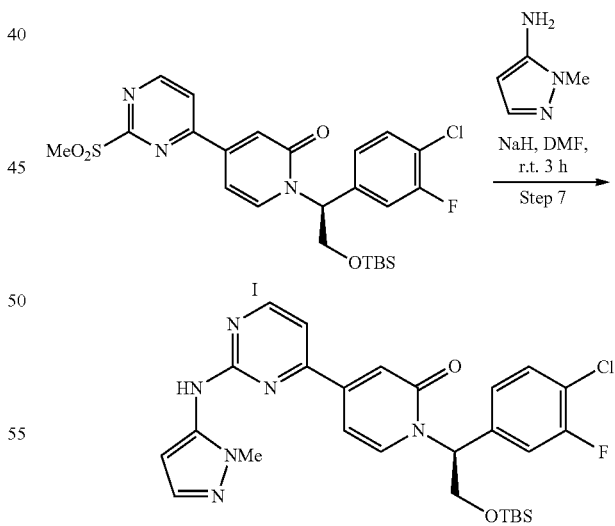

Procedure:
1. Add I (1 eq.), 1-methyl-1H-pyrazol-5-amine (4 eq.), Cs₂CO₃, DMF (4V) into a flask under N₂
2. Stir at room temperature for 3 h
3. Work-up to afford product.

Step 8:

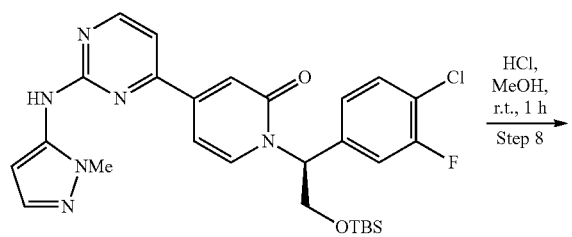

Procedure:
1. IX was dissolved in MeOH
2. HCl (1.25 M in MeOH) was charged at the ambient temperature.
3. After addition, the reaction was heated to 45° C. for 16 h.
4. The reaction was cooled to rt and quenched with aqueous NaHCO₃ and diluted with EtOAc
5. After the phase separation, the organic layer was washed with water. The organic layer was concentrated to afford the crude VIII Step 9:

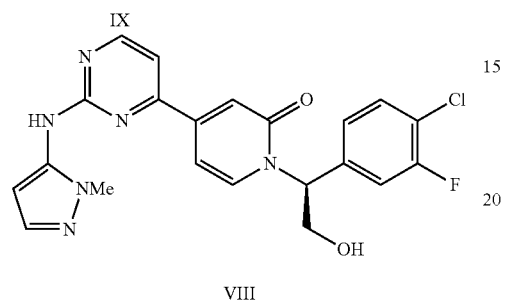

Procedure:
1. Charge compound 6-2, XIII, Pd-catalyst and sodium bicarbonate to a four-necked jacketed flask with paddle stirrer under N₂
2. Charge water and 1,4-dioxane (5.0V., KF<0.02%) to the flask
3. Stir the suspension at 85° C. for 16 hrs
4. Filter through the silica-gel (2.0 X) and diatomaceous earth (0.5 X)
5. Remove the 1,4-dioxane by distillation under a vacuum
6. Partition between water (2.0V) and EtOAc (5.0V)
7. Separate the organic phase and concentrate
8. Purify by re-crystallization from PE and EtOAc Step 10:

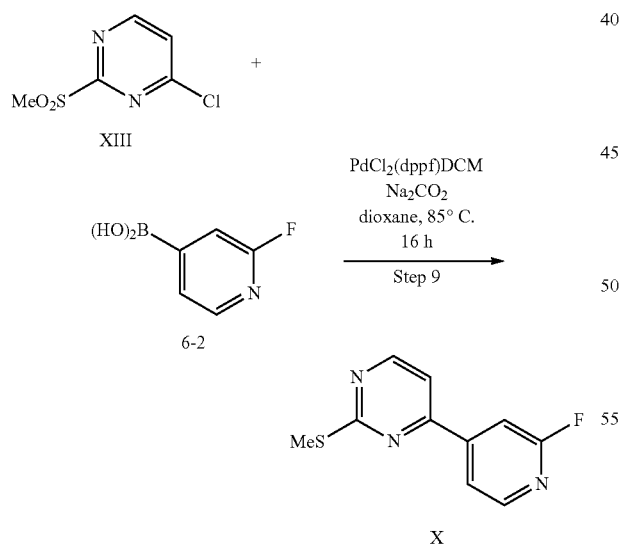

Procedure:
Add X into a flask
Add 2M HCl (10-15V)
Heat to 100° C. and stir for 3 h
Cool down
Neutralize pH to 7 to 8 with 30% NaOH aq.
Extract with THF
Wash with 20% NaCl aq.
Dry over Na₂SO₄
Filter and concentrate to dryness Synthesis of Crystalline (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one benzenesulfonate salt (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one (21.1 mg, 0.048 mmol) was dissolved in MEK (0.5 mL). Benzenesulfonic acid (Fluka, 98%, 7.8 mg, 0.049 mmol) was dissolved in MEK (0.5 mL) and the resulting solution added drop wise to the free base solution with stirring. Precipitation occurred and the precipitate slowly dissolved as more benzenesulfonic acid solution was added. A small amount of sticky solid remained on the bottom of the vial. The vial contents were sonicated for 10 minutes during which further precipitation occurred. The solid was isolated after centrifugation and vacuum dried at 40° C. using house vacuum.

Synthesis of (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one benzenesulfonate salt crystalline Form A (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one, benzenesulfonate salt (23.1 mg) was dissolved in hot isopropanol (5 mL) in a heating block set to 90° C. The heat was turned off on the heating block and the solution was allowed to cool to ambient and then placed in a freezer at about −20° C. The solid was collected while still cold and analyzed by XRPD to give (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one, benzenesulfonate salt Form A.

Synthesis of (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one, benzenesulfonate salt crystalline Form A Single Crystals Suitable for Single Crystal Structure Determination as Set Forth Below (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one, benzenesulfonate salt crystalline Form A: Crystals of suitable quality for structure determination were grown in methanol via stirring at approximately 50° C., isolating into Paratone-N oil after approximately 1 day and storing under ambient conditions.

Structural solution: A colorless plate of $C_{27}H_{23}ClFN_6O_5S$ [$C_{21}H_{18}ClFN_6O_2$, $C_6H_5O_3S$] having approximate dimensions of 0.16×0.16×0.06 mm, was mounted on a fiber in random orientation. Preliminary examination and data collection were performed with Cu Kα radiation ($\lambda$=1.54178 Å) on a Rigaku Rapid II diffractometer equipped with confocal optics. Refinements were performed using SHELX2013 [Sheldrick, G. M. *Acta Cryst.*, 2008, A64, 112].

Cell constants and an orientation matrix for data collection were obtained from least-squares refinement using the setting angles of 24479 reflections in the range 3°<θ<63°. The refined mosaicity from DENZO/SCALEPACK was 0.59°, indicating moderate crystal quality [Otwinowski, Z.; Minor, W. *Methods Enzymol.* 1997, 276, 307]. The space group was determined by the program XPREP [Bruker, XPREP in SHELXTL v. 6.12., Bruker AXS Inc., Madison, Wis., USA, 2002]. There were no systematic absences, and the space group was determined to be P1 (no. 1).

The data were collected to a maximum 2θ value of 126.9°, at a temperature of 293±1 K.

Frames were integrated with HKL3000 [Flack, H. D.; Bernardinelli, G., *Acta Cryst.* 1999, A55, 908]. A total of 24479 reflections were collected, of which 6536 were unique. Lorentz and polarization corrections were applied to the data. The linear absorption coefficient is 2.450 mm$^{-1}$ for Cu Kα radiation. An empirical absorption correction using SCALEPACK [Otwinowski, Z.; Minor, W. *Methods Enzymol.* 1997, 276, 307] was applied. Transmission coefficients ranged from 0.564 to 0.863. A secondary extinction correction was applied [Glusker, Jenny Pickworth; Trueblood, Kenneth N. *Crystal Structure Analysis: A Primer*, 2$^{nd}$ ed.; Oxford University press: New York, 1985; p.87]. The final coefficient, refined in least-squares, was 0.00170 (in absolute units). Intensities of equivalent reflections were averaged. The agreement factor for the averaging was 9.8% based on intensity.

The structure was solved by direct methods using SHELXT [Burla, M. C., Caliandro, R., Camalli, M., Carrozzini, B., Cascarano, G. L., De Caro, L., Giacovazzo, C., Polidori, G., and Spagna, R., *J. Appl. Cryst.* 2005, 38, 381]. The remaining atoms were located in succeeding difference Fourier syntheses. They hydrogen atoms residing on nitrogen atoms were refined independently. All other hydrogen atoms were included in the refinement but restrained to ride on the atom to which they are bonded. The structure was refined in full-matrix least-squares by minimizing the function:

$$\Sigma w(|F_o|^2 - |F_c|^2)^2$$

The weight w is defined as $1/[\sigma^2(F_o^2)+(0.2000P)^2+(0.000P)]$, where $P=(F_o^2+2F_c^2)/3$.

Scattering factors were taken from the "International Tables for Crystallography" [International Tables for Crystallography, Vol. C, Kluwer Academic Publishers: Dordrecht, The Netherlands, 1992, Tables 4.2.6.8 and 6.1.1.4]. Of the 6536 reflections used in the refinements, only the reflections with $F_o^2>2\sigma(F_o^2)$ were used in calculating the fit residual, R. A total of 5796 reflections were used in the calculation. The final cycle of refinement included 771 variable parameters and converged (largest parameter shift was <0.01 times its estimated standard deviation) with unweighted and weighted agreement factors of:

$$R=\Sigma|F_o-F_c|/\Sigma F_o=0.096$$

$$R_w=\sqrt{(\Sigma w(F_o^2-F_c^2)^2/\Sigma w(F_o^2)^2)}=0.283$$

The standard deviation of an observation of unit weight (goodness of fit) was 1.385. The highest peak in the final difference Fourier had a height of 0.85 e/Å$^3$. This is rather high and indicative of the poor quality of the structure refinement. The minimum negative peak had a height of −0.28 e/Å$^3$. The Flack factor for the determination of the absolute structure [Flack, H. D. *Acta Cryst.* 1983, A39, 876] refined to −0.01(4).

One of the hydroxyl groups of one of the molecules in the asymmetric unit was refined using disorder. This leads to the splitting of the O22 and H22 atoms into the O22A, H22A and O22B, H22B pairs of atomic coordinates.

Figure 3:
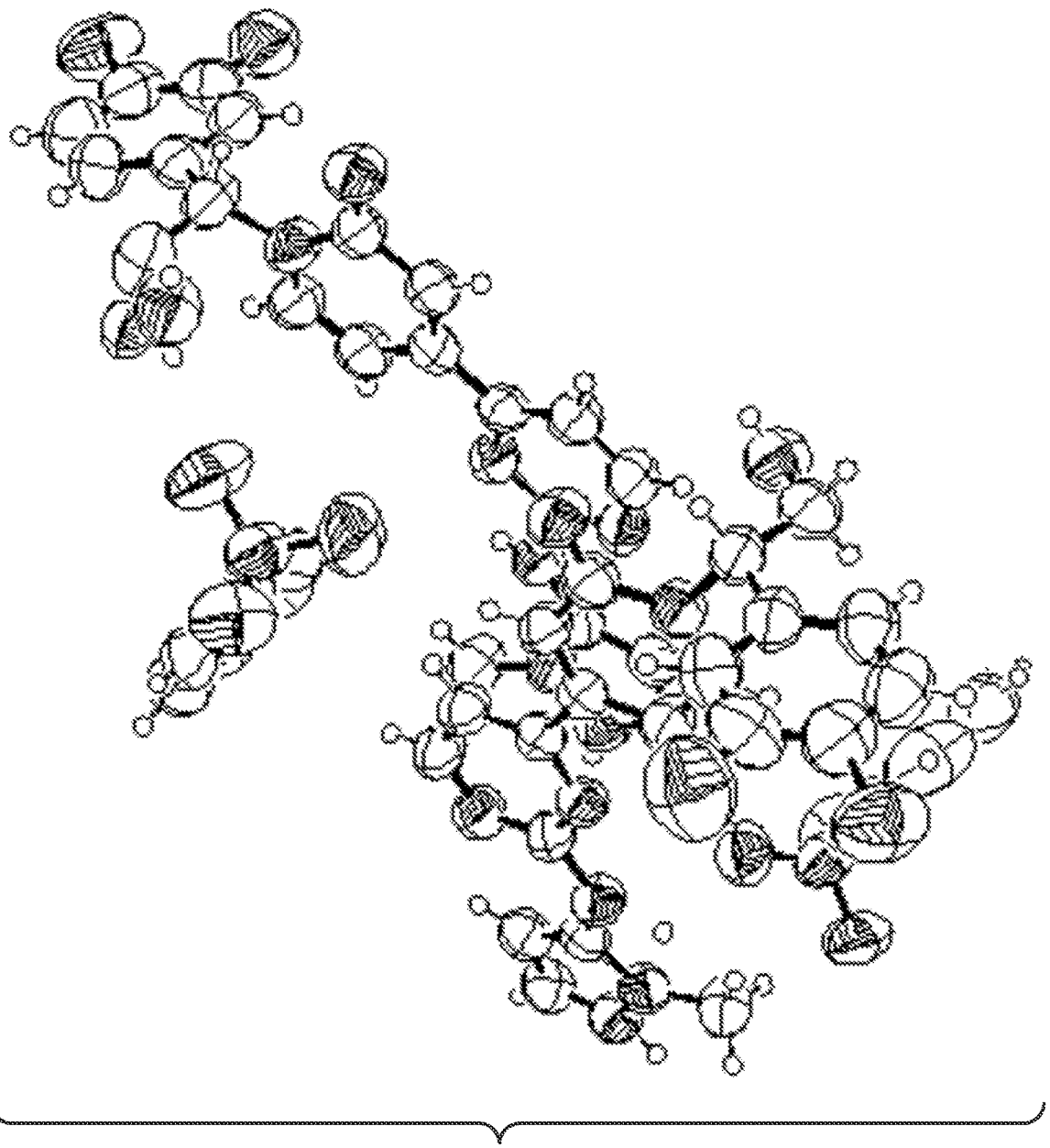
FIG. 3 shows the single crystal structure analysis of VIII crystalline besylate form A.

A representation of a single molecule of (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one, benzenesulfonate salt crystalline Form A, determined from the single crystal analysis, is shown in FIG. 3. Disorder in the hydroxymethyl group can be observed in the upper right of FIG. 3.

Single Crystal Data and Data Collection Parameters for VIIIb

| Formula | $C_{27}H_{24}ClFN_6O_5S$ |
| --- | --- |
| formula weight | 598.04 |
| space group | P1 (No. 1) |
| a, Å | 7.7973(9) |
| b, Å | 12.2869(13) |
| c, Å | 14.7832(14) |
| α, deg | 103.489(7) |
| β, deg | 91.519(8) |
| γ, deg | 97.231(10) |
| V, Å$^3$ | 1364.0(2) |
| Z' | 2 |
| temperature, K. | 293 |

-continued

| | |
|---|---|
| mosaicity, deg | 0.59 |
| Rint | 0.098 |
| R(Fo) | 0.096 |
| Rw(Fo2) | 0.283 |
| goodness of fit | 1.385 |
| absolute structure determination | Flack parameter (−0.01(4)) Hooft parameter (−0.045(17)) |

(S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one, benzenesulfonate salt crystallizes in chiral triclinic space group P-1 with two symmetrically independent cation anion pairs. Although the geometrical parameters indicate that all of the intermolecular interactions can be treated as relatively strong, both cations are highly disordered. Two conformations of the chlorofluorophenyl groups were found with an occupancy ratio of about 60:40. In addition, the hydroxymethyl group was also disordered with an occupancy ratio of about 50:50. The absolute stereochemistry is assigned the S-configuration.

Synthesis of amorphous (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one benzenesulfonate salt (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one benzenesulfonate salt (39.6 mg) in tert-butanol (about 20 mL) was heated to 60° C. in a heating block. The tert-butanol has been melted at about 30° C. prior to addition to the besylate salt. Water (200 µ) was added and heated until a clear solution resulted. The solutions were cooled and filtered through a 0.2 µm filter and placed in a lyophillizer. This compound was lyophilized using a SP Scientific VirTis AdVantage 2.0 Benchtop Freeze Dryer. A 70-hour recipe was used to remove solvent from the compound.

The initial freezing of the compound was done under a vacuum at −70° C. for 1.5 hours at 500 mTorr pressure. This ensures that the entire solution is completely frozen before primary drying is started. Primary drying is done to remove the bulk solvent via sublimation. From −70° C., the temperature is raised to −35° C. and the pressure is lowered to 100 mTorr for 1 hour. After drying at −35° C. for 1 hour, the temperature is raised to 5° C. and dried for an additional 28 hours at the same pressure. Primary drying ends with the last step at 15° C. which is held for 16 hours. The lyophilization pressure is lowered to 50 mTorr and the temperature is raised to 35° C. for 16 hours. Secondary drying continues with the temperature lowering to 30° C. and pressure lowering to 10 mTorr for 6 hours. The final step of the lyophilization cycle has the temperature lowered to 25° C. and the pressure raised back to 2500 mTorr for 1 hour.

Synthesis of (S)-1-(1-(4-chloro-3-fluorophenyl)-2-hydroxyethyl)-4-(2-((1-methyl-1H-pyrazol-5-ylamino)pyrimidin-4-yl)pyridin-2(1H)-one, 1,5-naphthalenedisulfonate: crystalline Form I (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one (21.8 mg, 0.0494 mmol) was dissolved in MEK (0.5 mL). 1,5-naphthalenedisulfonic acid tetrahydrate (25.1 mg, 0.0871 mmol) was dissolved in methanol (1.0 mL) and about 0.36 mL of the solution was added drop wise to the free base solution with stirring. Precipitation occurred. The suspension was allowed to slowly evaporate until only a trace of solvent remained. The solid was vacuum dried at 40° C. using house vacuum.

Synthesis of (S)-1-(1-(4-chloro-3-fluorophenyl)-2-hydroxyethyl)-4-(2-((1-methyl-1H-pyrazol-5-ylamino)pyrimidin-4-yl)pyridin-2(1H)-one, 1,5-naphthalenedisulfonate: crystalline Form II (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one (103.3 mg, 0.234 mmol) was dissolved in MEK (2.5 mL). 1,5-naphthalenedisulfonic acid tetrahydrate (110.4 mg, 0.383 mmol) was dissolved in methanol (2.0 mL) and about 0.77 mL of the solution was added drop wise to the free base solution with stirring. Precipitation occurred including one big chunk. The chunk was broken up with a spatula followed by addition of methanol (0.77 mL). The suspension was allowed to stir for 3 day. The solid was isolated by filtration and dried at 60° C. using house vacuum to give 57 mg of a yellow solid.

Synthesis of (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one, tosylate IPA solvate and (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one, tosylate Form A (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one (105.1 mg, 0.239 mmol) was mostly dissolved in isopropanol (1 mL) using sonication. p-Toluenesulfonic acid monohydrate (97.5% pure, 52.9 mg, 0.271 mmol) was dissolved in isopropanol (1 mL). The toluenesulfonic acid solution was added drop wise to the free base solution with stirring to give a yellow solid. Additional isopropanol was added (1 mL). The solid was isolated by filtration and the reactor and solids were rinsed with 1 mL isopropanol. The solid was analyzed by XRPD in a holder open to the atmosphere while still wet with solids to give a disordered (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one, tosylate IPA solvate. TG analysis was conducted on the XRPD sample.

The remaining solid was dried at 60° C. under a vacuum for 4 days to give (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one, tosylate crystalline Form A.

Synthesis of (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one tosylate, amorphous form (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one (104.3 mg, 0.237 mmol) was dissolved in diethyl ether (60 mL). p-Toluenesulfonic acid monohydrate (52.0 mg, 0.273 mmol) was dissolved in diethyl ether (5 mL). The toluenesulfonic acid solution was added drop wise to the free base solution with stirring and the suspension stirred overnight. The ether was decanted and the solid allowed to air dry to get 103 mg of a yellow solid.

Synthesis of (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one tosylate, amorphous form and Form B Mixture (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one tosylate, amorphous form, (10.8 mg) was placed into a vial with a stir bar. Methyl ethyl ketone (MEK, 0.3 mL) was added and the slurry stirred for 4 days. Solvent was evaporated under a vacuum at 60° C. to give a yellow solid.

Powder X-ray diffraction patterns of samples were obtained using the Rigaku MiniFlexII powder X-ray diffractometer using reflection geometry. The copper radiation source was operated at the voltage of 30 kV and the current 15 mA. Each sample was placed in the cavity of an aluminum sample holder fitted with a zero background quartz insert and flattened with a glass slide to present a good surface texture and inserted into the sample holder. All samples were measured in the 2θ angle range between 2° and 40° with a scan rate of 2°/min and a step size of 0.02°.

A TA Instruments differential scanning calorimeter (Model Q100 or Model Q2000) with a mechanical cooler and a standard cell (configured the same as the sample pan) was used to measure the thermal properties of the powder samples. Each sample was loaded into a closed aluminium pan with a non-crimped lid containing zero to one pin hole and placed into the differential scanning calorimtery (DSC) cell. The cell has a nitrogen purge flowing at approximately 50 cm³/min. The cell and sample were equilibrated at 20° C. The cell was then heated to 209° C. or 250-350° C. at 10.00° C./min while monitoring the heat flow difference between the empty reference pan and the sample pan.

Modulated DSC was used to analyze (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one amorphous free base. A TA Instruments differential scanning calorimeter (Model Q2000) with a mechanical cooler and a standard cell (configured the same as the sample pan) was used to measure the thermal properties of the powder samples. Each sample was loaded into a closed aluminium pan with a non-crimped lid containing zero to one pin hole and placed into the differential scanning calorimtery (DSC) cell. The cell has a nitrogen purge flowing at approximately 50 cm³/min. The cell and sample were equilibrated at 25° C., the temperature was modulated at ±1° C. every 60 seconds, and held isothermally for 5 minutes. Data storage was turned on and the sample ramped at 3° C. to 100° C. The sample was then ramped to 25° C. at 3° C./minute. The sample was then heated at 3° C./minute to 200° C. The reversing signal is shown.

Automated vapor sorption data were collected on a TA Instruments Q5000SA vapor sorption analyzer. NaCl and PVP were used as calibration standards. Samples were not dried prior to analysis. Adsorption and desorption data were collected at 25° C. over a range from 5 to 95% RH at 10% RH increments under a nitrogen purge. Samples were held at the corresponding RH for 1 hour prior to moving to the next RH range. Data were not corrected for the initial moisture content of the samples.

Figure 4:
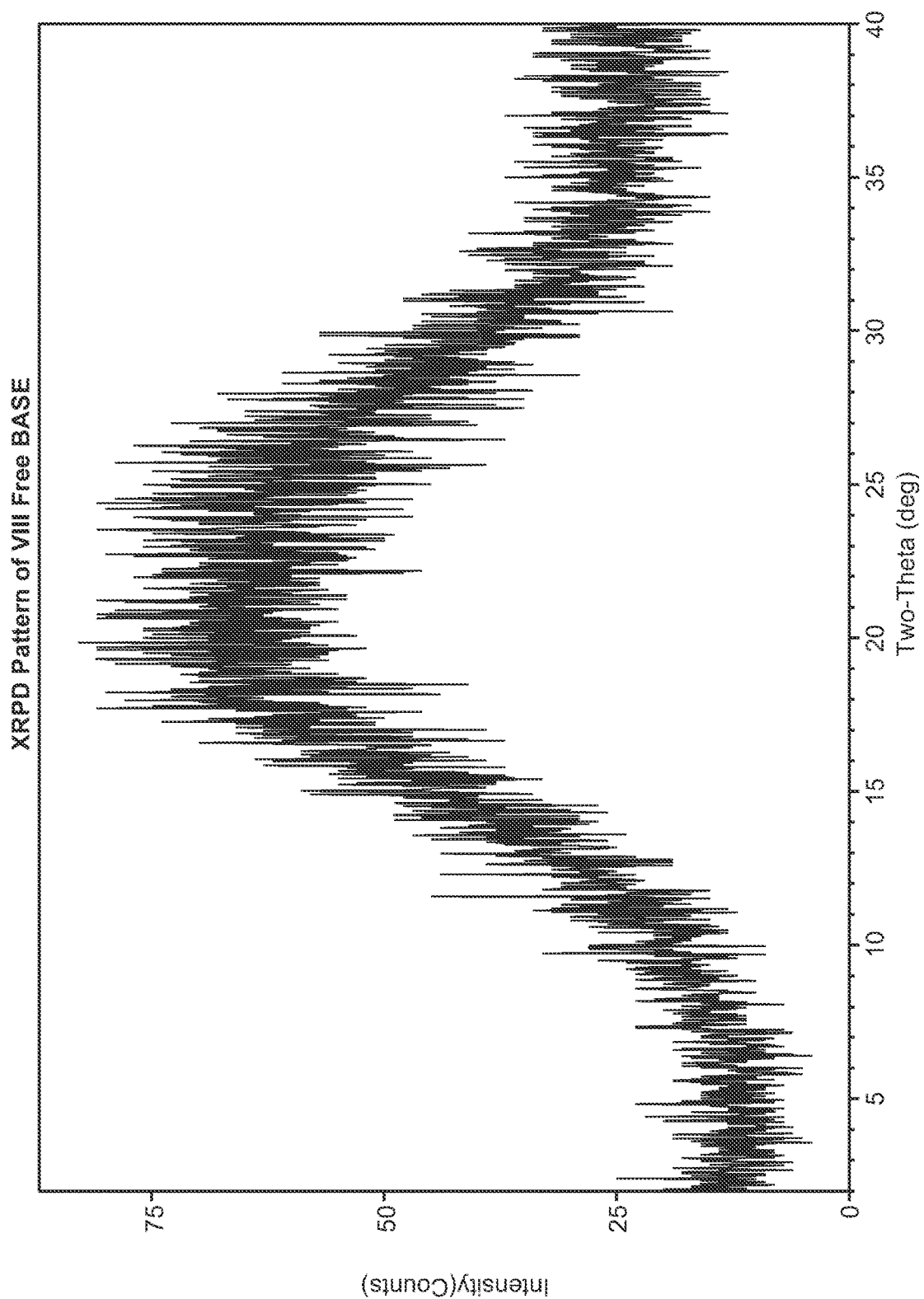
FIG. 4 shows the XRPD pattern of VIII free base.
Figure 5:
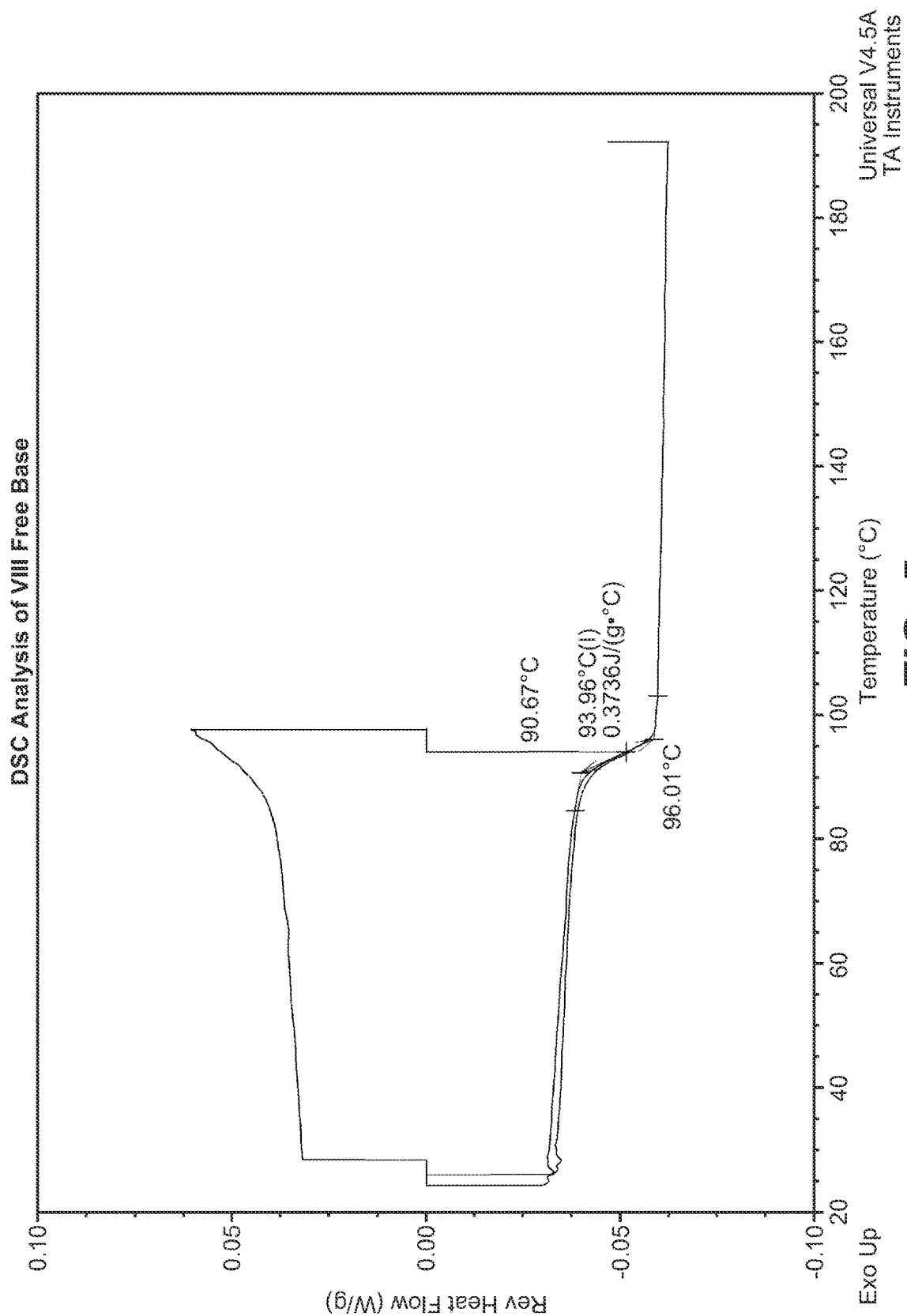
FIG. 5 shows the DSC analysis of VIII free base.
Figure 6:
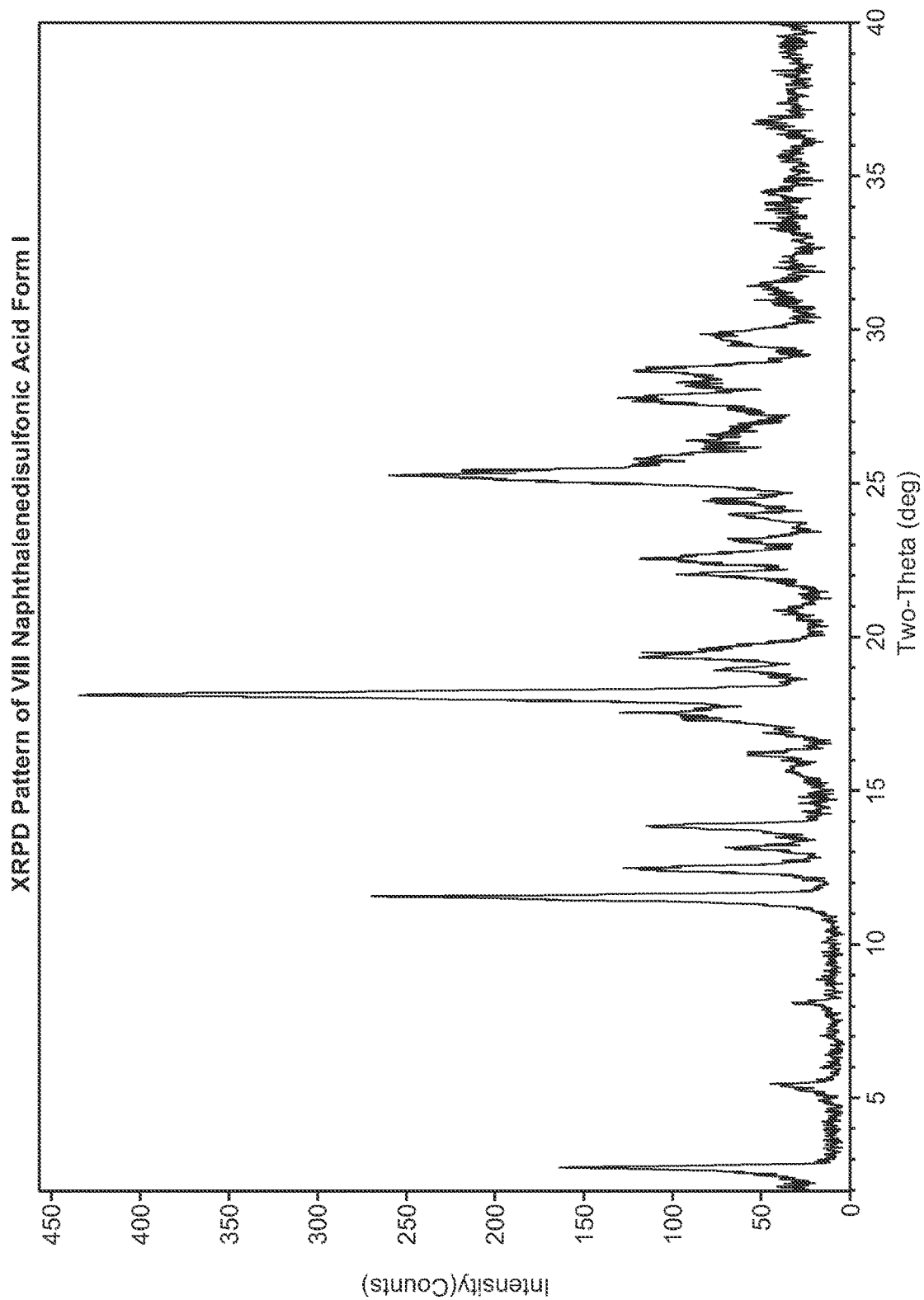
FIG. 6 shows the XRPD pattern of VIII naphthalenedisulfonic acid form I.
Figure 7:
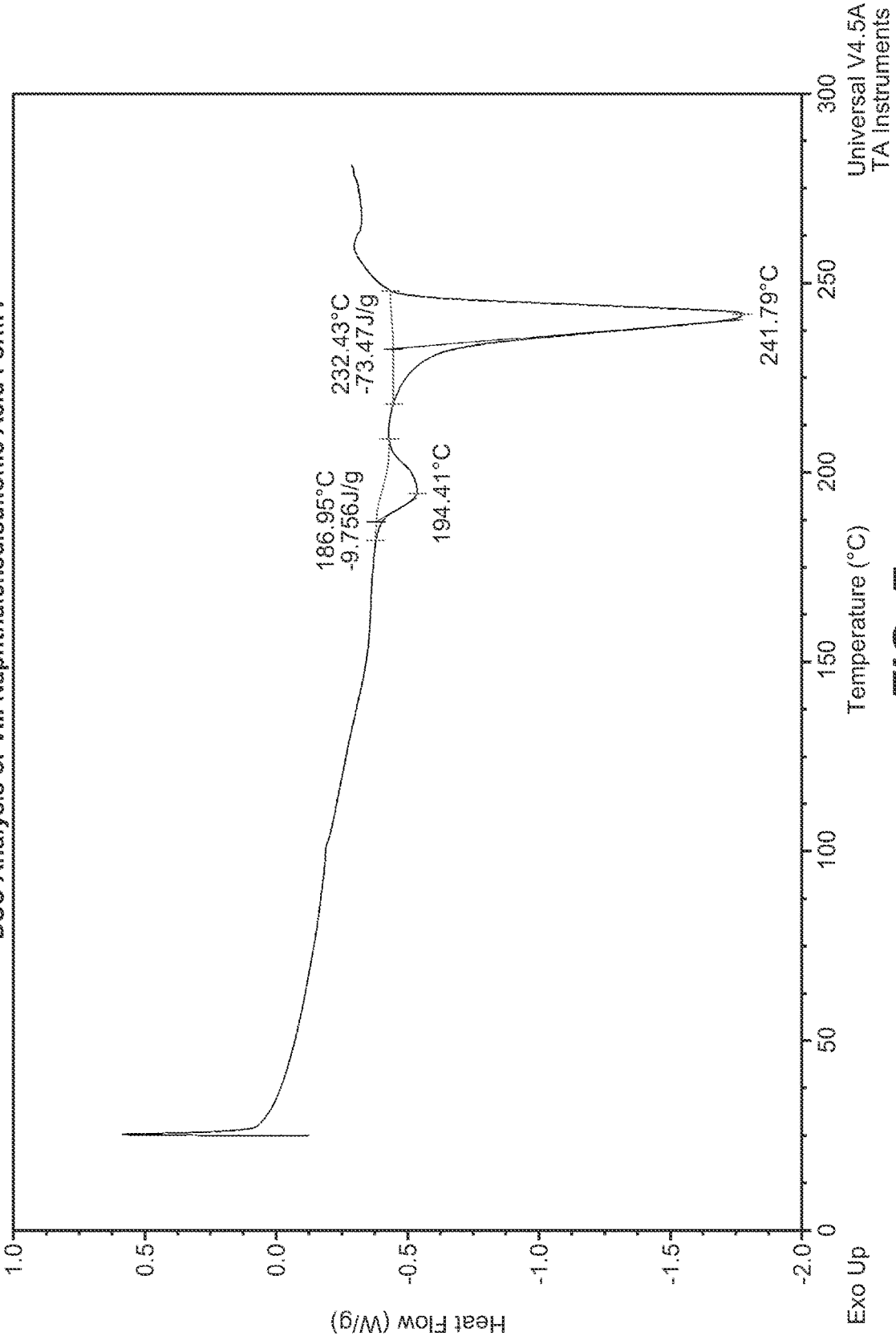
FIG. 7 shows the DSC analysis of VIII naphthalenedisulfonic acid form I.
Figure 8:
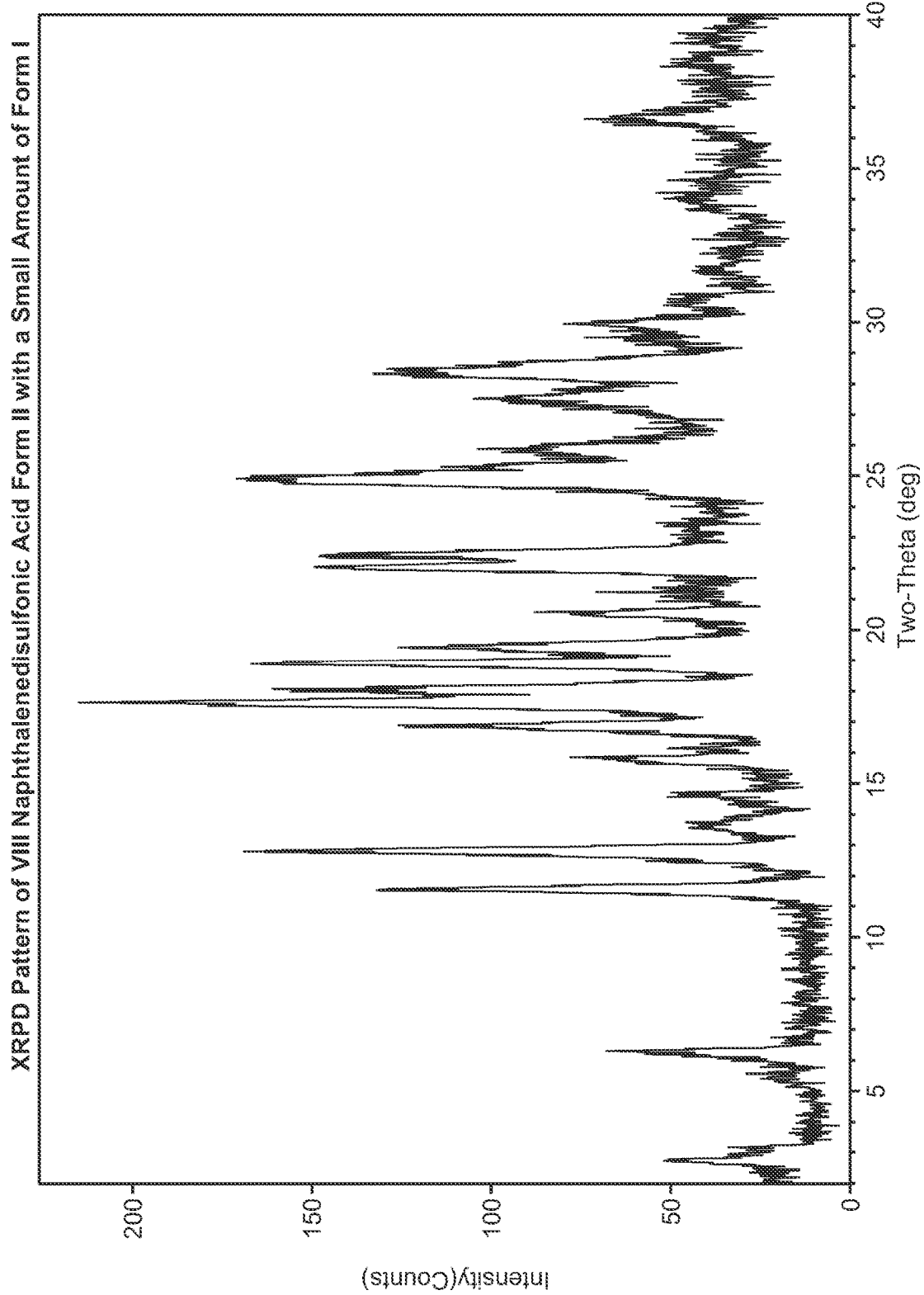
FIG. 8 shows the XRPD pattern of VIII naphthalenedisulfonic acid form II with a small amount of form I.
Figure 9:
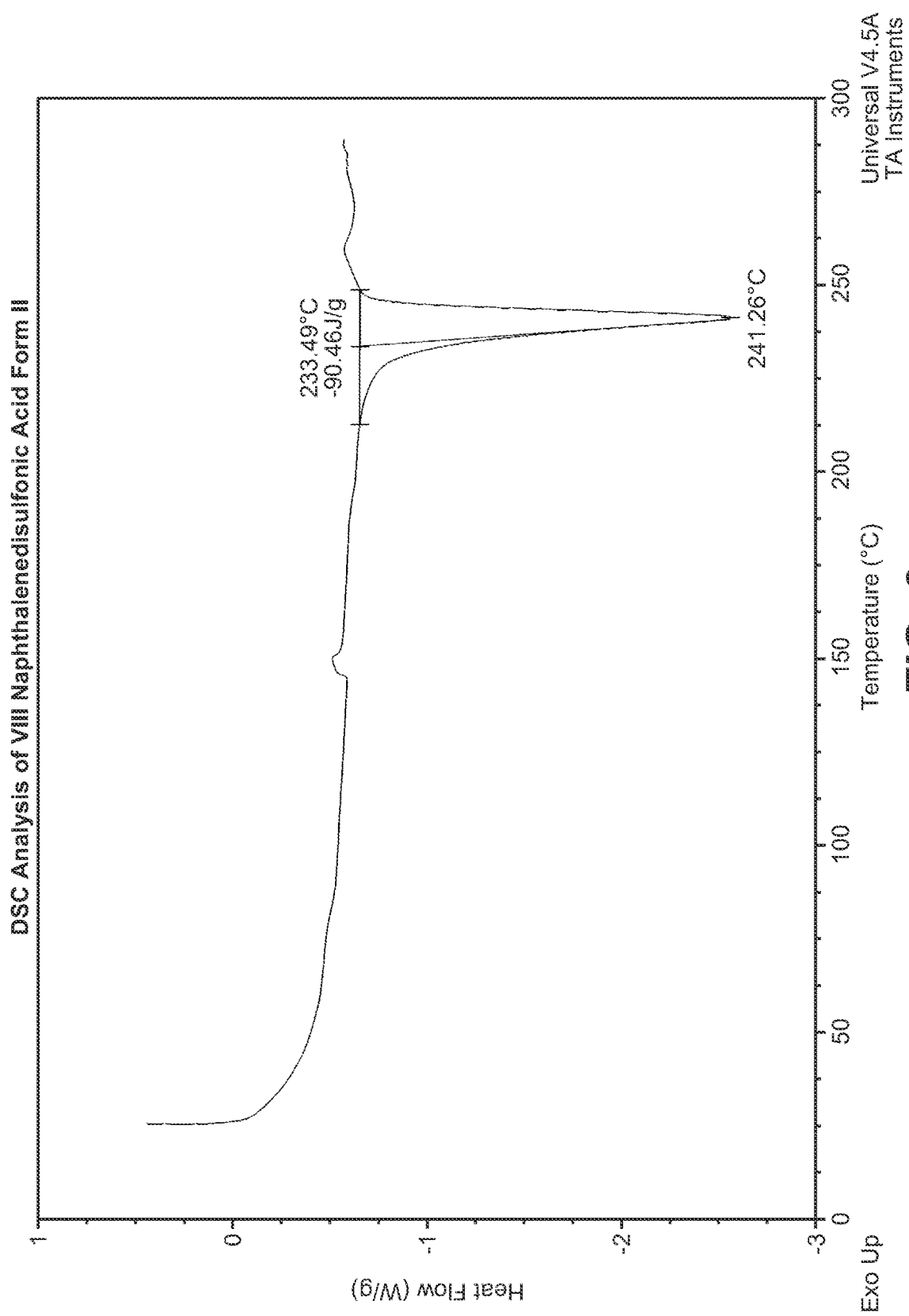
FIG. 9 shows the DSC analysis of VIII naphthalenedisulfonic acid form II.
Figure 10:
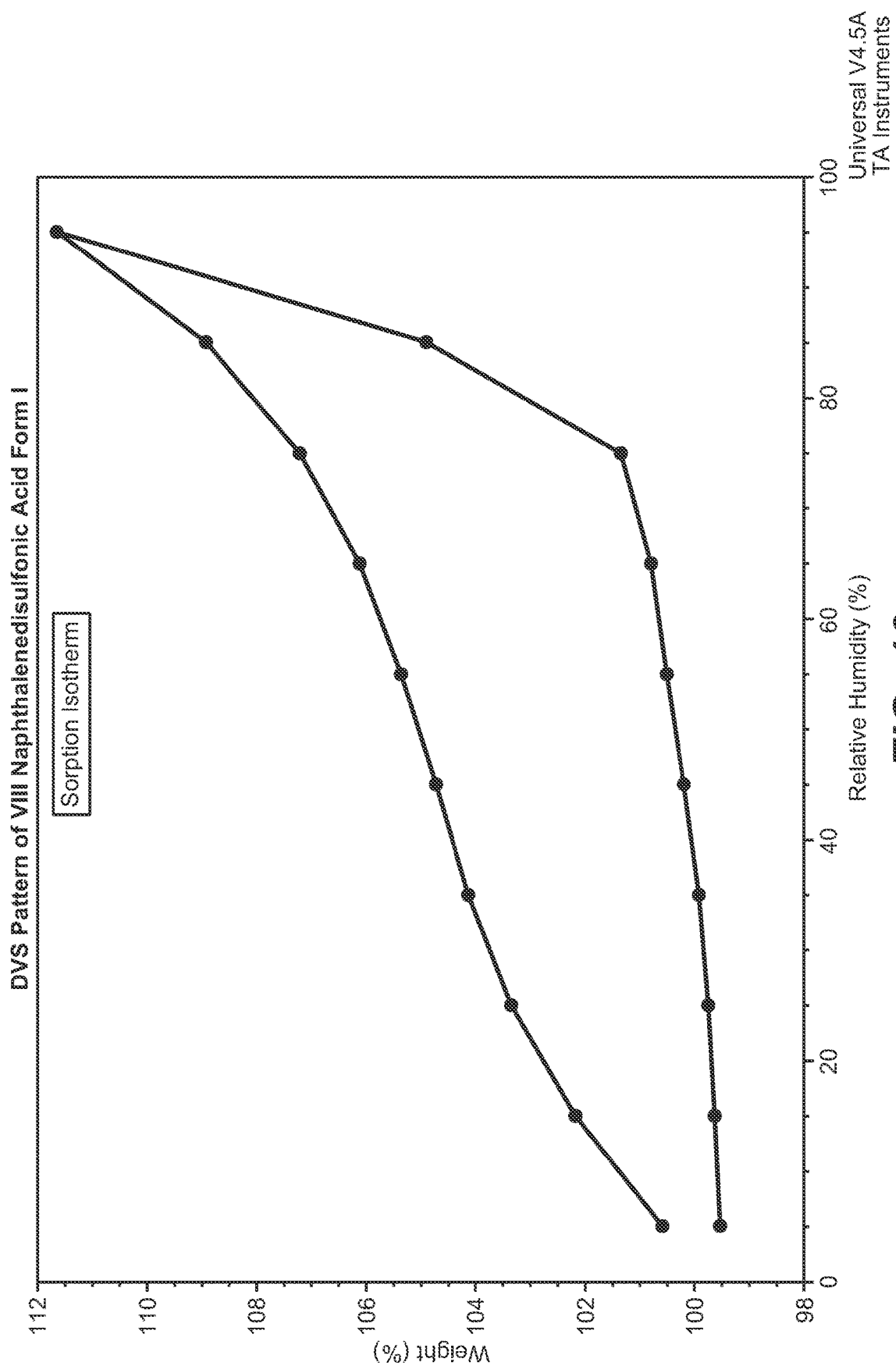
FIG. 10 shows the DVS pattern of VIII naphthalenedisulfonic acid form I.
Figure 11:
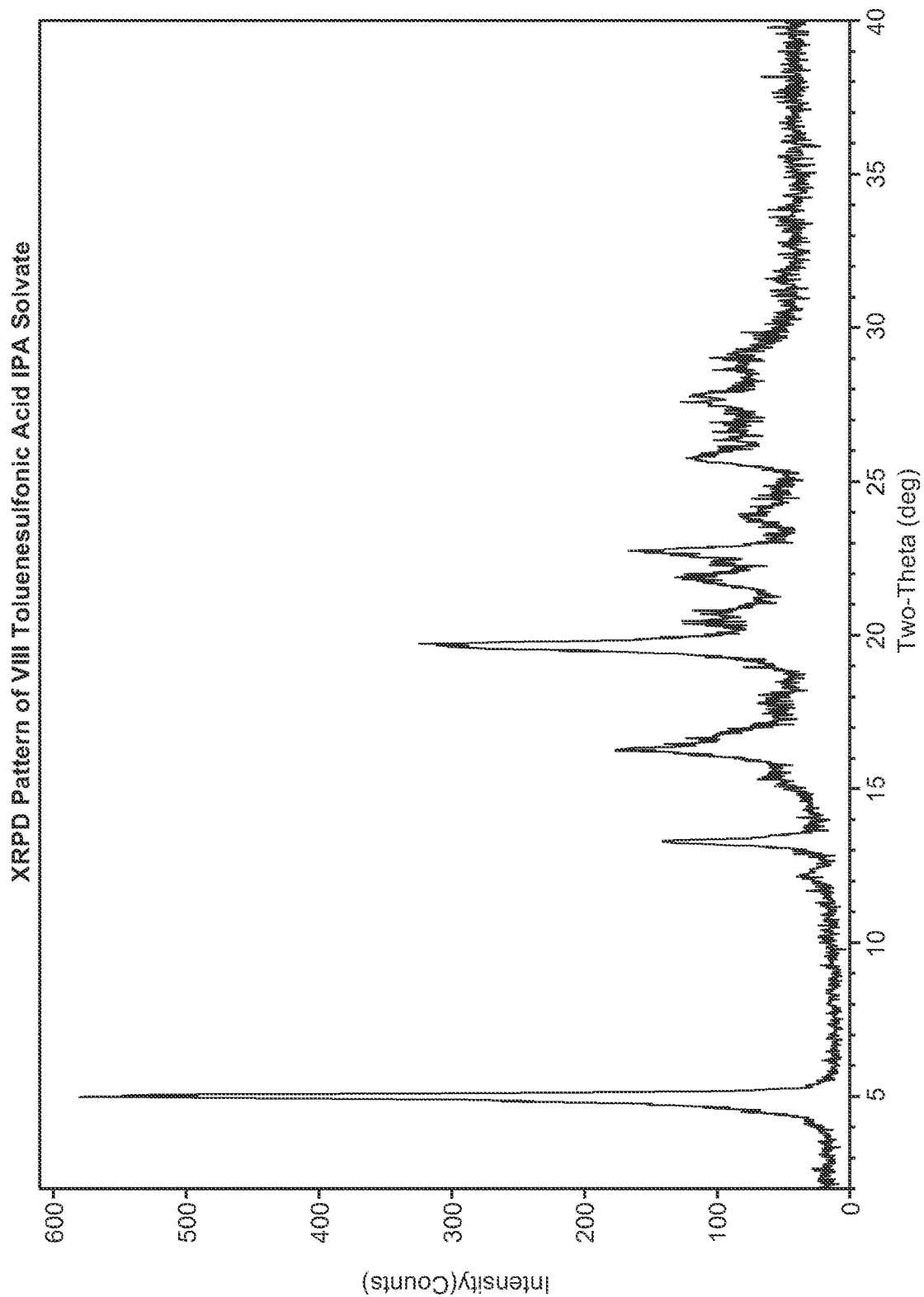
FIG. 11 shows the XRPD pattern of VIII toluenesulfonic acid IPA solvate.
Figure 12:
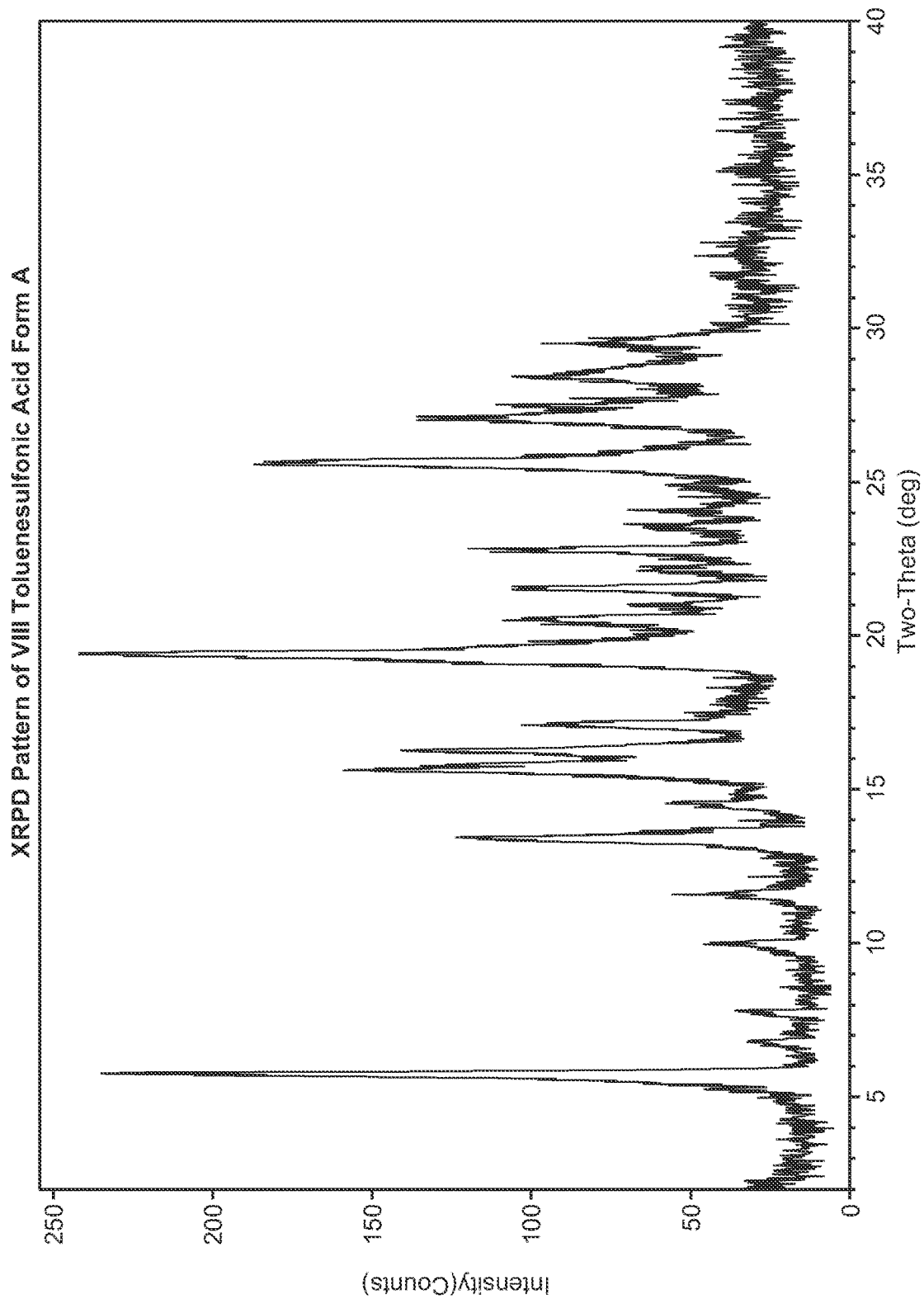
FIG. 12 shows the XRPD pattern of VIII toluenesulfonic acid form A.
Figure 13:
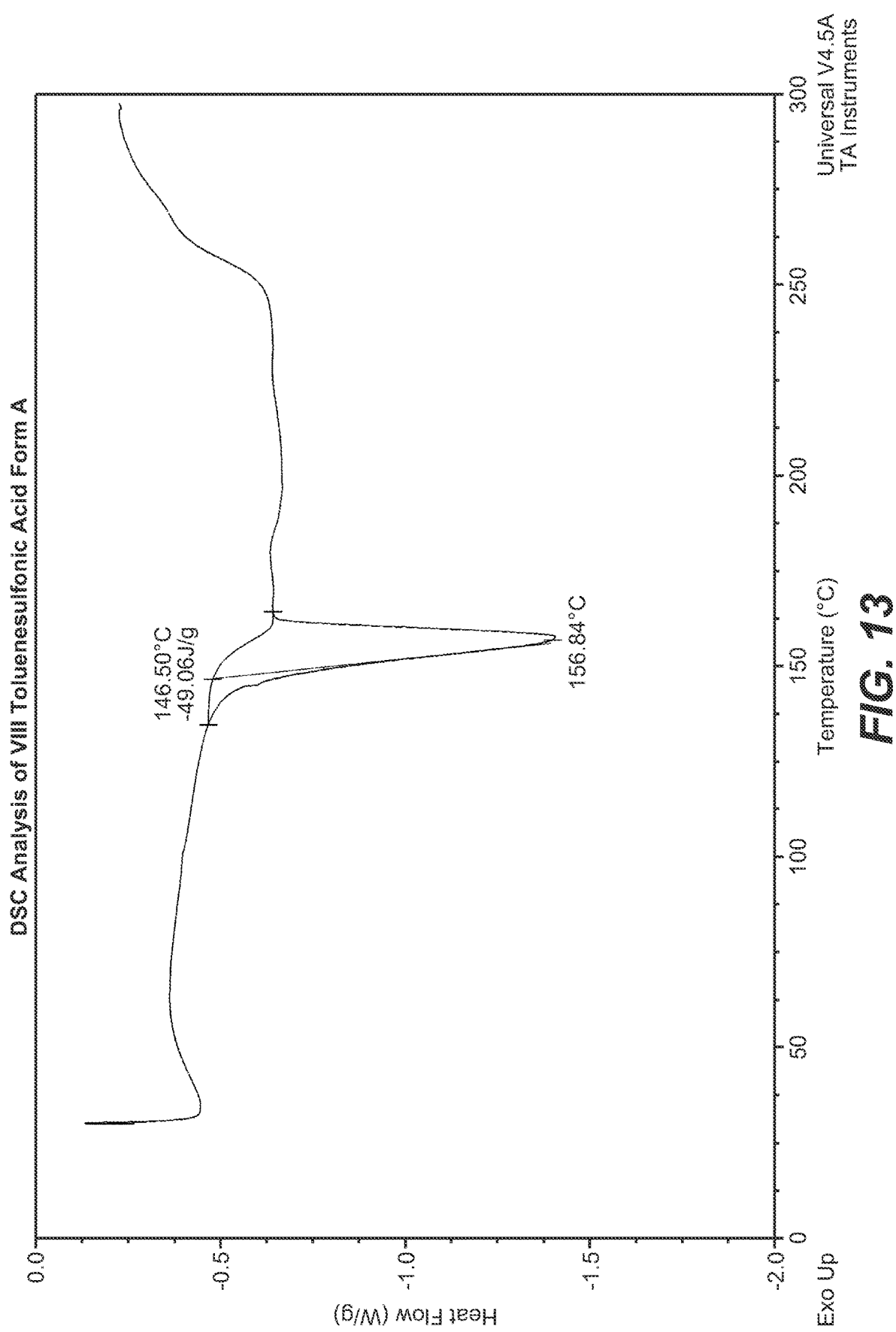
FIG. 13 shows the DSC analysis of VIII toluenesulfonic acid form A.
Figure 14:
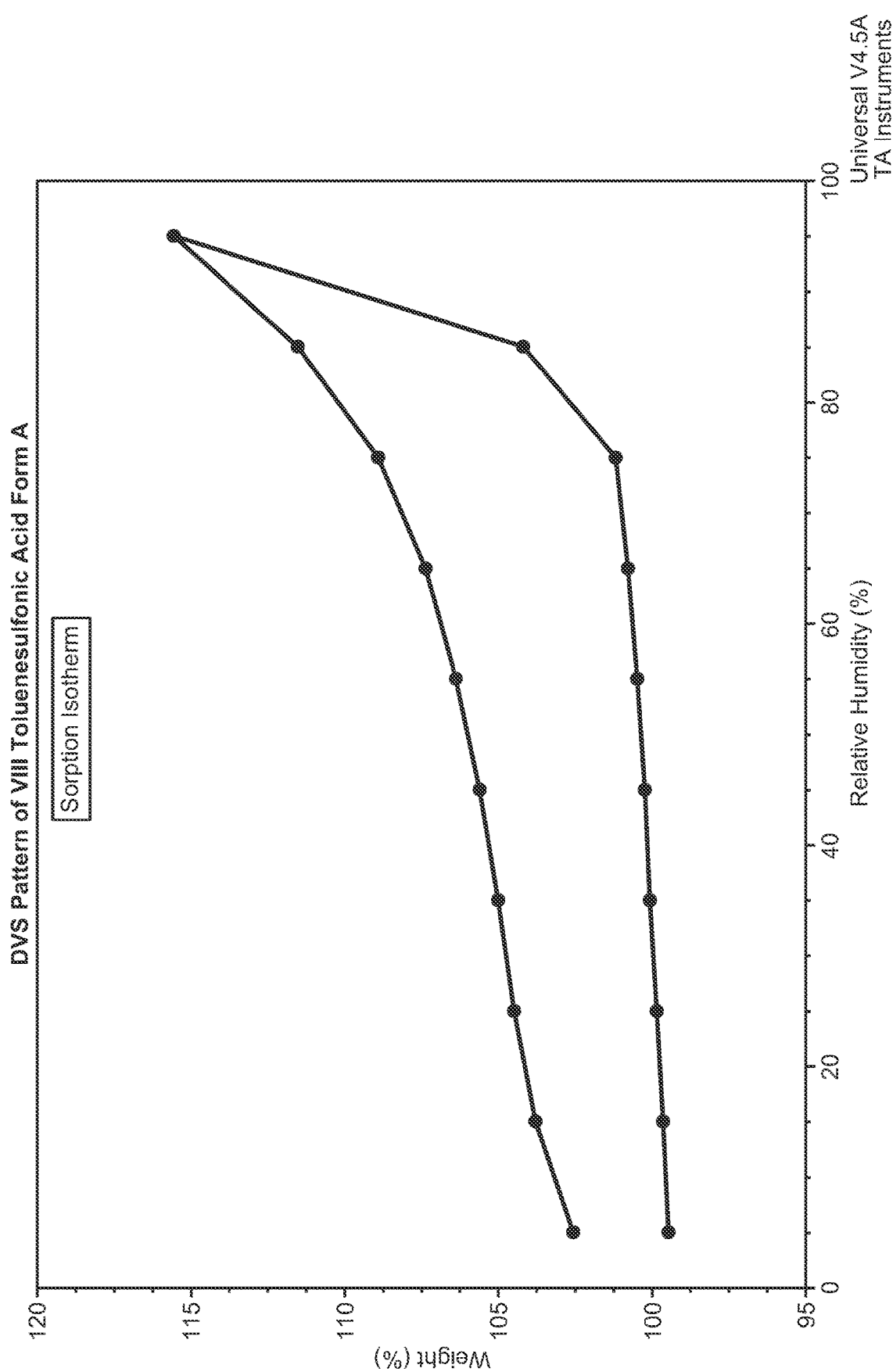
FIG. 14 shows the DVS pattern of VIII toluenesulfonic acid form A.
Figure 15:
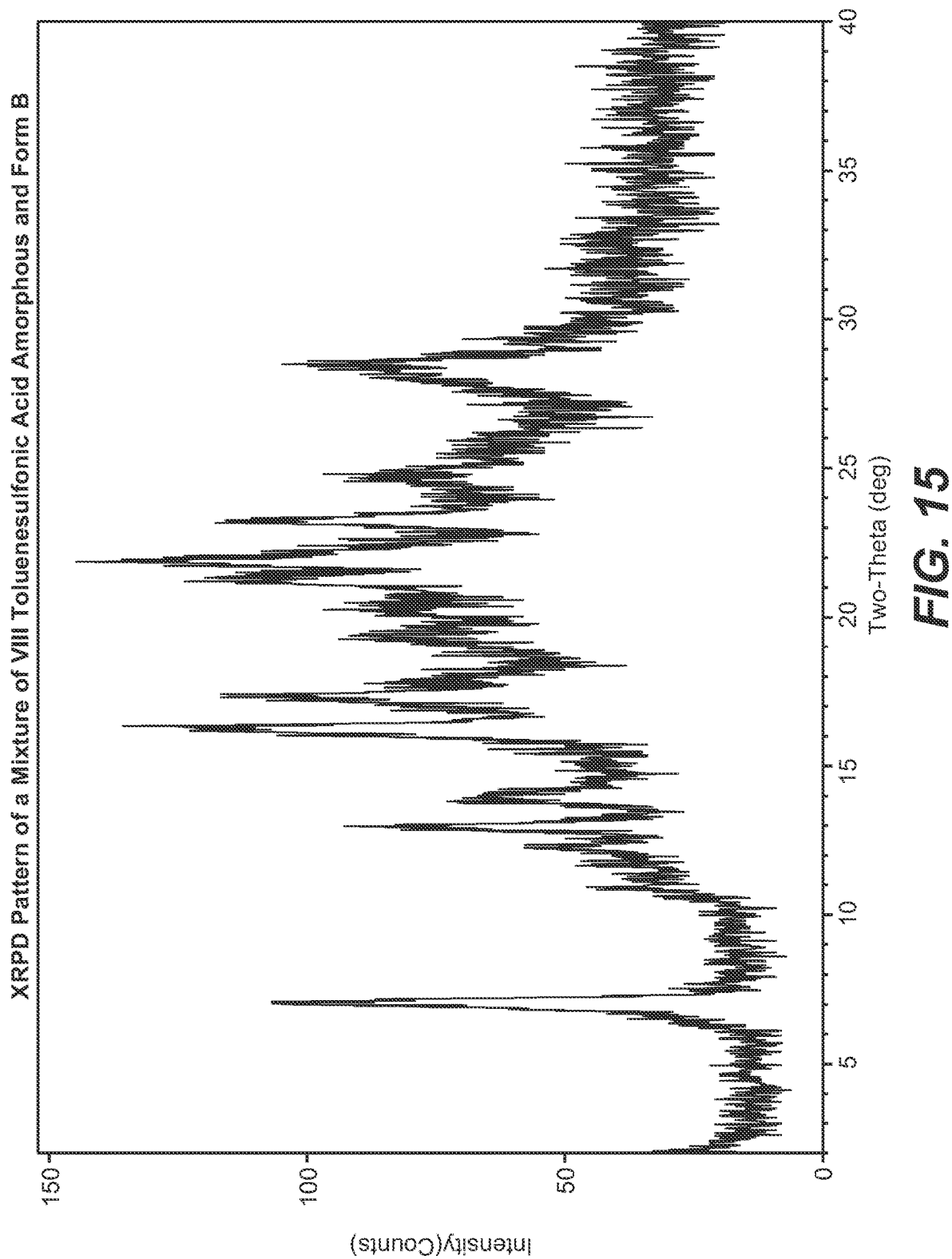
FIG. 15 shows the XRPD pattern of a mixture of VIII toluenesulfonic acid amorphous and form B.
Figure 16:
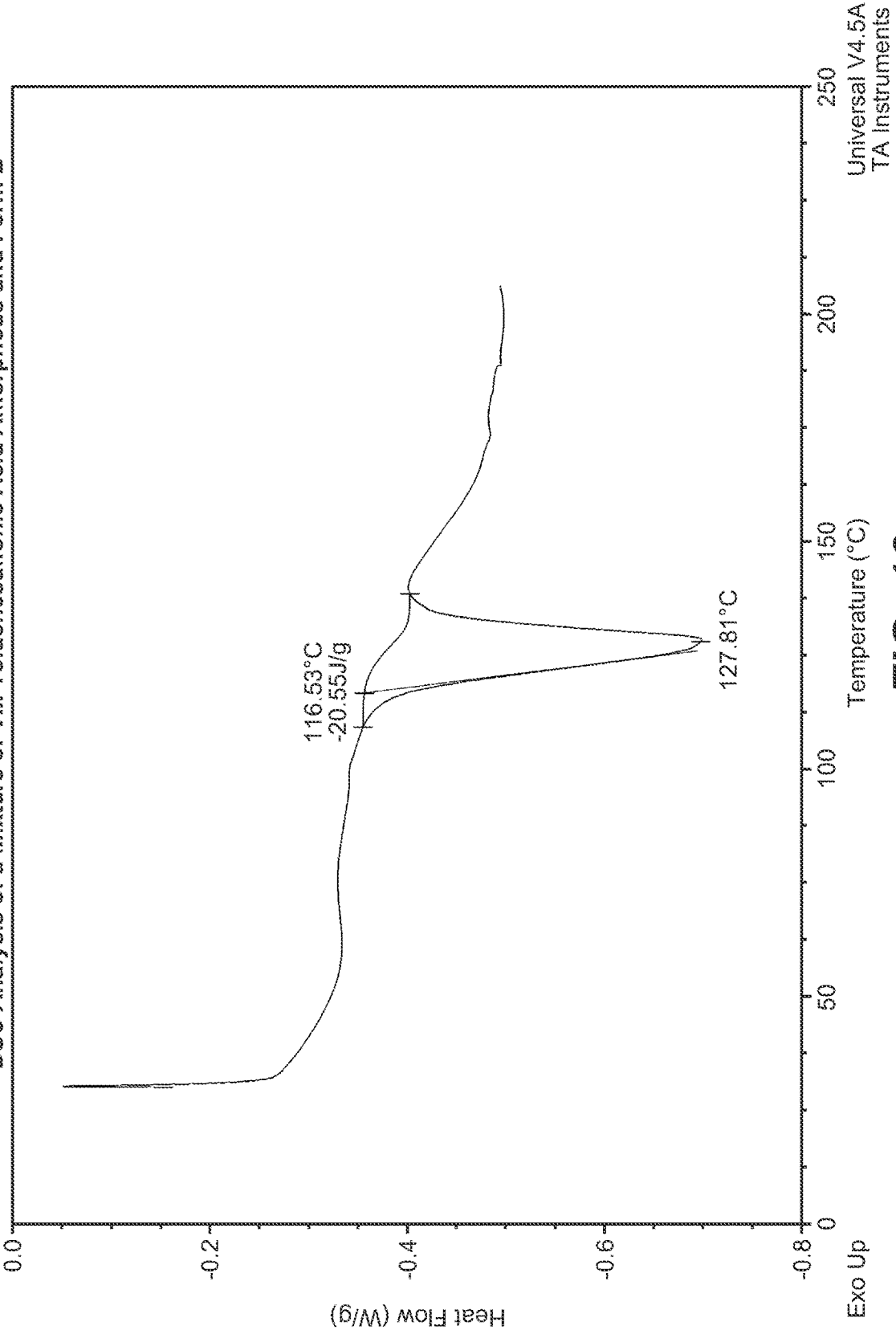
FIG. 16 shows the DSC analysis of a mixture of VIII toluenesulfonic acid amorphous and form B.
Figure 17:
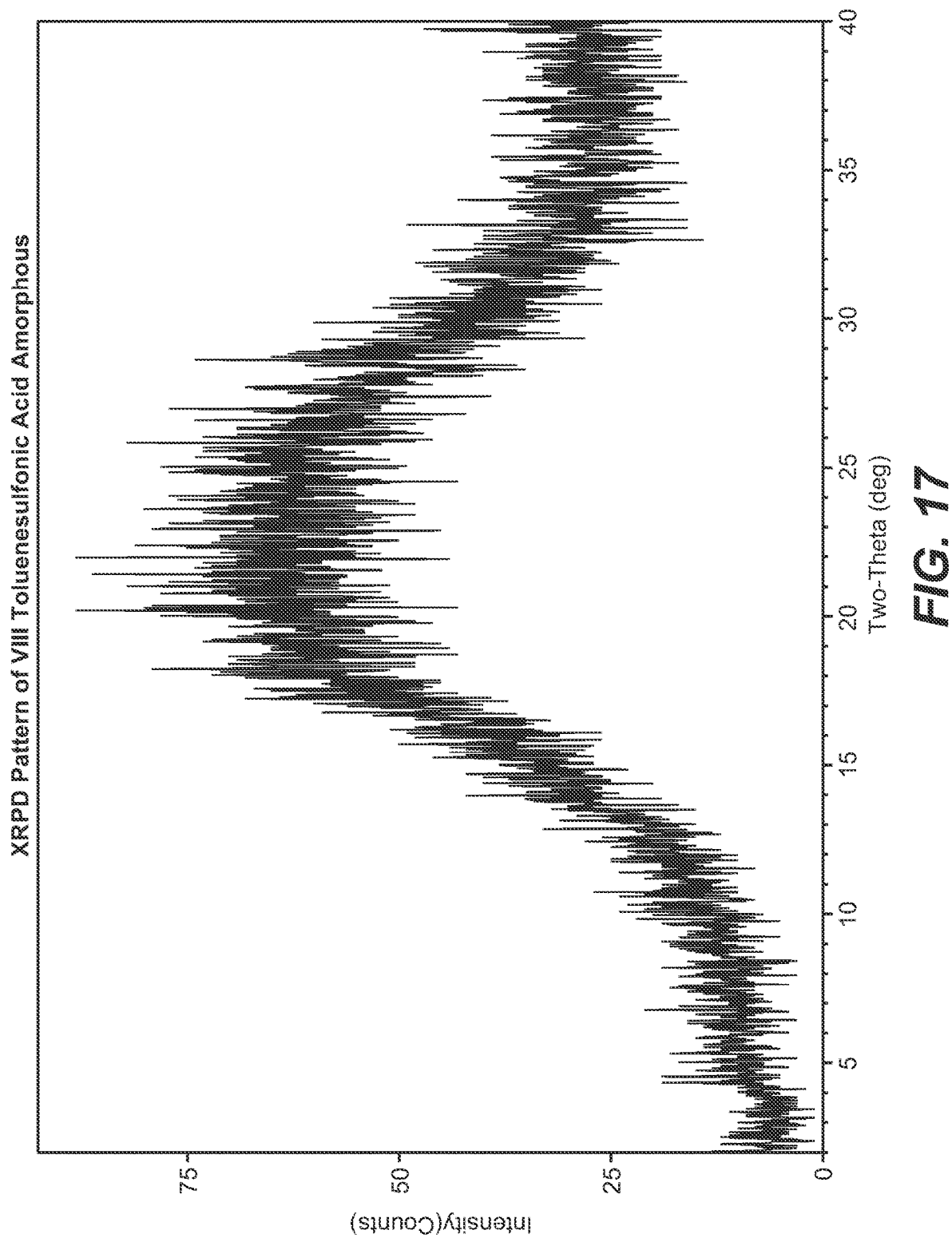
FIG. 17 shows the XRPD pattern of VIII toluenesulfonic acid amorphous.
Figure 18:
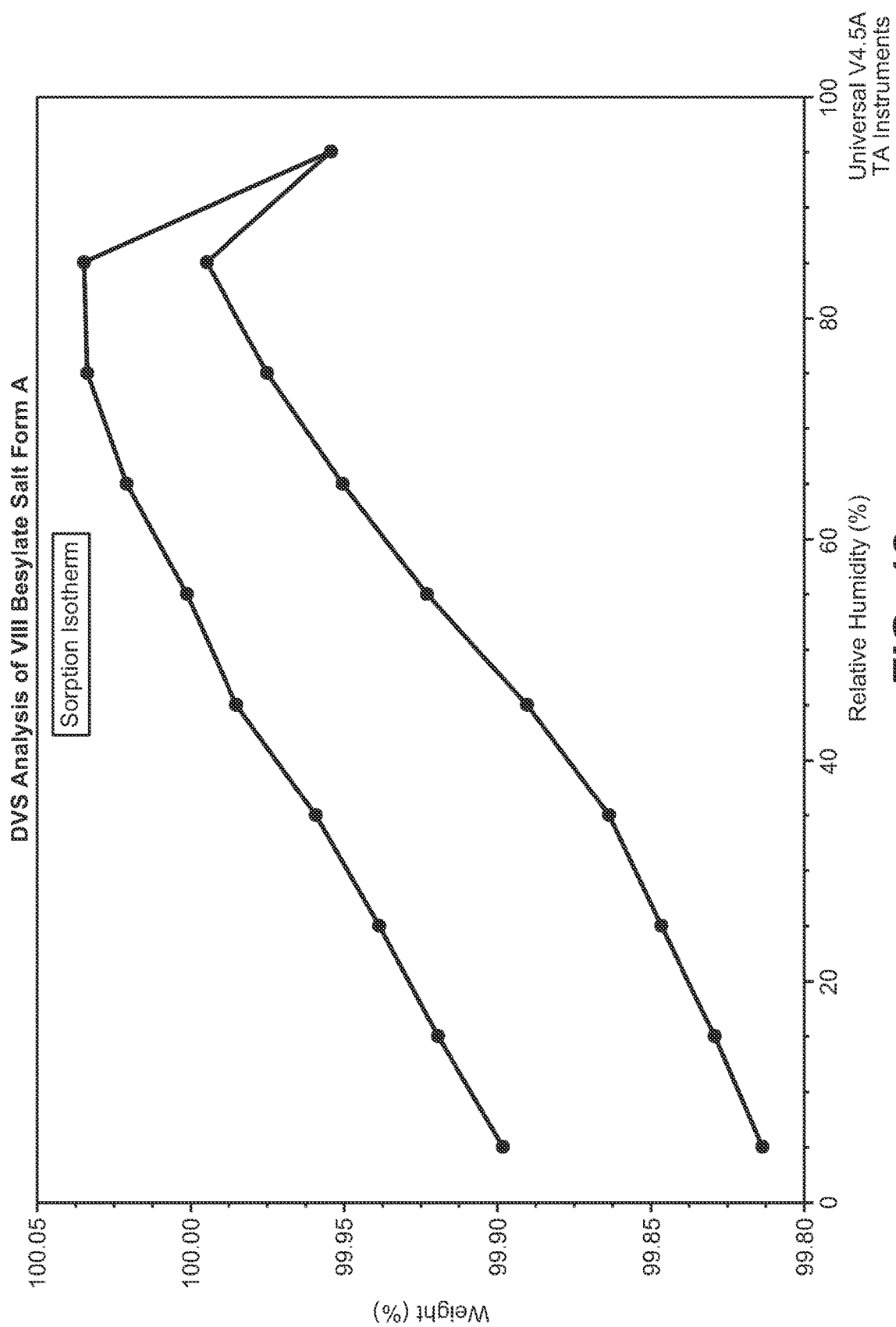
FIG. 18 shows the DVS analysis of VIII besylate salt, form A.

The free base of (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one is an amorphous solid (XRPD, FIG. 4). The glass transition temperature (TG) varies from about 74-96° C. depending on purity and solvent content as measured by differential scanning calorimetry (DSC, FIG. 5).

Approximately 200 crystallization experiments were conducted without success in an attempt to find a crystalline form of (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one free base. Small amounts of crystals were observed in multiple experiments, but these were identified as impurities generated from the synthetic sequence or from raw materials and not as (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one free base. One exception was noted from experiments conducted using nitromethane as a solvent and heptane as antisolvent in a vapor diffusion experiment. A mixture of amorphous and crystalline material was isolated. The crystalline material obtained was determined to be ±1-(1-(4-chloro-3-fluorophenyl)-2-hydroxyethyl)-4-(2-((1-methyl-1H-pyrazol-5-yl)amino)pyrimidin-4-yl)pyridin-2(1H)-one.

A salt screen was conducted to determine if a suitable salt form could be discovered. The $pK_a$ of the free base was determined to be less than 2, which limited the range of possible salt coformers. In addition, salts derived from (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one free base would have a $pH_{max}$ less than 2 and would be expected to disproportionate in water. Thus, it was not clear that a crystalline salt could be prepared or that any salt would have acceptable exposure in vivo (an aqueous environment). Initial attempts to prepare crystalline salts using hydrogen chloride, sulfuric acid, methanesulfonic acid, ethanesulfonic acid, isethionic acid, and ethanedisulfonic acid failed to give any crystalline salt. Eventually crystalline salts were obtained from 1,5-naphthalenedisulfonic acid, p-toluenesulfonic acid and benzenesulfonic acid.

Below are tables showing the primary XRPD peak information for the salts described herein. It is well known to those skilled in the art that the peaks may be shifted up or down depending on the conditions under which the XRPD analysis was conducted. In general, the peaks may shift by +/−0.2. In another aspect, the peaks may be shifted by +/−0.1.

| Besylate salt. | | |
|---|---|---|
| Reflection position °2θ | d spacing (Angstroms) | Relative area |
| 6.16 | 14.342 | 99.3 |
| 7.46 | 11.840 | 19.4 |
| 16.36 | 5.414 | 100 |
| 25.76 | 3.456 | 80.6 |
| 25.98 | 3.423 | 90.2 |

| Tosylate IPA solvate | | |
|---|---|---|
| Reflection position °2θ | d spacing (Angstroms) | Relative area |
| 4.98 | 17.728 | 100 |
| 13.28 | 6.662 | 20.7 |
| 16.28 | 5.440 | 60.4 |
| 19.72 | 4.499 | 73.8 |

| Tosylate Form A | | |
|---|---|---|
| Reflection position °2θ | d spacing (Angstroms) | Relative area |
| 5.76 | 15.327 | 58.4 |
| 13.44 | 6.584 | 36.0 |
| 15.64 | 5.662 | 51.9 |
| 19.40 | 4.572 | 100 |

| Tosylate Form B | | |
|---|---|---|
| Reflection position °2θ | d spacing (Angstroms) | Relative area |
| 7.02 | 12.584 | 40.1 |
| 16.302 | 5.433 | 42.7 |
| 17.30 | 5.122 | 57.8 |
| 21.86 | 4.063 | 100 |

| Naphthalenedisulfonic acid Form I | | |
|---|---|---|
| Reflection position °2θ | d spacing (Angstroms) | Relative area |
| 12.50 | 7.076 | 18.3 |
| 13.86 | 6.385 | 18.6 |

| Naphthalenedisulfonic acid Form II | | |
|---|---|---|
| Reflection position °2θ | d spacing (Angstroms) | Relative area |
| 12.80 | 6.910 | 60 |
| 22.42 | 3.962 | 76.2 |
| 24.92 | 3.570 | 100 |

Figure 19:
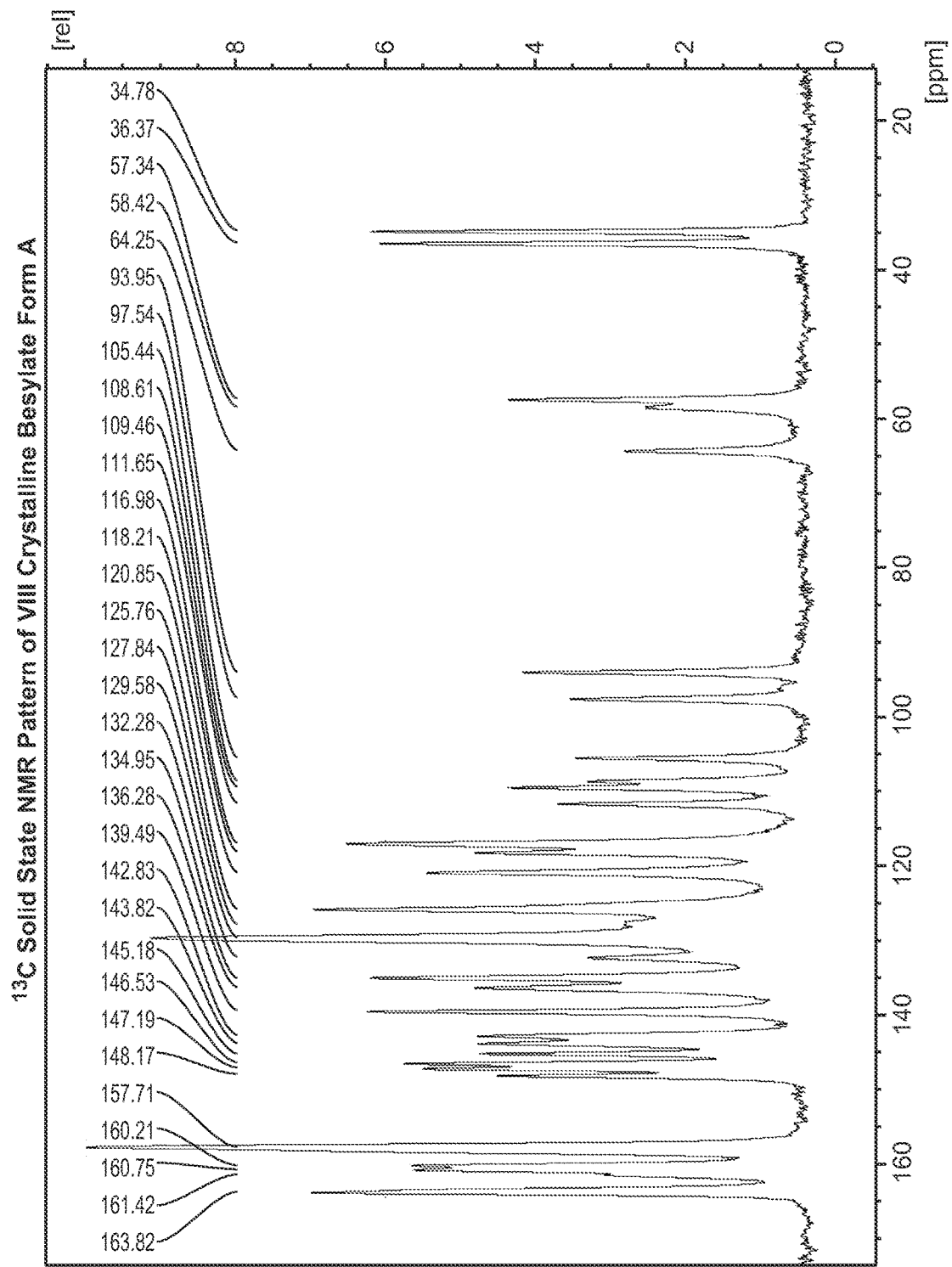
FIG. 19 shows the $^{13}$C solid state NMR pattern of VIII crystalline besylate form A.
Figure 20:
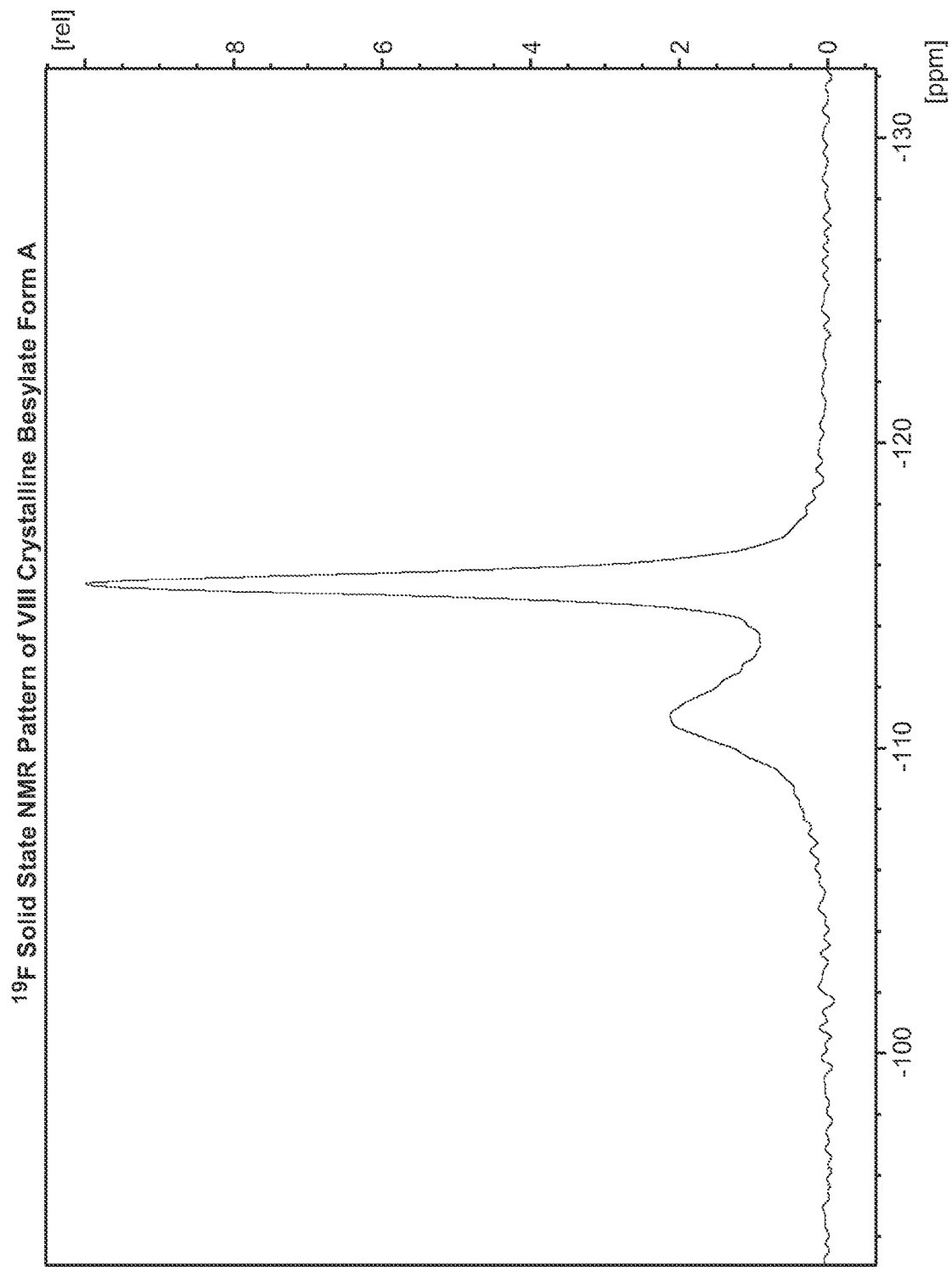
FIG. 20 shows the $^{19}$F solid state NMR pattern of VIII crystalline besylate form A.
Figure 21:
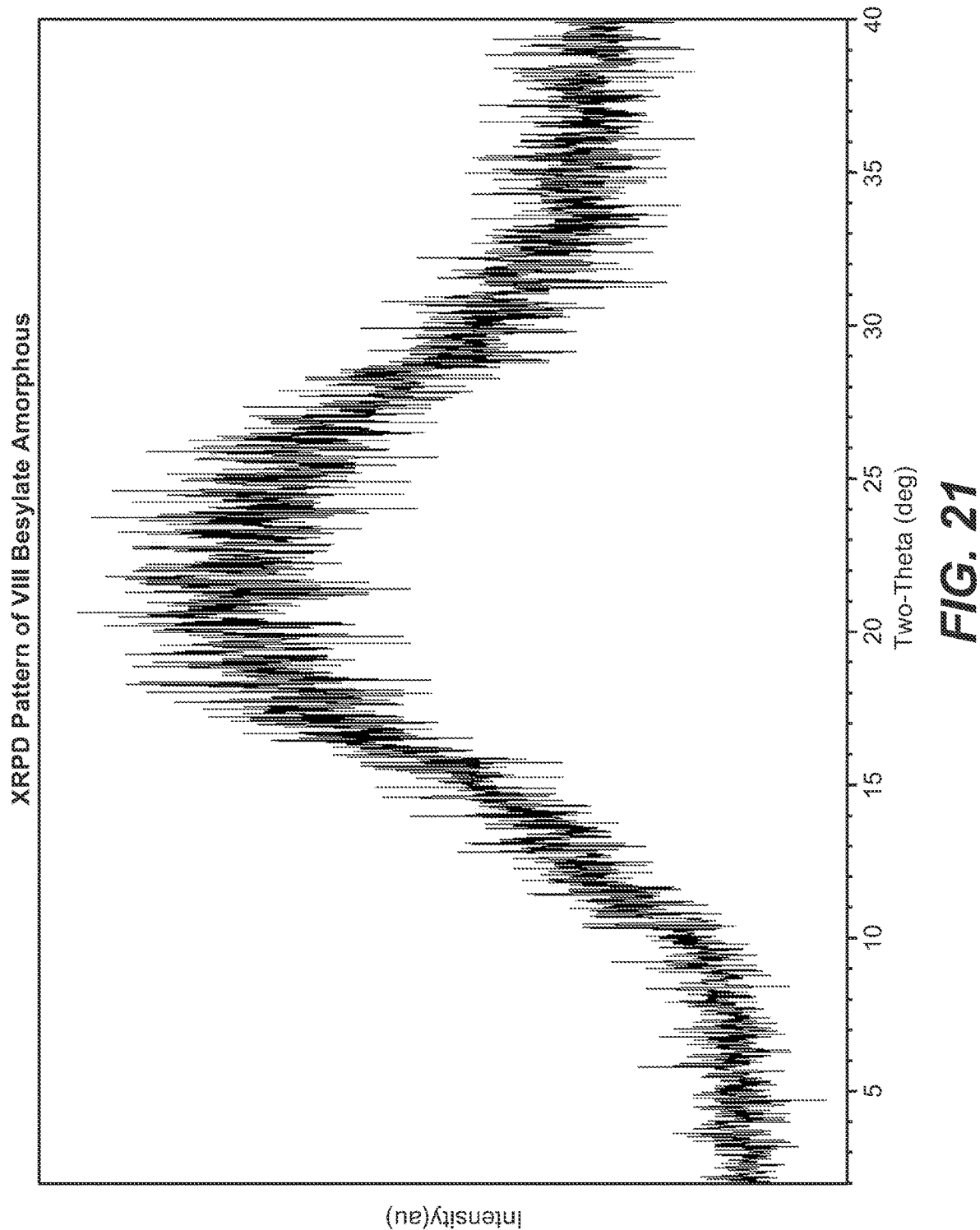
FIG. 21 shows the XRPD pattern of VIII besylate amorphous.

Whether a pharmaceutical product contains a particular crystalline form of a substance, typically in a tablet or capsule, may be determined, for example, using X-ray diffraction, Raman spectroscopy and/or solid state NMR techniques. For Example, the solid state $^{13}C$ and $^{19}F$ NMR spectra of (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one, benzenesulfonate salt crystalline Form A is set forth in FIGS. 19 and 20, respectively. The procedure for obtaining the NMR spectra is set forth below.

(S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one, benzenesulfonate salt crystalline Form A was analyzed using $^{13}C$ and $^{19}F$ solid-state NMR spectroscopy. Spectra were acquired using a Bruker Avance III NMR spectrometer operating at 500.13 MHz for $^1H$, 125.77 MHz for $^{13}C$, and 470.55 MHz for $^{19}F$. $^{13}C$ experiments utilized a Bruker HX double resonance probe tuned for $^1H$ and $^{13}C$, with a 4 mm magic-angle spinning (MAS) module. $^{19}F$ experiments employed a Bruker HFC triple resonance probe tuned to $^1H$, $^{19}F$, and $^{13}C$, also equipped with a 4 mm MAS module. Samples were packed into 4 mm $ZrO_2$ rotors and sealed with Kel-F drive tips. All data were collected at 293 K. Data were collected, processed, and analyzed using Bruker TopSpin™ 3.2 software.

The pulse sequence for $^{13}C$ acquisition employed ramped cross polarization (CP),[1-3] 5-π (total sideband suppression (TOSS),[4] and high power $^1H$ decoupling with a SPINAL64[5] scheme and field strength of 90 kHz. Magic-angle spinning (MAS) was performed at 8000±3 Hz. The $^1H$ 90° pulse width was 2.79 μs and the TOSS sequence employed $^{13}C$ 180° pulses of 6.50 μs. The CP contact time was 3 ms, the recycle delay was 18 s, and a total of 3888 scans were averaged to generate the spectrum. Chemicals shifts were externally referenced by setting the methyl peak of 3-methylglutaric acid to 18.84 ppm relative to tetramethylsilane.[6]

The pulse sequence for $^{19}F$ acquisition employed ramped CP[1-3] and high power $^1H$ decoupling with a SPINAL64[5] scheme and field strength of 71 kHz. Magic-angle spinning (MAS) was performed at 14000±5 Hz. The $^1H$ 90° pulse width was 3.54 μs, the CP contact time was 3 ms, the recycle delay was 18 s, and a total of 16 scans were averaged to generate the spectrum. Chemicals shifts were externally referenced by setting the fluorine peak of polytetrafluoroethylene (PTFE) to −122.38 ppm relative to $CFCl_3$ (determined experimentally by spiking $CFCl_3$ into a PTFE sample).

NMR REFERENCES

1. Pines, A.; Gibby, M. G.; Waugh, J. S., Proton-enhanced nuclear induction spectroscopy. Method for high-resolution NMR of dilute spins in solids. *J. Chem. Phys.* 1972, 56 (4), 1776-7.
2. Stejskal, E. O.; Schaefer, J.; Waugh, J. S., Magic-angle spinning and polarization transfer in proton-enhanced NMR. *J. Magn. Reson.* (1969-1992) 1977, 28 (1), 105-12.
3. Metz, G.; Wu, X.; Smith, S. O., Ramped-amplitude cross polarization in magic-angle-spinning NMR. *J. Magn. Reson. Ser. A* 1994, 110 (2), 219-27.
4. Song, Z.; Antzutkin, O. N.; Feng, X.; Levitt, M. H., Sideband suppression in magic-angle-spinning NMR by a sequence of 5 pi pulses. *Solid State Nucl. Magn. Reson.* 1993, 2 (3), 143-6.
5. Fung, B. M.; Khitrin, A. K.; Ermolaev, K., An improved broadband decoupling sequence for liquid crystals and solids. *J. Magn. Reson.* 2000, 142 (1), 97-101.
6. Barich, D. H.; Gorman, E. M.; Zell, M. T.; Munson, E. J., 3-Methylglutaric acid as $^{13}C$ solid-state NMR standard. *Solid State Nucl. Magn. Reson.* 2006, 30 (3-4), 125-129.

The $^{13}C$ solid-state NMR spectrum of (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one, benzenesulfonate salt crystalline Form A is characterized by strong peaks at chemical shifts of 157.7±0.2 ppm, 129.6±0.2 ppm, 125.8±0.2 ppm, and 117.0±0.2 ppm relative to tetramethylsilane (at 293 K). The $^{19}F$ spectrum is characterized by two isotropic peaks at chemical shifts of −111.1±0.4 ppm and −115.4±0.4 ppm relative to $CFCl_3$ (at 293 K).

The crystalline besylate salt of VIII is a highly crystalline material with a melting point that is acceptable for pharmaceutical dosage form development. The besylate salt form is preferred over the tosylate and 1,5-naphthalenesulfonic acid salt forms based on it's simple solid state landscape (only one crystalline form identified). In addition, the lower hygroscopicity of the besylate salt compared to the tosylate and 1,5-naphthalenedisulfonic acid salt forms is highly desired. The free base of VIII has a low pKa, less than 1.8, and therefore, any salts identified were expected to be unstable in the presence of water due to disproportionation to free base and acid. Therefore, the non-hygroscopicity of the besylate salt was unexpected and led to enhanced stability compared to the tosylate and naphthalenesulfonic acid salt forms.

In another aspect, the present invention provides pharmaceutical compositions comprising a compound of the present invention or a salt or crystalline form of the salt and a pharmaceutically acceptable excipient, such as a carrier, adjuvant, or vehicle. In certain embodiments, the composition is formulated for administration to a patient in need thereof.

The term "patient" or "individual" as used herein, refers to an animal, such as a mammal, such as a human. In one embodiment, patient or individual refers to a human.

The term "pharmaceutically acceptable" means that the compound or composition referred to is compatible chemically and/or toxicologically with the other ingredients (such as excipients) comprising a formulation and/or the patient being treated, particularly humans.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions comprising a compound of the present invention may be administered orally, parenterally, by inhalation spray, topically, transdermally, rectally, nasally, buccally, sublingually, vaginally, intraperitoneal, intrapulmonary, intradermal, epidural or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

In one embodiment, the composition comprising a compound of the present invention is formulated as a solid dosage form for oral administration. Solid dosage forms for oral administration include capsules, tablets, pills, powders, and granules. In certain embodiments, the solid oral dosage form comprising a compound of formula (I) or a salt thereof further comprises one or more of (i) an inert, pharmaceutically acceptable excipient or carrier, such as sodium citrate or dicalcium phosphate, and (ii) filler or extender such as starches, lactose, sucrose, glucose, mannitol, or silicic acid, (iii) binders such as carboxymethylcellulose, alginates, gelatin, polyvinylpyrrolidinone, sucrose or acacia, (iv) humectants such as glycerol, (v) disintegrating agent such as agar, calcium carbonate, potato or tapioca starch, alginic acid, certain silicates or sodium carbonate, (vi) solution retarding agents such as paraffin, (vii) absorption accelerators such as quaternary ammonium salts, (viii) a wetting agent such as cetyl alcohol or glycerol monostearate, (ix) absorbent such as kaolin or bentonite clay, and (x) lubricant such as talc, calcium stearate, magnesium stearate, polyethylene glycols or sodium lauryl sulfate. In certain embodiments, the solid oral dosage form is formulated as capsules, tablets or pills. In certain embodiments, the solid oral dosage form further comprises buffering agents. In certain embodiments, such compositions for solid oral dosage forms may be formulated as fillers in soft and hard-filled gelatin capsules comprising one or more excipients such as lactose or milk sugar, polyethylene glycols and the like.

In certain embodiments, tablets, dragees, capsules, pills and granules of the compositions comprising a compound of formula I or salt thereof optionally comprise coatings or shells such as enteric coatings. They may optionally comprise opacifying agents and can also be of a composition that they release the active ingredient(s) only, or preferentially, in a certain part of the intestinal tract, optionally, in a delayed manner. Examples of embedding compositions include polymeric substances and waxes, which may also be employed as fillers in soft and hard-filled gelatin capsules using such excipients as lactose or milk sugar as well as high molecular weight polethylene glycols and the like.

In another embodiment, a composition comprises microencapsulated compound of the present invention, and optionally, further comprises one or more excipients.

In another embodiment, compositions comprise liquid dosage formulations comprising a compound of formula I or salt thereof for oral administration and optionally further comprise one or more of pharmaceutically acceptable emulsions, microemulsions, solutions, suspensions, syrups and elixirs. In certain embodiments, the liquid dosage form optionally, further comprise one or more of an inert diluent such as water or other solvent, a solubilizing agent, and an emulsifier such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols or fatty acid esters of sorbitan, and mixtures thereof. In certain embodiments, liquid oral compositions optionally further comprise one or more adjuvant, such as a wetting agent, a suspending agent, a sweetening agent, a flavoring agent and a perfuming agent.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

In certain embodiments, the composition for rectal or vaginal administration are formulated as suppositories which can be prepared by mixing a compound of the present invention with suitable non-irritating excipients or carriers such as cocoa butter, polyethylene glycol or a suppository wax, for example those which are solid at ambient temperature but liquid at body temperature and therefore melt in the rectum or vaginal cavity and release the compound of the present invention.

Example dosage forms for topical or transdermal administration of a compound of the present invention include ointments, pastes, creams, lotions, gels, powders, solutions, sprays, inhalants or patches. The compound of the present invention is admixed under sterile conditions with a pharmaceutically acceptable carrier, and optionally preservatives or buffers. Additional formulation examples include an ophthalmic formulation, ear drops, eye drops or transdermal patches. Transdermal dosage forms can be made by dissolving or dispensing the compound of the present invention in medium, for example ethanol or dimethylsulfoxide. Absorption enhancers can also be used to increase the flux of the compound across the skin. The rate can be controlled by either providing a rate controlling membrane or by dispersing the compound in a polymer matrix or gel.

Nasal aerosol or inhalation formulations of a compound of the present invention may be prepared as solutions in saline, employing benzyl alcohol or other suitable preservatives, absorption promoters to enhance bioavailability, fluorocarbons, and/or other conventional solubilizing or dispersing agents.

In certain embodiments, pharmaceutical compositions may be administered with or without food. In certain embodiments, pharmaceutically acceptable compositions are administered without food. In certain embodiments, pharmaceutically acceptable compositions of this invention are administered with food.

Specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound of the present invention in the composition will also depend upon the particular compound in the composition.

In one embodiment, the therapeutically effective amount of the compound of the invention administered parenterally per dose will be in the range of about 0.01-100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, contain from about 5 to about 100 mg of the compound of the invention.

An example tablet oral dosage form comprises about 2 mg, 5 mg, 25 mg, 50 mg, 100 mg, 250 mg or 500 mg of a compound of formula (I) or salt thereof, and further comprises about 5-30 mg anhydrous lactose, about 5-40 mg sodium croscarmellose, about 5-30 mg polyvinylpyrrolidone (PVP) K30 and about 1-10 mg magnesium stearate. The process of formulating the tablet comprises mixing the powdered ingredients together and further mixing with a solution of the PVP. The resulting composition can be dried, granulated, mixed with the magnesium stearate and compressed to tablet form using conventional equipment. An example of an aerosol formulation can be prepared by dissolving about 2-500 mg of a compound of formula I or salt thereof, in a suitable buffer solution, e.g. a phosphate buffer, and adding a tonicifier, e.g. a salt such sodium chloride, if desired. The solution may be filtered, e.g. using a 0.2 micron filter, to remove impurities and contaminants.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and examples, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, published applications, and scientific literature referred to herein establish the knowledge of those skilled in the art and are hereby incorporated by reference in their entirety to the same extent as if each was specifically and individually indicated to be incorporated by reference. Any conflict between any reference cited herein and the specific teachings of this specifications shall be resolved in favor of the latter. Likewise, any conflict between an art-understood definition of a word or phrase and a definition of the word or phrase as specifically taught in this specification shall be resolved in favor of the latter.

What is claimed is:

1. A process for the preparation of 4-(2-(methylthio)pyrimidin-4-yl)pyridin-2(1H)-one (VII) comprising the steps of:
    (a) contacting 2-fluoro-4-iodopyridine with a metallating agent in an aprotic organic solvent to afford an organomagnesium compound, which is reacted with 4-chloro-2(methylthio)pyrimidine in the presence of a palladium catalyst to afford 4-(2-fluoropyridin-4-yl)-2-(methylthio)pyrimidine (X);
    (b) treating X with potassium tert-butoxide in tetrahydrofuran (THF) and subsequently with an aqueous acid to afford 4-(2-(methylthio)pyrimidin-4-yl)pyridin-2(1H)-one (VII).

2. The process according to claim 1 wherein the palladium catalyst is (1,3-diisopropylimidazol-2-ylidene)(3-chloropyridyl)palladium(II) dichloride, the metallating agent is i-PrMgCl and LiCl, and the aprotic solvent is THF.

* * * * *